United States Patent [19]
Teng et al.

[11] Patent Number: 6,087,482
[45] Date of Patent: Jul. 11, 2000

[54] HETEROATOMIC OLIGONUCLEOSIDE LINKAGES

[75] Inventors: Kelly Teng, San Diego; Yogesh Sanghvi; Phillip Dan Cook, both of San Marcos, all of Calif.

[73] Assignee: Isis Pharmaceuticals, Inc., Carlsbad, Calif.

[21] Appl. No.: 08/522,374

[22] PCT Filed: Mar. 30, 1994

[86] PCT No.: PCT/US94/03536

§ 371 Date: Sep. 18, 1995

§ 102(e) Date: Sep. 18, 1995

[87] PCT Pub. No.: WO94/22886

PCT Pub. Date: Oct. 13, 1994

Related U.S. Application Data

[63] Continuation-in-part of application No. 08/039,846, Mar. 30, 1993, abandoned, which is a continuation-in-part of application No. 07/903,160, Jun. 24, 1992, abandoned, which is a continuation-in-part of application No. PCT/US91/05713, Aug. 12, 1991, abandoned, which is a continuation-in-part of application No. PCT/US92/04294, May 21, 1992, which is a continuation-in-part of application No. 07/703,619, May 21, 1991, Pat. No. 5,378,825, which is a continuation-in-part of application No. 07/566,836, Aug. 13, 1990, Pat. No. 5,223,618, which is a continuation-in-part of application No. 07/558,663, Jul. 27, 1990, Pat. No. 5,138,045.

[51] Int. Cl.$^7$ .......................... C07H 19/00; C07H 21/02; C07H 21/04; C12Q 1/68

[52] U.S. Cl. .......................... 536/22.1; 435/6; 536/23.1; 536/24.5; 536/24.3; 536/24.31; 536/24.32; 536/25.3; 514/44

[58] Field of Search ................. 435/6; 536/22.1, 536/23.1, 24.5, 25.3, 24.3, 24.31, 24.32; 514/44

[56] References Cited

U.S. PATENT DOCUMENTS

| | | | |
|---|---|---|---|
| 3,687,808 | 8/1972 | Merigan et al. | 295/28 |
| 4,472,572 | 9/1984 | Shizuya | 536/27 |
| 5,270,185 | 12/1993 | Margolskee | 435/91.41 |
| 5,470,967 | 11/1995 | Huie et al. | 536/24.3 |
| 5,677,437 | 10/1997 | Teng et al. | 536/23.1 |

FOREIGN PATENT DOCUMENTS

| | | |
|---|---|---|
| WO 92/02534 | 2/1992 | WIPO . |
| WO 92/03568 | 3/1992 | WIPO . |
| WO 92/05186 | 4/1992 | WIPO . |
| WO 93/18052 | 9/1993 | WIPO . |

OTHER PUBLICATIONS

Schumm "Essentials of Biochemistry" Essentials of medical education series. F. A. Davis Company, p. 36, 1988.

Stein et al. "Antisense Oligonucleotides as Therapeutic Agents—Is the Bullet Really Magical?" Science, vol. 261, pp. 1004–1012, Aug. 1993.

Vasseur et al. "Oligonucleosides: Synthesis of a Novel Methylhydroxylamine–Linked Nucleoside Dimer and Its Incorporation into Antisense Sequences" J. Am. Chem. Soc., vol. 114, pp. 4006–4007, 1992.

Kim et al. "Regiospecific and Highly Stereoselective Electrophilic Addition to Furanoid Glycals: Synthesis of Phosphonate Nucleotide Analogues with Potent Activity against HIV" J. Org. Chem., vol. 56, pp. 2642–2647, 1991.

(List continued on next page.)

*Primary Examiner*—Jezia Riley
*Attorney, Agent, or Firm*—Woodcock Washburn Kurtz Mackiewicz & Norris LLP

[57] ABSTRACT

Oligonucleotide-mimicking macromolecules that have improved nuclease resistance are provided. Replacement of the normal phosphorodiester inter-sugar linkages found in natural oligonucleotides with four atom linking groups provide unique compounds that are useful in regulating RNA expression and in therapeutics. Methods of synthesis and use also are disclosed.

9 Claims, 25 Drawing Sheets

OTHER PUBLICATIONS

Bergstrom et al. "Organoiron–Mediated Alkylation of Phosphite esters: Synthesis of (Dicarbonyl)(cyclopentadienyl)iron–Derived Nucleoside Phosphonates Esters" J. Org Chem., vol. 56, pp. 873–876, 1992.

Neidlein et al. "Syntheses and investigations of [Oxazolo [2,3- [isoindol–9b(2H)–yl]phosphonates and –phosphinates: a new class of heterocycles" Helvetica Chimica, vol. 76, pp. 2407–2417, 1993.

Verheggen et al. "Synthesis and antiherpes virus activity of 1,5–anhydrohexitol nucleosides" J. Med. Chem., vol. 36, pp. 2033–2040, 1993.

Jois et al. "Synthesis and Antiviral Evaluation of Soe Novel [1,2,4]Triazolo[4,3–b][1,2,4]triazole Nucleoside Analogs" J. Heterocyclic Chem., vol. 30, pp. 1289–1292, 1993.

Bower et al. "Oligodeoxyribonucleoside methylphosphonates. NMR and UV spectroscopy studies of R –R and S –S methyphosphonate (me) modified duplexes of {[GGAAT-TCC]}" Nucleic acids research, vol. 15, pp. 4915–4930, 1987.

Abdel–Magid, et al., "Reductive Amination of Aldehydes and Ketones by Using Sodium Triacetoxyborohydride", *Tetra. Lts.* 1990, 31, 5595–5598.

Debart, F. et al., "Intermolecular Radical C—C Bond Formation: Synthesis of a Novel Dinucleoside Linker for Non–anionic Antisense Oligonucleosides", *Tetra. Ltrs.* 1992, 33, 2645–2648.

Egholm, M. et al., "Peptide Nucleic Acids (PNA). Oligonucleotide Analogues with an Achiral Peptide Backbone", *J. of the Am. Chem. Soc.* 1992, 114, 1895–1897.

Giannis, A. et al., "Fragmentation and wittig olefination of glucosamine derivatives—a simple route to open chain amino sugars and chiral glycerols", *Tetrahedron Letters* 1988, 44(23), 7177–7180.

Greene and Wuts in "Protective Groups in Inorganic Synthesis", John Wiley & Sons, Inc., 1991, pp. 175–223.

Halford, M. & Jones, A.S., "Synthetic Analogues of Polynucleotides", *Nature* 1968, 217, 638–639.

Hart, D.J. et al., "Bis(trimethylstannyl)benzopinacolate–mediated intermolecular free–radical carbon–carbon bond–forming reactions: A new one–carbon homologation", *J. Am. Chem. Soc.* 1988, 110, 1631–1633.

Hyrup, et al., "Modification of the Binding Affinity of Peptide Nucleic Acids (PNA). PNA with Extended Backbones Consisting of 2–Aminoethyl–β–alanine or 3–Aminopropylglycine Units", *J. Chem. Soc. Chem. Commun.* 1993, 518–519.

Inouye, M. et al., "Selective coloration of spiro pyridopyrans for guanosine derivatives", *J. Am. Chem. Soc.* 1992, 114, 778–780.

Kool, E. T. and Prakash, G., "Molecular recognition by circular oligonucleotides. Strong binding of single–stranded DNA and RNA", *J. Chem. Soc. Chem. Commun.* 1991, 1161–1163.

Lin et al., "Synthesis and Biological Activity of Several Amino Analogues of Thymidine", *J.Med.Chem.* 1978, 21, 109–112.

Ma, M.Y.X. et al., "Design and synthesis of RNA miniduplexes via a synthetic linker approach. 2. generation of covalently closed, double–stranded cyclic HIV–1 TAR RNA analogs with high Tat–binding affinity", *Nucleic Acids Research* 1993, 21(11), 2585–2589.

March, J. in "Advanced Organic Chemistry, Reactions, Mechanisms and Structure", John Wiley & Sons, New York, 1992, p. 352.

Milligan, J.F. et al., "Current Concepts in Antisense Drug Design", *J. of Medicinal Chemistry* 1993, 36(14), 1923–1937.

Pauling, L., "Molecular architecture and biological reactions", *Biological Science (Chemical and Engineering News)* 1946, 24(10), 1375–1377.

Perkins, T.A. et al., "Accelerated displacement of duplex DNA strands by a synthetic circular oligonucleotide", *J. Chem. Soc. Chem. Commun.* 1993, 215–216.

Rebek, J. "Molecular Recognition and Biophysical Organic Chemistry", *Account of Chemical Research* 1990, 23(12), 399–404.

Rentzeperis et al., "Contribution of loops and nicks to the formation of DNA dumbbells: Melting behavior and ligand binding", Biochemistry 1993, 32, 2564–2572.

Trapani et al., "N–1 Alkenyl–N, S–Diacyl–2–Aminobenzenethiols (Enamides) by Ring–Opening of 2,3–Dihydro–1,3–benothiazoles with Aliphatic Carboxylic Anhydrides", *Communications* 1988, 6, 84–87.

Tuladhar, S. M. and D'Silva, C., "A synthetic route to poly–N,N$^1$–dimthylethylenediamines", *Tetrahedron Letters* 1992, 33(16), 2203–2206.

Uhlmann, E. and Peyman, A., "Antisense oligonucleotides: A new therapeutic principle", *Chemical Reviews* 1990, 90(4), 544–583.

Zuckerman, R. et al., "Efficient method for the preparation of peptoids [oligo(N–substituted glycines)] by submonomer solid–phase synthesis", *J. Am. Chem. Soc.* 1992, 114, 10646–10647.

a TBDPS-Cl, Pyridine, 23 °C, 10 hr.

b ClCH2OCH2Ph, (ipr)2NEt, CH2Cl2, 23 °C, 14 hr.

c NaH, DMF, 0 to 23 °C, 4 hr.

d NaBH4, MeOH, 0 °C, 1 hr then 23 °C, 6 hr.

a. BzCl, Et3N, CH2Cl2, 23 °C, 8hr.
b. HF-pyridine, 23 °C, 4 hr.
c. CrO3, Ac2O/pyridine, *t*-BuOH, DMF/CH2Cl2, 23 °C, 48 hr.
d. CF3COOH, 23 °C, 1 hr.
e. Pb(OAc)4, pyridine, DMF, 23 °C, 16 hr.

a. N-hydroxysuccinimide, pyridine, toluene.

b. AIBN, benzene, reflux.

c. OsO₄(cat.), NMO, THF/H₂O.

| | | | |
|---|---|---|---|
| 140 | B = A | Q = O | X = OH |
| 141 | B = 3-deaza G | Q = O | X = OH |
| 142 | B = A | Q = O | X = F |
| 143 | B = U | Q = O | X = OCH3 |
| 144 | B = C | Q = O | X = O-CH2-CH=CH2 |
| 145 | B = G | Q = O | X = OH |
| 146 | B = 6-thio G | Q = O | X = OH |
| 147 | B = G | Q = O | X = CH3 |
| 148 | B = 2-NH2 A | Q = O | X = OH |
| 149 | B = A | Q = CH2 | X = OH |
| 150 | B = I | Q = CH2 | X = OH |
| 151 | B = U | Q = O | X = F |
| 152 | B = G | Q = O | X = F |
| 153 | B = C | Q = O | X = F |

HETEROATOMIC OLIGONUCLEOSIDE LINKAGES

CROSS REFERENCE TO RELATED APPLICATIONS

Ser. No. 08/039,846 is a continuation-in-part of application Ser. No. 07/903,160, filed on Jun. 24, 1992 (now abandoned), application PCT/US91/05713 filed on Aug. 12, 1991 (now abandoned), and application PCT/US92/04294 filed on May 21, 1992 (now Ser. No. 08/150,079). Application Ser. No. 07/903,160 is a continuation-in-part of application Ser. No. 07/703,619, filed on May 21, 1991 (now U.S. Pat. No. 5,378,825), application Ser. No. 07/566,836, filed on Aug. 13, 1990 (now U.S. Pat. No. 5,223,618), application Ser. No. 07/558,663, filed on Jul. 27, 1990 (now U.S. Pat. No. 5,138,045), and application PCT/US92/04294. Application PCT/US92/04294 is a continuation-in-part of application Ser. No. 07/703,619. Application PCT/US91/05713 is a continuation-in-part of application Ser. No. 07/566,836, and application Ser. No. 07/703,619 is a continuation-in-part of application Ser. No. 07/566,836 and application Ser. No. 07/558,663. Each of the foregoing patent applications are assigned to the assignee of this application and are incorporated by reference herein.

FIELD OF THE INVENTION

This invention relates to the design, synthesis and application of nuclease resistant macromolecules that function as oligonucleotide mimics and are useful for therapeutics, diagnostics and as research reagents. The macromolecules have modified linkages in place of the phosphorodiester inter-sugar linkages found in wild type nucleic acids. The macromolecules are resistant to nuclease degradation and are capable of modulating the activity of DNA and RNA. Methods for synthesizing the macromolecules and for modulating the production of proteins, utilizing the macromolecules of the invention are also provided. Also provided are intermediate compositions useful in the synthesis of the macromolecules.

BACKGROUND OF THE INVENTION

It is well known that most of the bodily states in mammals, including most disease states, are effected by proteins. Proteins, either acting directly or through their enzymatic functions, contribute in major proportion to many diseases in animals and man.

Classical therapeutics generally has focused upon interactions with proteins in an effort to moderate their disease causing or disease potentiating functions. Recently, however, attempts have been made to moderate the production of proteins by interactions with the molecules (i.e., intracellular RNA) that direct their synthesis. These interactions have involved hybridization of complementary "antisense" oligonucleotides or certain analogs thereof to RNA. Hybridization is the sequence-specific hydrogen bonding of oligonucleotides or oligonucleotide analogs to RNA or to single stranded DNA. By interfering with the production of proteins, it has been hoped to effect therapeutic results with maximum effect and minimal side effects.

The pharmacological activity of antisense oligonucleotides and oligonucleotide analogs, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modification of oligonucleotides to render them resistant to nucleases therefore is greatly desired.

Modification of oligonucleotides to enhance nuclease resistance generally has taken place on the phosphorus atom of the sugar-phosphate backbone. Phosphorothioates, methyl phosphonates, phosphoramidites and phosphotriesters have been reported to confer various levels of nuclease resistance. Phosphate-modified oligonucleotides, however, generally have suffered from inferior hybridization properties. See, e.g., Cohen, J. S., ed. *Oligonucleotides: Antisense Inhibitors of Gene Expression*, (CRC Press, Inc., Boca Raton Fla., 1989).

Another key factor is the ability of antisense compounds to traverse the plasma membrane of specific cells involved in the disease process. Cellular membranes consist of lipid-protein bilayers that are freely permeable to small, nonionic, lipophilic compounds and are inherently impermeable to most natural metabolites and therapeutic agents. See, e.g., Wilson, *Ann. Rev. Biochem.* 1978, 47, 933. The biological and antiviral effects of natural and modified oligonucleotides in cultured mammalian cells have been well documented. It appears that these agents can penetrate membranes to reach their intracellular targets. Uptake of antisense compounds into a variety of mammalian cells, including HL-60, Syrian Hamster fibroblast, U937, L929, CV-1 and ATH8 cells has been studied using natural oligonucleotides and certain nuclease resistant analogs, such as alkyl triesters and methyl phosphonates. See, e.g., Miller, et al., *Biochemistry* 1977, 16, 1988; Marcus-Sekura, et al., *Nuc. Acids Res.* 1987, 15, 5749; and Loke, et al., *Top. Microbiol. Immunol.* 1988, 141, 282.

Often, modified oligonucleotides and oligonucleotide analogs are internalized less readily than their natural counterparts. As a result, the activity of many previously available antisense oligonucleotides has not been sufficient for practical therapeutic, research or diagnostic purposes. Two other serious deficiencies of prior art compounds designed for antisense therapeutics are inferior hybridization to intracellular RNA and the lack of a defined chemical or enzyme-mediated event to terminate essential RNA functions.

Modifications to enhance the effectiveness of the antisense oligonucleotides and overcome these problems have taken many forms. These modifications include heterocyclic base modifications, sugar moiety modifications and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the pro-chiral phosphate moiety. For example, Matteucci, *Tetrahedron Letters* 1990, 31, 2385 disclosed the replacement of the phosphorus atom with a methylene group. Cormier, et al., *Nucleic Acids Research* 1988, 16, 4583, disclosed replacement of phosphorus with a diisopropylsilyl moiety to yield homopolymers having poor solubility and hybridization properties. Stirchak, et al., *Journal of organic Chemistry* 1987, 52, 4202, disclosed replacement of phosphorus linkages by short homopolymers containing carbamate or morpholino linkages to yield compounds having poor solubility and inferior hybridization properties. Mazur, et al., *Tetrahedron* 1984, 40, 3949, disclosed replacement of a phosphorus linkage with a phosphonate linkage but only for a homotrimer molecule. Goodchild, *Bioconjugate Chemistry* 1990, 1, 165, disclosed ester linkages that are enzymatically degraded by esterases and, therefore, are not suitable for antisense applications.

A recent publication by Tronchet, et. al, *J. Carbohydrate Chemistry,* 1991, 10, 723, reported the use of an oxyimino intergylcosidic linkage between two monosaccharides to form a disaccharide. In forming this linkages, a first carbonyl sugar, either a hexose or a pentose, was reacted with a second O-aminohexose sugar.

Ats, et al., *Carbohydrate Research* 1992, 233, 125–139 have reported use of a O—$CH_2$—$CH_2$—O backbone linker between two monosaccharides to form a disaccharide.

The limitations of available methods for modification of the phosphorus backbone have led to a continuing and long felt need for other modifications which provide resistance to nucleases and satisfactory hybridization properties for antisense oligonucleotide diagnostics and therapeutics.

OBJECTS OF THE INVENTION

It is an object of the invention to provide oligonucleotide analogs for diagnostic, research, and therapeutic use.

It is a further object of the invention to provide oligonucleotide analogs having enhanced cellular uptake.

Another object of the invention is to provide oligonucleotide analogs having greater efficacy than unmodified antisense oligonucleotides.

It is yet another object of the invention to provide methods for synthesis and use of oligonucleotide analogs.

These and other objects will become apparent to persons of ordinary skill in the art from a review of the present specification and the appended claims.

BRIEF SUMMARY OF THE INVENTION

The present invention provides compositions that are useful for modulating the activity of an RNA or DNA molecule and that generally comprise oligonucleotide-mimicking macromolecules. The macromolecules are constructed from a plurality of linked nucleosides. In constructing these macromolecules, the phosphorodiester linkage of the sugar phosphate backbone found in wild type nucleic acids has been replaced with a 3 or 4 atom linking groups. Such linking groups maintain a desired atomic spacing between the 3'-carbon of one nucleoside and the 4'-carbon (as numbered in reference to the numbering of a pentofuranosyl nucleoside) of an adjacent nucleoside. The oligonucleotide-mimicking macromolecules of the invention comprise a selected linked sequence of nucleosides that are specifically hybridizable with a preselected nucleotide sequence of single stranded or double stranded DNA or RNA.

The oligonucleotide-mimicking macromolecules of the invention are synthesized conveniently, through solid state support or solution methodology, to be complementary to or at least specifically hybridizable with a preselected nucleotide sequence of the RNA or DNA. Solid state support synthesis is effected utilizing commercially available nucleic acid synthesizers. The use of such synthesizers is generally understood by persons of ordinary skill in the art as being effective in generating nearly any desired oligonucleotide or oligonucleotide mimic of reasonable length.

The oligonucleotide-mimicking macromolecules of the invention also can include nearly any modification known in the art to improve the properties of wild type oligonucleotides. In particular, the macromolecules can incorporate modifications known to increase nuclease resistance or hybridization.

In accordance with the present invention, novel macromolecules that function as antisense oligonucleotide mimics are provided to enhance cellular uptake, nuclease resistance, and hybridization properties and to provide a defined chemical or enzymatically mediated event to terminate essential RNA functions.

It has been found that certain oligonucleotide-mimicking macromolecules can be useful in therapeutics and for other objects of this invention. At least a portion of the macromolecules of the invention has structure 1:

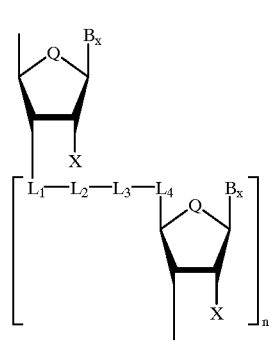

wherein:
$L_1$-$L_2$-$L_3$-$L_4$ is $CR_{1a}R_{1b}$-$CR_{2a}R_{2b}$-$CR_{3a}R_{3b}$-$Z_4$, $CR_{1a}R_{1b}$-$CR_{2a}R_{2b}$-$Z_3$-$Z_4$, $CR_{1a}R_{1b}$-$Z_2$-$CR_{2a}R_{2b}$-$Z_4$, $Z_1$-$CR_{1a}R_{1b}$-$CR_{2a}R_{2b}$-$Z_4$, $CR_{1a}R_{1b}$-$Z_2$-$Z_3$-$Z_4$, $Z_1$-$CR_{2a}R_{2b}$-$Z_3$-$Z_4$ or $Z_1$-$Z_2$-$CR_{3a}R_{3b}$-$Z_4$;

$Z_1$, $Z_2$, $Z_3$ and $Z_4$ are, independently, $NR_4$, S, SO, $SO_2$ Se, P(=$J_1$)$J_2$, Si($R_6$)$_2$, or O;

$R_{1a}$, $R_{1b}$, $R_{2a}$, $R_{2b}$, $R_{3a}$ and $R_{3b}$ are, independently, H, $R_5$, O—$R_5$, S—$R_5$, $NR_4R_5$; or, independently, together $R_{1a}$ and $R_{1b}$, or $R_{2a}$ and $R_{2b}$, or $R_{3a}$ and $R_{3b}$ are =O;

X is H, OH, O—$R_5$, S—$R_5$, $NR_4$—$R_5$, $R_5$, F, Cl, Br, CN, $CF_3$, $OCF_3$, OCN, $SOCH_3$, $SO_2CH_3$, $ONO_2$, $NO_2$, $N_3$, heterocycloalkyl, heterocycloalkaryl, aminoalkylamino, polyalkylamino or substituted silyl, an RNA cleaving group, a group for improving the pharmacokinetic properties of an oligonucleotide, or a group for improving the pharmacodynamic properties of an oligonucleotide;

$J_1$ is O, S, Se, or $NR_4$;

$J_2$ is OH, $OR_5$, SH, $SR_5$, SeH, $R_5$, $BH_3$ or $NR_4R_5$;

$R_4$, $R_5$ and $R_6$ are, independently, H; $C_1$ to $C_{10}$ straight or branched chain lower alkyl or substituted lower alkyl; $C_2$ to $C_{10}$ straight or branched chain lower alkenyl or substituted lower alkenyl; $C_2$ to $C_{10}$ straight or branched chain lower alkynyl or substituted lower alkynyl; a $^{14}C$ containing lower alkyl, lower alkenyl or lower alkynyl; $C_7$ to $C_{14}$ substituted or unsubstituted alkaryl or aralkyl; a $^{14}C$ containing $C_7$ to $C_{14}$ alkaryl or aralkyl; $C_6$ to $C_{14}$ aryl; alicyclic; heterocyclic; a reporter molecule; an RNA cleaving group; a group for improving the pharmacokinetic properties of an oligonucleotide; or a group for improving the pharmacodynamic properties of an oligonucleotide; and where said substituents are OH, =O, $CO_2H$, O-alkyl, SH, S-alkyl, NH-alkyl, N-(alkyl)$_2$, alkyl, F, Cl, Br, CN, $CF_3$, $OCF_3$, OCN, $SOCH_3$, $SO_2CH_3$, $ONO_2$, $NO_2$, $N_3$, $NH_2$, heterocycloalkyl, aryl, aralkyl, sulfide, silyl, intercalators, conjugates, imidazoles, amides, ester, ethers, carbonates, carbamates, ureas, polyamines, polyamides, polyethylene glycols or polyethers;

Q is O, CHF, $CF_2$ or $CH_2$;

n is an integer greater than 0; and

Bx is a variable heterocyclic base moiety.

The remainder of the molecule is composed of chemical functional groups that do not hinder, and preferably enhance, hybridization with RNA or single stranded or double stranded DNA. For example, structure 1 at its 3' and 5' terminal ends can, independently, bear any of the following groups: H, hydroxyl, aminomethyl, hydrazinomethyl, hydroxymethyl, C-formyl, phthalimidomethyl, aryl-substituted imidazolidino, aminohydroxylmethyl, ortho-methylaminobenzenethio, methylphosphonate, methylalkylphosphonate, a nucleoside, a nucleotide, an oligonucleotide, an oligonucleoside, or a hydroxyl-protected or amine-protected derivative thereof.

In certain preferred embodiments of the invention, $L_1$-$L_2$-$L_3$-$L_4$ is $CR_{1a}R_{1b}$-$CR_{2a}R_{2b}$-$CR_{3a}R_{3b}$-$Z_4$, and $Z_4$ is O, S or $NR_4$. In further preferred embodiments of the invention, $L_1$-$L_2$-$L_3$-$L_4$ is $CR_{1a}R_{1a}$-$CR_{2a}R_{2b}$-$Z_3$-$Z_4$, and $Z_3$ and $Z_4$ are, independently, O, S or $NR_4$. In further preferred embodiments of the invention, $L_1$-$L_2$-$L_3$-$L_4$ is $CR_{1a}R_{1b}$-$Z_2$-$CR_{3a}R_{3b}$-$Z_4$, and $Z_2$ and $Z_4$ are, independently, O, S or $NR_4$. In further preferred embodiments of the invention, $L_1$-$L_2$-$L_3$-$L_4$ is $Z_1$-$CR_{2a}R_{2b}$-$CR_{3a}R_{3b}$-$Z_4$, and $Z_1$ and $Z_4$ are, independently, O, S or $NR_4$. This preferred embodiments includes compounds wherein $Z_1$ and $Z_4$ are O; and $R_{2a}$, $R_{2b}$, $R_{3a}$ and $R_{3b}$ are H. In further preferred embodiments of the invention, $L_1$-$L_2$-$L_3$-$L_4$ is $CR_{1a}R_{1b}$-$Z_2$-$Z_3$-$Z_4$, and $Z_2$, $Z_3$ and $Z_4$ are, independently, O, S or $NR_4$. In further preferred embodiments of the invention, $L_1$-$L_2$-$L_3$-$L_4$ is $Z_1$-$Z_2$-$CR_{3a}R_{3b}$-$Z_4$, and $Z_1$, $Z_2$ and $Z_4$ are, independently, O, S or $NR_4$. In further preferred embodiments of the invention, $L_1$-$L_2$-$L_3$-$L_4$ is $Z_1$-$CR_{2a}R_{2b}$-$Z_3$-$Z_4$, and $Z_1$, $Z_3$ and $Z_4$ are, independently, O, S or $NR_4$.

In certain preferred embodiments of the invention, $Z_4$ is O, S or $NR_4$; and one of $Z_1$, $Z_2$ or $Z_3$ is $P(=J_1)J_2$ and the other of $Z_1$, $Z_2$ or $Z_3$ are O, S, $NR_4$ or $CH_2$. In a particularly preferred embodiment, $Z_1$ is O or $CH_2$; $Z_4$ is O; one of $Z_2$ or $Z_3$ is $P(=J_1)J_2$ and the other of $Z_2$ or $Z_3$ is O or $CH_2$; and $J_1$ and $J_2$ are O or S.

In certain preferred embodiments of the invention $L_1$-$L_2$-$L_3$-$L_4$ includes at least one double bond therein. In these embodiments $L_1$-$L_2$-$L_3$-$L_4$ include at least one of an alkene, imine, hydrazone or oxime linkage within $L_1$-$L_2$-$L_3$-$L_4$. Such linkage are formed by selecting $R_4$ and $R_5$ to be one of an electron pair such that one of $L_1$-$L_2$ or $L_2$-$L_3$ together is an alkene moiety; or one of $L_1$-$L_2$ or $L_2$-$L_3$ or $L_3$-$L_4$ together is an imine moiety; or one of $L_1$-$L_2$-$L_3$ or $L_2$-$L_3$-$L_4$ together is a oxime or hydrazone moiety.

In certain preferred embodiments, two or more of $L_1$, $L_2$, $L_3$ and $L_4$, together with at least two additional carbon or hetero atoms, form a 5 or 6 membered ring. In other preferred embodiments, $L_1$, $L_2$, and $L_3$ are, independently, O, S, $NR_4$, $CH_2$ or $Si(R_6)_2$ with at least one of $L_1$, $L_2$ or $L_3$ being $Si(R_6)_2$ and $L_4$ is O, S, Se or $NR_4$. In other preferred embodiments, at least one of $L_1$, $L_2$, $L_3$ or $L_4$ is Se.

Preferably, Q is O and X is H or OH. Preferably, $R_4$ is H or $C_1$ to $C_{10}$ straight or branched chain alkyl or substituted alkyl. Preferably $R_5$ is $C_1$ to $C_{10}$ straight or branched chain lower alkyl or substituted lower alkyl; $C_2$ to $C_{10}$ straight or branched chain lower alkenyl or substituted lower alkenyl; $C_2$ to $C_{10}$ straight or branched chain lower alkynyl or substituted lower alkynyl; or $C_7$ to $C_{14}$ alkaryl or aralkyl. In an even more preferred embodiments of the invention, $R_4$ and $R_5$ are, independently, H or $C_1$ to $C_{10}$ straight or branched chain lower alkyl or substituted lower alkyl.

Bx preferably is a naturally occurring or synthetic purine or pyrimidine heterocyclic bases, including but not limited to adenine, guanine, cytosine, thymine, uracil, 5-methylcytosine, hypoxanthine or 2-aminoadenine. Other such heterocyclic bases include 2-methylpurine, 2,6-diaminopurine, 6-mercaptopurine, 2,6-dimercaptopurine, 2-amino-6-mercaptopurine, 5-methylcytosine, 4-amino-2-mercaptopyrimidine, 2,4-dimercaptopyrimidine and 5-fluorocytosine.

In preferred embodiments, the macromolecules of the invention include from about 2 to about 50 nucleoside subunits (i.e., n=about 1 to about 49). The macromolecules preferably are included in a pharmaceutically acceptable carrier for therapeutic administration.

The present invention provides methods of modulating the production or activity of a protein in a cell system or an organism comprising contacting the cell system or organism with an oligonucleotide-mimicking macromolecule having structure 1.

The invention also provides methods of treating an organism having a disease characterized by the undesired production of a protein comprising contacting the organism with an oligonucleotide-mimicking macromolecule having structure 1.

In another aspect, the invention provides methods of in vitro assaying a sequence-specific nucleic acid comprising contacting a test solution containing the nucleic acid with an oligonucleotide-mimicking macromolecule having structure 1.

Methods of preparing the macromolecules of the invention also are provided. In certain embodiments, the methods comprise the steps of contacting a first nucleoside or oliognucleoside bearing a leaving group at its 4'-position (as numbered in reference to the numbering of a pentofuranosyl nucleoside) with a second nucleoside or oligonucleoside bearing a nucleophile at its 3'-position to form a linkage having formula $L_1$-$L_2$-$L_3$-$L_4$. In other preferred embodiments, the methods comprise the steps of contacting a first xylo nucleoside or oliognucleoside having a xylo nucleoside bearing a leaving group at its 3'-position, with a second nucleoside or oligonucleoside bearing a nucleophile at its 4'-position (as numbered in reference to the numbering of a pentofuranosyl nucleoside) to form a linkage having formula $L_1$-$L_2$-$L_3$-$L_4$. In additional preferred embodiments, the methods comprise the steps of contacting a first nucleoside or oligonucleoside bearing at least a portion but not all of the $L_1$-$L_2$-$L_3$-$L_4$ linker at its 3' position with a second nucleoside or oligonucleoside bearing the remainder of the $L_1$-$L_2$-$L_3$-$L_4$ linker at its 4' position (as numbered in reference to the numbering of a pentofuranosyl nucleoside) to join said nucleosides or oligonucleosides by the $L_1$-$L_2$-$L_3$-$L_4$ linker.

DETAILED DESCRIPTION OF THE INVENTION

Figure 1:
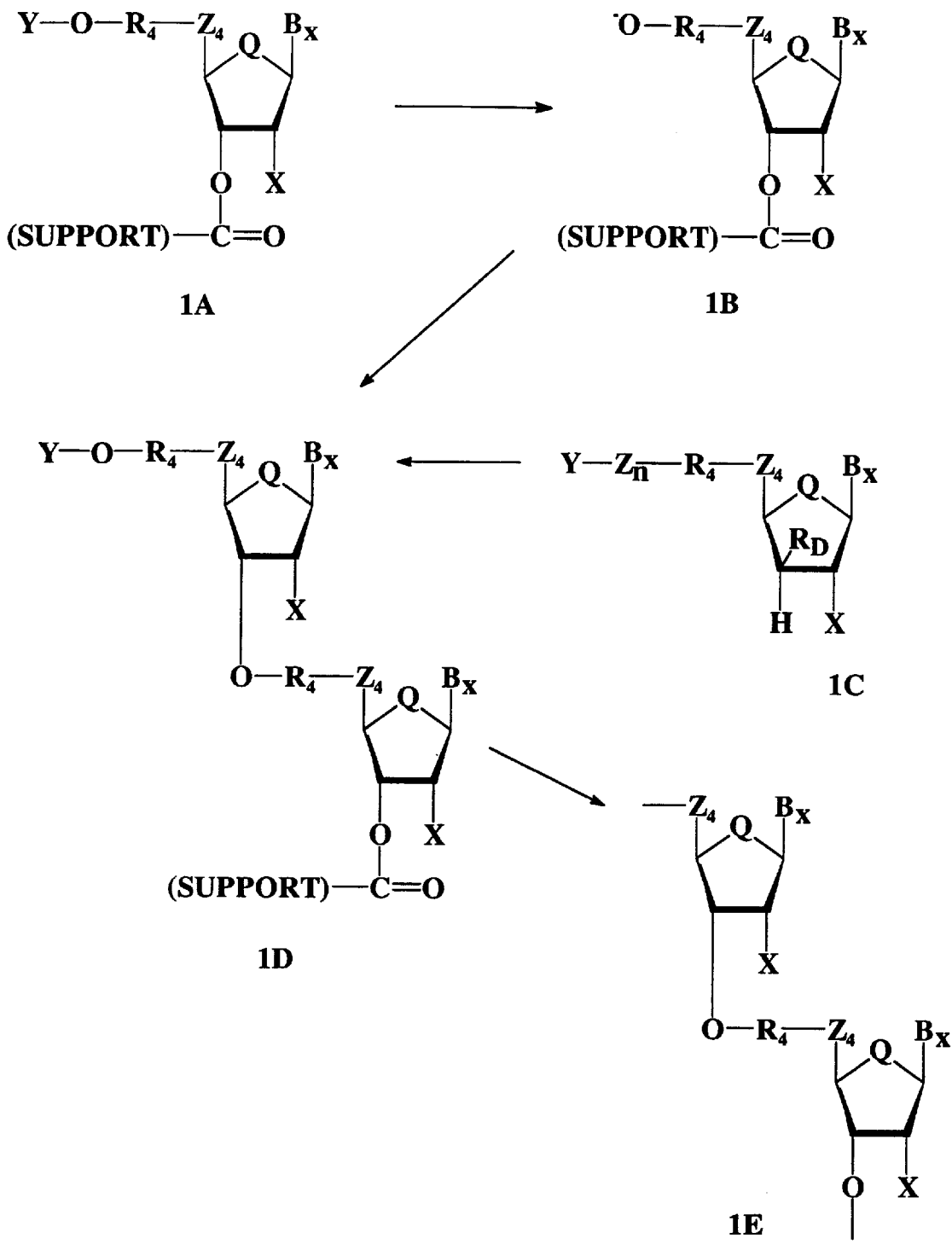
FIGS. 1A and 1B show a preferred iterative synthetic scheme according to the invention.

The term "nucleoside" refers to a unit composed of a heterocyclic base and a sugar, generally a pentose sugar. In naturally occurring nucleosides, the heterocyclic base typically is guanine, adenine, cytosine, thymine or uracil. In naturally occurring nucleosides, the sugar is normally deoxyribose, i.e., erythro-pentofuranosyl, or ribose, i.e., ribopentofuranosyl. Synthetic sugars also are known, including arabino, xylo or lyxo pentofuranosyl sugars and hexose sugars. Throughout this specification, reference to the sugar portion of a nucleoside or other nucleic acid species shall be understood to refer to either a true sugar or to a species replacing the pentofuranosyl or 2'-deoxypentofuranosyl sugar moieties of wild type nucleic acids. Additionally, reference to the heterocyclic base portion of a nucleoside or other nucleic acid species shall be understood to refer to either a natural, modified or synthetic base replacing one or more of the traditional base moiety of wild type nucleic acids. Moreover, reference to inter-sugar linkages shall be taken to include moieties serving to join the sugar or sugar substitute moiety together in the fashion of wild type nucleic acids.

The term "nucleotide" refers to a nucleoside having a phosphate group esterified to one of its 2', 3' or 5' sugar hydroxyl groups. The phosphate group normally is a monophosphate, a diphosphate or triphosphate.

The term "oligonucleotide" refers to a plurality of monophosphate nucleotide units that typically are formed in a specific sequence from naturally occurring bases and pentofuranosyl sugars joined by native phosphodiester bonds. A homo-oligonucleotide is formed from nucleotide units having the same heterocyclic base, i.e. poly(A). The term oligonucleotide generally refers to both naturally occurring and synthetic species formed from naturally occurring subunits.

The term "oligonucleotide analog" has been used in various published patent application specifications and other literature to refer to molecular species similarly to oligonucleotides but that have non-naturally occurring portions. This term has been used to identify oligonucleotide-like molecules that have altered sugar moieties, altered base moieties or altered inter-sugar linkages. Thus, the terminology oligonucleotide analog has been used to denote structures having altered inter-sugar linkages including phosphorothioate, methyl phosphonate, phosphotriester or phosphoramidate inter-nucleoside linkages used in place of phosphodiester inter-nucleoside linkages; purine and pyrimidine heterocyclic bases other than guanine, adenine, cytosine, thymine or uracil and sugars having other than the β pentofuranosyl configuration or sugars having substituent groups at their 2' position or substitutions for one or more of the hydrogen atoms. The term "modified oligonucleotide" also has been used in the literature to denote such structures.

"Oligonucleotide mimics" as the term is used in connection with this invention, refers to macromolecular moieties that function similarly to or "mimic" the function of oligonucleotides but have non-naturally occurring inter-sugar linkages. Oligonucleotide mimics thus can have natural or altered or non-naturally occurring sugar moieties and natural or altered or non-naturally occurring base moieties in combination with non-naturally occurring dephospho linkages. Certain dephospho linkages have been reviewed by Uhlmann, E. and Peyman, A., "Oligonucleotide Analogs Containing Dephospho Intermucleoside Linkages" in Methods in Molecular Biology, Chapter 16, Oligonucleotide Synthetic Protocols, S. Agrawal, Ed., The Humana Press, Inc., Totowa, N.J., 1993.

For the purposes of this invention, an oligonucleotide mimic having non-phosphodiester bonds, i.e. an altered inter-sugar linkage, can alternately be considered an "oligonucleoside" or an "oligonucleotide-mimicking macromolecule." The terms oligonucleoside or oligonucleotide-mimicking macromolecule thus refers to a plurality of joined nucleoside units connected by dephospho linkages.

Additionally, the term "oligomers" is intended to encompass oligonucleotides, oligonucleotide analogs, oligonucleosides or oligonucleotide-mimicking macromolecules. Thus, in speaking of "oligomers" reference is made to a series of nucleosides or nucleoside analogs that are joined together via either natural phosphodiester bonds or via other linkages, including the linkages of this invention. In the content of the novel compounds of this invention, generally, the linkage is from the 3' carbon of one nucleoside to the 4' carbon (as numbered in reference to the numbering of a pentofuranosyl sugar as explained in greater detail below) of a second nucleoside. However, the term "oligomer" can also include other linkages such as a 2'→5' linkage or a 3'→5' linkage (both as numbered in reference to the numbering of a pentofuranosyl sugar).

Certain of the nucleoside compounds of the invention as identified in the specification and claims attached hereto, both as free nucleosides and as nucleosidic units of dimeric, trimeric and other higher order structures of the invention, lack a 5' methylene group of conventional pentofuranosyl nucleosides. In one sense these compounds can be considered as 4'-desmethyl pentofuranosyl nucleosides. In these compounds, a hetero atoms occupies the position normally occupied by the 5'-methylene group of a conventional pentofuranosyl nucleoside. In a further stricter IUPAC rule sense, with the 5'-methylene group removed, the "sugar portion" of these nucleosides are no longer named as pentofuranosyl sugars but are named as tetrahydrofuranyl moieties. In naming these compounds according to IUPAC rules, for identifying the structural positions of the compound, established hierarchical or priority nomenclature rules are followed. In dimeric, trimeric and other higher ordered structures, the linkage to the adjacent nucleoside takes priority over that of the heterocyclic base of the nucleoside. In such dimeric, trimeric and other higher ordered structures the tetrahydrofuranyl ring is number counterclockwise and the position occupied by the hetero atom (in what would be the 5' position of a conventional nucleoside) is identified as the 2 position. If the compound is a tetrahydrofuranosyl nucleoside that is not a part of a dimeric, trimer or other higher ordered structure, the heterocyclic base takes priority and the ring is numbered clockwise with the position occupied by the nucleobase being the 2 position. However, in identifying certain of the protons in the NMR spectra, convention pentofuranosyl nucleoside numbering has been used (except where otherwise noted) for the tetrahydrofuranyl nucleosides.

For the purposes of this specification and the claims appended hereto, when an oligomeric structure of the invention is being considered not as to it individual constituent parts named according to strict naming rules but in a global sense, even when the nucleosides that occupy the ends of the oligomer are tetrahydrofuranyl type nucleoside of the invention, the ends of this structure are referenced in the same manner as for conventional oligonucleotides. Thus they are identified either as a 3' end or a 5' end. In other instances where analogy to convention pentofuranosyl nucleosides is made, strict IUPAC naming rules are deviated from and the numbering system of the conventional pentofuranosyl nucleosides is maintained. In these instances it is more convenient to consider certain tetrahydrofuranyl compounds more as 4'-desmethyl pentofuranosyl compounds and thus attachment is noted as being at a 4' position.

Alkyl groups of the invention include but are not limited to $C_1$–$C_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methyl-pentyl, 3-methylpentyl, 2-ethylhexyl and 2-propylpentyl. Alkenyl groups include but are not limited to unsaturated moieties derived from the above alkyl groups including but not limited to vinyl, allyl and crotyl. Alkynyl groups include unsaturated moieties having at least one triple bond that are derived from the above alkyl groups including but are not limited to ethynyl and propargyl. Aryl groups include but are not limited to phenyl, tolyl, benzyl, naphthyl, anthracyl, phenanthryl, pyrenyl, and xylyl. Halogens include fluorine, chlorine and bromine. Suitable heterocyclic groups include but are not limited to imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Amines are also meant to include polyalkylamino compounds and aminoalkylamines such as aminopropylamine and further heterocycloalkylamines such as imidazol-1, 2 or 4-yl-propylamine.

Substituent groups for the above include but are not limited to other alkyl, haloalkyl, alkenyl, alkynyl, alkoxy, thioalkoxy, haloalkoxy and aryl groups as well as halogen, hydroxyl, amino, azido, carboxy, cyano, nitro, mercapto, sulfides, sulfones, sulfoxides, keto, carboxy, nitrates, nitrites, nitroso, nitrile, trifluoromethyl, O-alkyl, S-alkyl, NH-alkyl, amino, silyl, amides, ester, ethers, carbonates, carbamates, ureas, imidazoles, intercalators, conjugates, polyamines, polyamides, polyethylene glycols, polyethers, groups that enhance the pharmacodynamic properties of oligonucleotides, and groups that enhance the pharmacokinetic properties of oligonucleotides. Other suitable substituent groups also include rhodamines, coumarins, acridones, pyrenes, stilbenes, oxazolo-pyridocarbazoles, anthraquinones, phenanthridines, phenazines, azidobenzenes, psoralens, porphyrins and cholesterols. One particularly preferred group is $CF_3$. Typical intercalators and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine, and iodine. Groups that enhance the pharmacodynamic properties, in the context of this invention, include groups that improve oligonucleotide uptake, enhance oligonucleotide resistance to degradation, and/or strengthen sequence-specific hybridization with RNA. Groups that enhance the pharmacokinetic properties, in the context of this invention, include groups that improve oligonucleotide uptake, distribution, metabolism or excretion.

Antisense therapy is the use of oligonucleotides or other oligomers for the purpose of binding with complementary strands of RNA or DNA. After binding, the oligonucleotide and the RNA or DNA strand can be considered to be "duplexed" together in a manner analogous to native, double stranded DNA. The oligonucleotide strand and the RNA or DNA strand can be considered to be complementary strands in the same context as native double stranded DNA. In such complementary strands, the individual strands are positioned with respect to one another to allow Watson-Crick type hybridization of the heterocyclic bases of one strand to the heterocyclic bases of the opposing strand.

Antisense therapeutics can be practiced in a plethora of organisms ranging from unicellular prokaryotes and eukaryotes to multicellular eukaryotes. Any organism that utilizes DNA-RNA transcription or RNA-protein translation as a fundamental part of its hereditary, metabolic or cellular control is susceptible to antisense therapeutics and/or prophylactics. Seemingly diverse organisms such as bacteria, yeast, protozoa, algae, all plant and all higher animal forms, including warm-blooded animals, can be treated by antisense therapy. Further, since each of the cells of multicellular eukaryotes includes both DNA-RNA transcription and RNA-protein translation as an integral part of their cellular activity, antisense therapeutics and/or diagnostics can also be practiced on such cellular populations. Furthermore, many of the organelles, e.g., mitochondria and chloroplasts, of eukaryotic cells include transcription and translation mechanisms. Thus, single cells, cellular populations or organelles can also be included within the definition of organisms that are capable of being treated with antisense therapeutics or diagnostics. As used herein, therapeutics is meant to include the eradication of a disease state, killing of an organism, e.g., bacterial, protozoan or other infection, or control of erratic or harmful cellular growth or gene expression.

Prior antisense therapy utilizing "oligonucleotide analogs" is exemplified in the disclosures of the following United States and PCT patent applications: Ser. No. 463,358, filed Jan. 11, 1990, entitled Compositions And Methods For Detecting And Modulating RNA Activity; Ser. No. 566,836, filed Aug. 13, 1990, entitled Novel Nucleoside Analogs; Ser. No. 566,977, filed Aug. 13, 1990, entitled Sugar Modified Oligonucleotides That Detect And Modulate Gene Expression; Ser. No. 558,663, filed Jul. 27, 1990, entitled Novel Polyamine Conjugated Oligonucleotides; Ser. No. 558,806, filed Jul. 27, 1991, entitled Nuclease Resistant Pyrimidine Modified Oligonucleotides That Detect And Modulate Gene Expression; Ser. No. 703,619, filed May 21, 1991, entitled Backbone Modified Oligonucleotide Analogs; Ser. No. PCT/US91/00243, filed Jan. 11, 1991, entitled Compositions and Methods For Detecting And Modulating RNA Activity; and patent application PCT/US91/01822, filed Mar. 19, 1991, entitled Reagents and Methods For Modulating Gene Expression Through RNA Mimicry; all assigned to the assignee of this invention. The disclosures of each of the above noted patent applications are herein incorporated by reference.

As set forth in detail in the above-referenced United States and PCT patent applications, oligonucleotides and other oligomers have application in diagnostics, therapeutics, and as research reagents and kits. For therapeutic use, oligonucleotides or other oligomers would be administered to an animal, including humans, suffering from a disease state that is desirous to treat.

This invention is directed to certain macromolecules that function like oligonucleotides yet exhibit other useful properties. As is illustrated in the Examples and Schemes of this specification, the macromolecules are constructed from nucleoside units. These nucleoside units are joined by a linkage of the invention to form dimeric units as illustrated by structure 1 wherein n is 1:

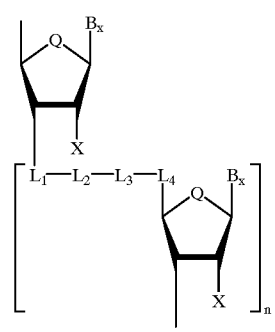

The dimeric units can be further extended to trimeric, tetrameric and other, higher order macromolecules by the addition of further nucleosides (structure 1 wherein n>1). The dimeric units (and/or the higher order units) also can be linked via linkages other than those of the intention, as for instance, via a normal phosphodiester linkage, a phosphorothioate linkage, a phosphoramidate linkage, a phosphotriester linkage, a methyl or other alkylphosphonate linkage, a phosphorodithioate linkage or other linkage.

In certain embodiments, a single linkage is used to join nucleosides to form a macromolecule of the invention. For example, in Scheme I below, m and r are 0, q is 1, n and p are greater than 1, and E is OH. In other embodiments, two or more different linkages are used. For example, in Scheme I, m and r are 0, q is 1, and n and p are greater than 1. In other macromolecules of the invention the nucleoside are joined in groups of two, three or more nucleoside that together form a unit. An activated phosphityl moiety is located at the 3' terminus of this unit and a hydroxyl moiety bearing a removable hydroxyl blocking group is located at the 5' terminus. On subsequent removal of the hydroxyl blocking group and reaction of the hydroxyl group with an activated phosphityl group, the units are then joined together via a normal phosphodiester, phosphorothioate or other phosphorus linkage. Thus, a first unit (a group of two, three or more nucleosides linked together via a first linkage of the invention) and to a second unit (a group of two, three or more nucleosides linked together via the first linkage or via a second linkage of the invention) are connected through a phosphate linkage. The macromolecule is elongated by the addition of further units of nucleosides (linked together via the first, a second or additional linkages of the invention) by joining these additional units to the existing linked units via further phosphorus linkages. As exemplified in Scheme I, in such macromolecules r is 0 or 1, m is a positive number, q is greater than 1, and n and p are positive numbers.

Scheme 1

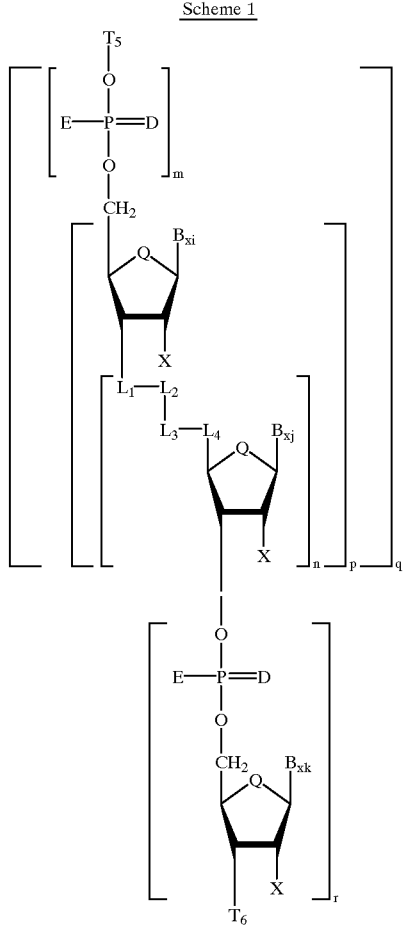

Scheme 1

In accordance with certain methods of the present invention, compounds having structure 1 are prepared by using a first sugar or sugar analog having a 4' nucleophilic substituent (as numbered using the sugar ring numbering of a pentofuranosyl nucleoside) to displace a leaving group from a 3' functionalized second sugar or sugar analog moiety. In preferred embodiments, a nucleoside having a 4' substituent (as numbered using the sugar ring numbering of a pentofuranosyl nucleoside) of structure Y—$Z_n$—$R_A$—$Z_4$— where $R_A$ is a group comprising a one, two, or three carbon backbone (e.g., —$(CH_2)_{1-3}$—) alone or in combination with one or two hetero atoms, Y is a selectively removable protecting group and $Z_n$ is one of $Z_1$ or $Z_2$ as defined above, is removably attached to a solid support. The process further comprises removing the protecting group and reacting the deprotected nucleophilic group with a compound having structure 2:

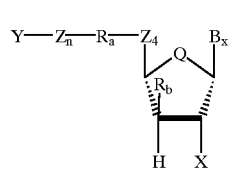

2 where $R_B$ is a leaving group. In accordance with preferred embodiments, the group Y is acid labile and the group $R_B$ is amenable to SN-2 displacement when the 3' carbon of its sugar moiety is attacked by a 4' nucleophile (as numbered using the sugar ring numbering of a pentofuranosyl nucleoside) of a similar moiety. In accordance with other preferred embodiments, $R_A$ can be substituted with one or more ionizable functions, especially amino, hydroxyl, and carboxylate functions. Where the moiety is at the terminus of the desired sequence, Y is any convenient terminating function such as polyamine or a polyethylene glycol. It is preferred that the deprotected hydroxyl group have its nucleophilicity improved by reacting the composition with a suitable base prior to the nucleophilic displacement.

The group Y can include any blocking or protecting group which is selectively removable and which otherwise is consistent with the present invention. It is preferred in some embodiments that Y be acid labile under relatively mild conditions. Thus, tetrahydropyranyl, tert-butyl, bis-(p-methyoxyphenyl)phenylmethyl (DMT) groups can be used. It is preferred that tert-butyl group be employed. Where $Z_n$ is O, for example, protecting group Y can be removed under acidic conditions and the resulting hydroxyl group treated with base to produce a nascent nucleophile. A wide variety of bases can be so employed, including sodium hydride, Grignard reagents, especially methylmagnesium chloride, t-butyl magnesium chloride, lithium diisopropyl amide, methyl lithium, n-butyl lithium and DBU. Anhydrous conditions are generally required. A representative iterative synthetic scheme is shown in FIG. 1. The Y—$Z_n$—$R_A$—$Z_4$— functionality in any given iteration can be the same or different from that selected in prior iterations; indeed, a number of variations may be employed within a single oligonucleoside. Also, further functionality can be provided at the 3' position. Thus, a 3' leaving group, $R_B$, is provided. This leaving group is capable of participating in SN-2 reactions with the nucleophilic species as shown. Exposing the nucleophile of FIG. 1B to the monomer of FIG. 1C results in a nucleophilic displacement reaction with inversion at the 3' position of the monomer. This is depicted in FIG. 1D so as to result in linking of the two sugars or sugar analogs.

The macromolecules of the invention also can be prepared through displacement of a leaving group from the 4' position (as numbered using the sugar ring numbering of a pentofuranosyl nucleoside) of a nucleoside or the 4' terminal position (as numbered using the sugar ring numbering of a pentofuranosyl nucleoside) of an oligonucleoside. In preferred embodiments, the 4'-functionalized moiety (as numbered using the sugar ring numbering of a pentofuranosyl nucleoside) has structure 3:

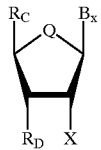

where $R_C$ is a leaving group such as, for example, alkyl and aryl sulfonyl leaving group including p-toluenesulfonyl (tosyl), 4-dimethylaminoazobenzenesulfonyl (dabsyl), 5-dimethylaminonaphthalenesulfonyl (dansyl), trifluoromethylsulfonyl (triflate), methylsulfonyl (mesyl); halogens; o-trichloroacetimidates; 2,4,6-trichlorophenyl; dialkyl phosphite and acyloxy leaving groups including acetoxy, benzoyloxy, p-methoxybenzoyloxy and p-methylbenzoyloxy and other known leaving groups. Acyloxy leaving groups (—$OR_E$ where $R_E$ is C(O)—) are preferred, particularly $OC(O)CH_3$. $R_D$ can be H, hydroxyl, aminomethyl, hydrazinomethyl, hydroxymethyl, C-formyl, phthalimidohydroxymethyl, aryl-substituted imidazolidino, aminohydroxylmethyl, ortho-methylaminobenzenethio, methylphosphonate, methyl-alkylphosphonate, a nucleoside, a nucleotide, an oligonucleotide, an oligonucleoside, or a hydroxyl-protected or amine-protected derivative thereof.

$B_x$ can be a heterocyclic base selected from adenine, guanine, uracil, thymine, cytosine, 2-aminoadenosine or 5-methylcytosine, although other naturally occurring and non-naturally occurring species can be employed. Representative heterocyclic bases are disclosed in U.S. Pat. No. 3,687,808 (Merigan, et al.), which is incorporated herein by reference. It will be recognized that reactive functionality on a base can be chemically protected prior to performance of a given reaction step and then deprotected by methods well known in the art.

Figure 2:
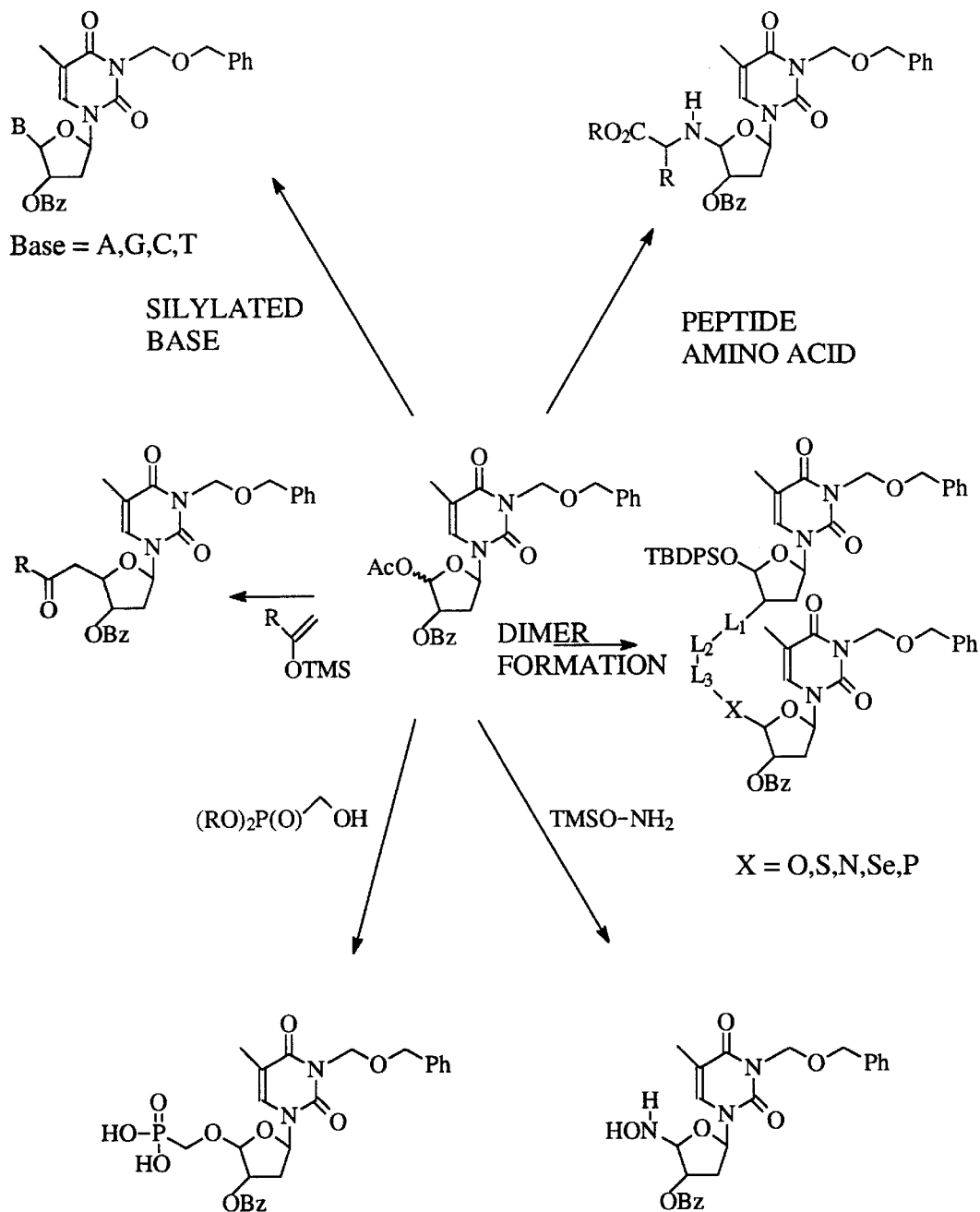
FIG. 2 shows a number of synthetic pathways according to the invention.

Compounds having structure 3 can be used to prepare a wide variety further nucleosides and oligonucleosides. For example, oligonucleosides having structure 1 can be prepared by reacting structure 3 with compounds having structure 4:

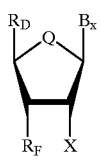

where $R_F$ is, for example, $L_1$-$L_2$-$L_3$-$Z_4$. Other representative nucleosides having structure 4 are shown in FIG. 2.

In some embodiments, the 4'-desmethyl end (as numbered using the sugar ring numbering of a pentofuranosyl nucleoside) may be substituted with polyamines or polyethylene glycols for enhanced oligonucleoside properties as set forth in U.S. Pat. No. 5,138,045, issued Aug. 11, 1992 and incorporated by reference herein.

In accordance with the present invention, methods which are amenable to automated synthetic schemes, especially solid-state support synthetic schemes, are preferred. While a number of methodologies can be employed, one preferred methodology follows. A nucleoside analog is attached to a solid support in any conventional fashion. It is customary, and preferred, to employ a linker to a solid support such as a polymeric carrier at the 3' position. The nucleoside analog moiety does not have a 5' carbon, but rather is substituted in the 4' position with leaving group $R_C$. The nucleoside analog moiety is prepared with any base or base analog, $B_x$ and either a pentofuranosyl moiety, where Q is oxygen, or a cyclopentane moiety where Q is $CH_2$. In certain preferred embodiments of the invention a 2' hydroxyl functionality is present (X is OH) such that the resulting oligonucleoside will have increased hybridization properties with RNA. The 2'-hydroxyl groups can be protected as necessary by means well known to persons of ordinary skill in the art. The only requirement for this group and for its protection is that the same be designed so as to not interfere with substantive reactions in accordance with this invention. In other preferred embodiments, the 2'-hydroxyl group will replaced with other functional groups as for example 2'-alkoxy groups, 2'-alkoxy groups that are substituted with other groups including imidazole and other heterocycle groups, 2'-halogen particularly fluoro.

As will be appreciated by persons of ordinary skill in the art, the synthetic procedures of the invention can be repeated sequentially in order to construct oligonucleosides of any reasonably desired length. A number of monomeric species may be inserted into the chain to incorporate varying bases $B_x$, varying hydroxylic substituents at 2' carbon atoms, and varying linking functions $L_1$-$L_2$-$L_3$-$L_4$. Additionally, the linking functions can be part of a 5 or 6 membered ring. For example, in certain embodiments, $L_2$, $L_3$ and $L_4$ together with 2 or 3 additional carbon- or hetero- atoms can form a heterocycle. Accordingly, it should be appreciated that this reaction scheme is quite general and will likely be appropriate for a variety of substitution schemes.

As will be also appreciated by persons skilled in the art, various ancillary steps may also be taken in furtherance of the present invention. Thus, washing, neutralizing and other reactions or steps may be employed in order to maximize the efficiency and yield of these processes. Additionally, each step may be performed a plurality of times in order to ensure substantial completeness of the addition of each nucleoside subunit. It will be appreciated that a number of other reaction schemes may be employed in order to provide the carbon-atom and hetero-atom backbone (the linking group) between sugars and sugar analogs of nucleic acid species in accordance with the present invention. The term "carbon or heteroatom backbone" as used in the present invention means that there is a chain of carbon and heteroatoms connecting between the 4' position (as numbered using the sugar ring numbering of a pentofuranosyl nucleoside) of one sugar or sugar analog and the 3' position of a second sugar or sugar analog. In preferred embodiments of the invention, this chain is a four atom chain. For this four carbon or heteroatom backbone, there will be a total of four such atoms (the carbon plus the hetero atoms) in the backbone.

In one preferred group of compounds of the invention, the $L_1$-$L_2$-$L_3$-$L_4$ backbone linking the nucleosides of the macromolecules of the invention will include a phosphorus atom at one of the $L_2$, $L_2$ or $L_3$ positions. Particularly preferred are compounds wherein the $L_1$-$L_2$-$L_3$-$L_4$ backbone is of the structure $Z_1$—P(=$Y_1$)$Y_2$—$CH_2$—$Z_4$, $CH_2$—$Z_2$—P(=$Y_1$)$Y_2$—$Z_4$, $Z_1$—$CH_2$—P(=$Y_1$)$Y_2$—$Z_4$, $CH_2$—P(=$Y_1$)$Y_2$—$CH_2$—$Z_4$ or $CH_2$—$CH_2$—P(=$Y_1$)$Y_2$—$Z_4$ where $Z_1$, $Z_2$ and $Z_4$ are O, S, Se or $NR_4$ and $Y_1$ and $Y_2$ are as defined above. Most preferred are $Z_1$, $Z_2$ and $Z_4$=O or S, $Y_1$=O or S, and $Y_2$ is OH, SH, alkyl or alkoxy—particularly $Z_1$, $Z_2$ and $Z_4$=O, $Y_1$=O, and $Y_2$ is OH. By selecting the substituents $Y_1$ and $Y_2$ various phosphate moieties can be formed including phosphodiesters, phosphorothioates, phosphorodithioates, phosphoroselenates, phosphorodiselenates, phosphoramidates, boranophosphates, alkyl phosphonates, phosphotriesters, phosphonates and H-phosphonates.

Figure 3A:
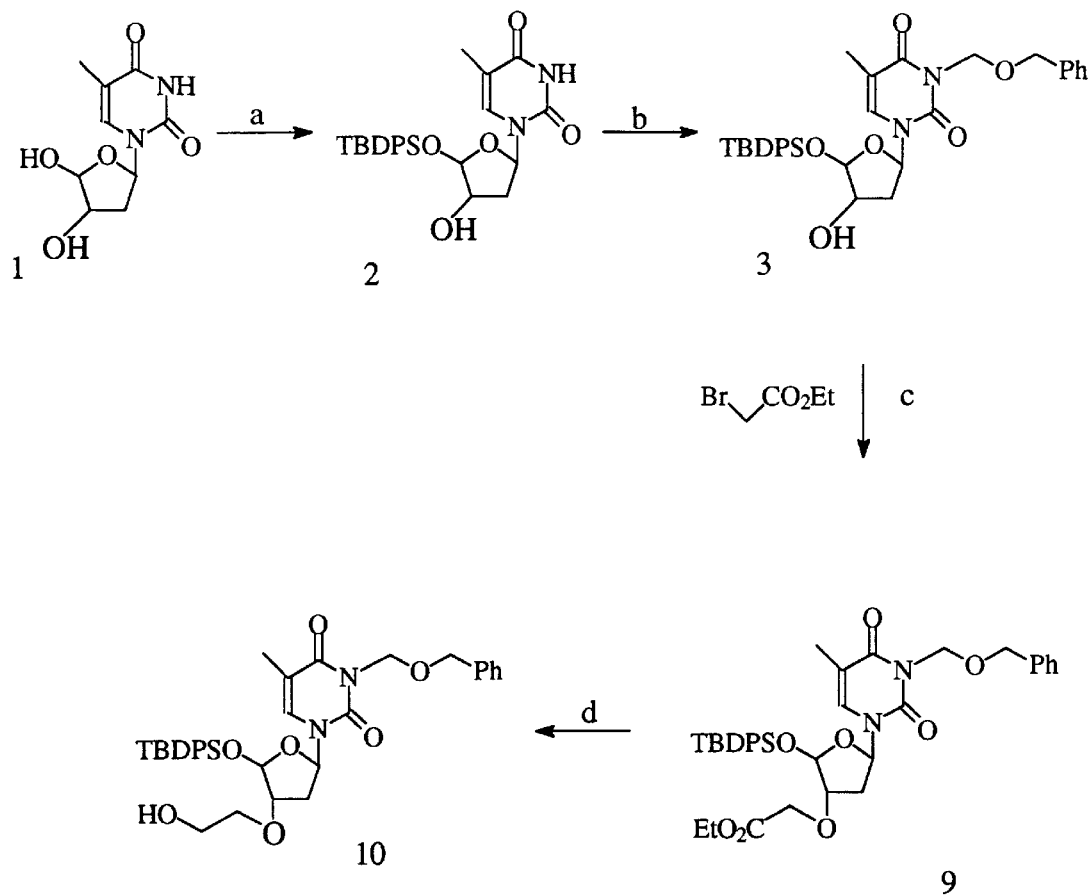
FIGS. 3A and 3B show a representative synthesis of 3'-O-(2-hydroxyethyl) nucleosides and 5'-acetoxy nucleosides.
Figure 3B:
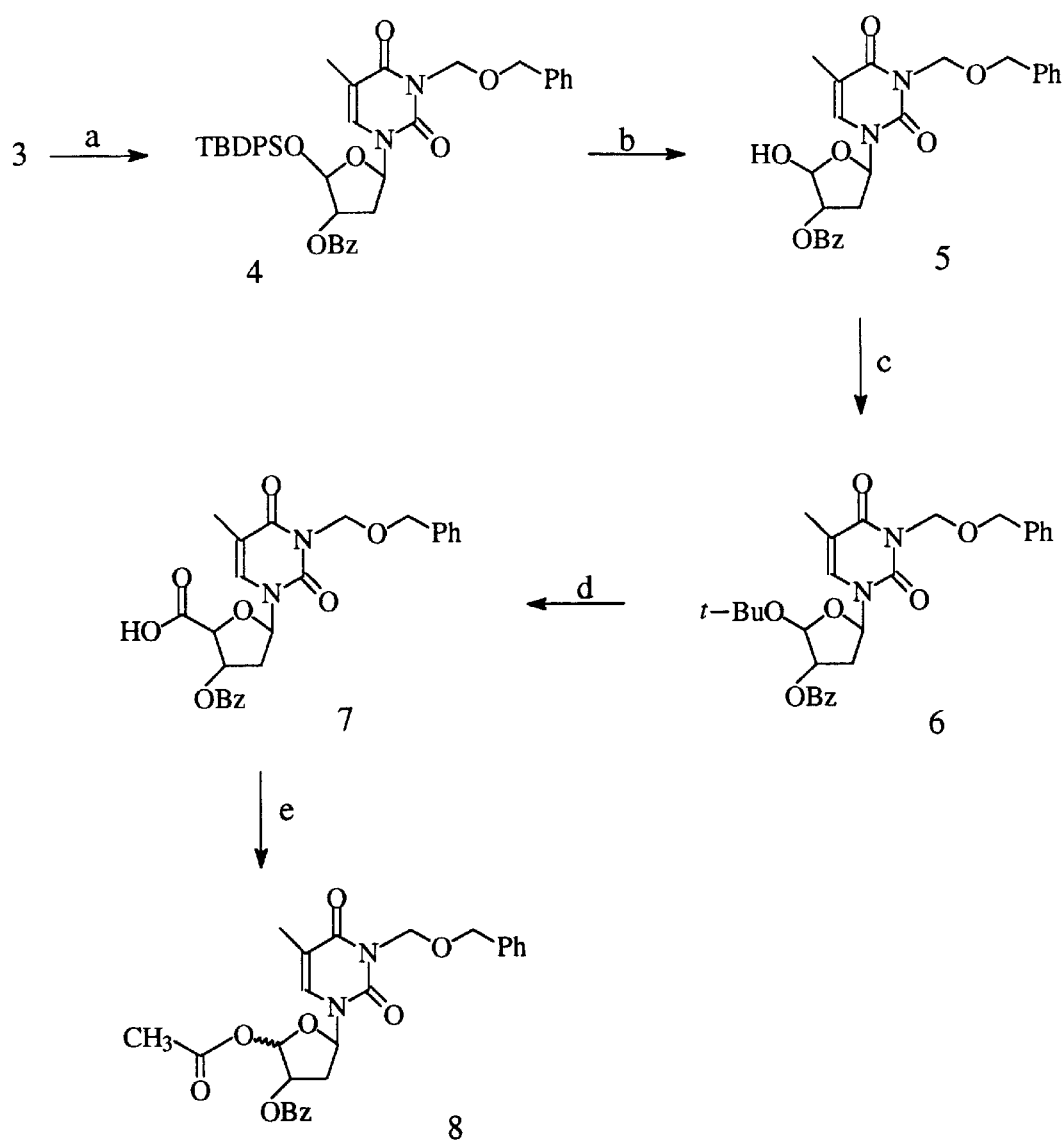

FIG. 3 shows the synthesis of a 3'-O-(2-hydroxyethyl) nucleoside 10 and a 4'-acetoxy nucleoside 8 (as numbered using the sugar ring numbering of a pentofuranosyl nucleoside). A common precursor, 3, was utilized for the synthesis of both 8 and 10. This precursor, nucleoside 3, having blocking groups on both the base and the sugar, is derived from a sugar blocked thymidine, nucleoside 2, that, in turn is, obtained from thymidine. The 3'-O-(2-hydroxyethyl) nucleoside 10 was prepared by generating the 3'-O-ethylacetate derivative 9, which then was hydrolyzed in methanol and sodium borohydride to produce 3'-O-(2-hydroxyethyl) nucleoside 10.

The 4'-acetoxy nucleoside 8 (as numbered using the sugar ring numbering of a pentofuranosyl nucleoside) was prepared by treating 3'-O-benzoyl nucleoside 4 with hydrogen fluoride-pyridine to give the 5' hydroxyl derivative 5, which was oxidized by a modification of the procedure of Corey and Samuelsson, *J. Org. Chem.* 1984, 49, 4735 to provide 5'-tert-butyl carboxylate derivative 6. The 4'-tert-butyl carboxylate 6 was treated with $CF_3COOH$ to provide the free acid derivative 7, which was treated with $Pb(OAc)_4$ and pyridine to provide 4'-acetoxy nucleoside 8 (as numbered using the sugar ring numbering of a pentofuranosyl nucleoside). Use of the 3'-O-benzoyl group allows for acyl group participation during displacement of the 4'-acetoxy group (as numbered using the sugar ring numbering of a pentofuranosyl nucleoside) to give the desired isomer upon completion of the displacement reaction used to effect dimer formation.

Figure 4A:
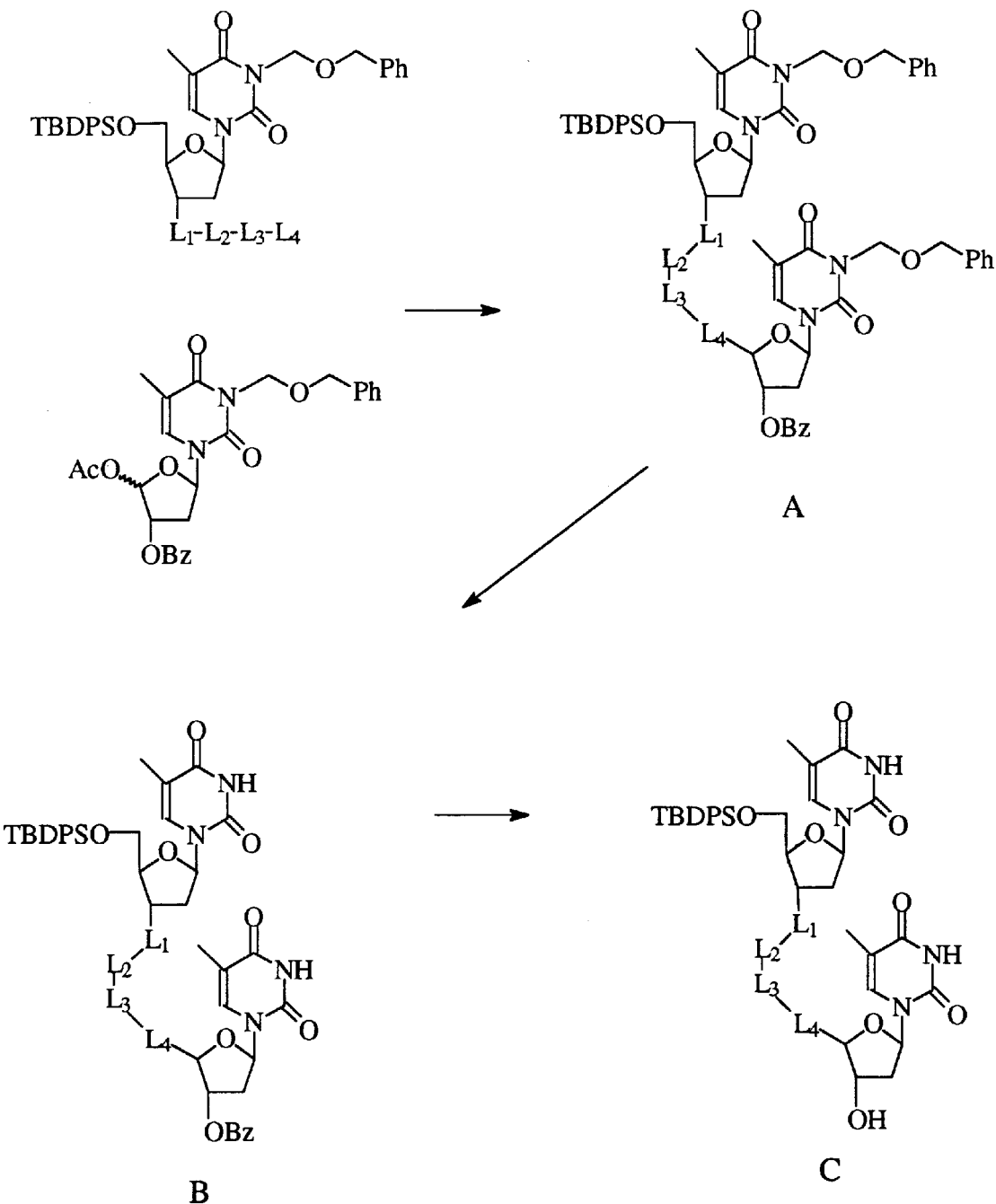
FIGS. 4A and 4B show a representative coupling of 3'-O-(2-hydroxyethyl) nucleosides and 5'-acetoxy nucleosides.
Figure 4B:
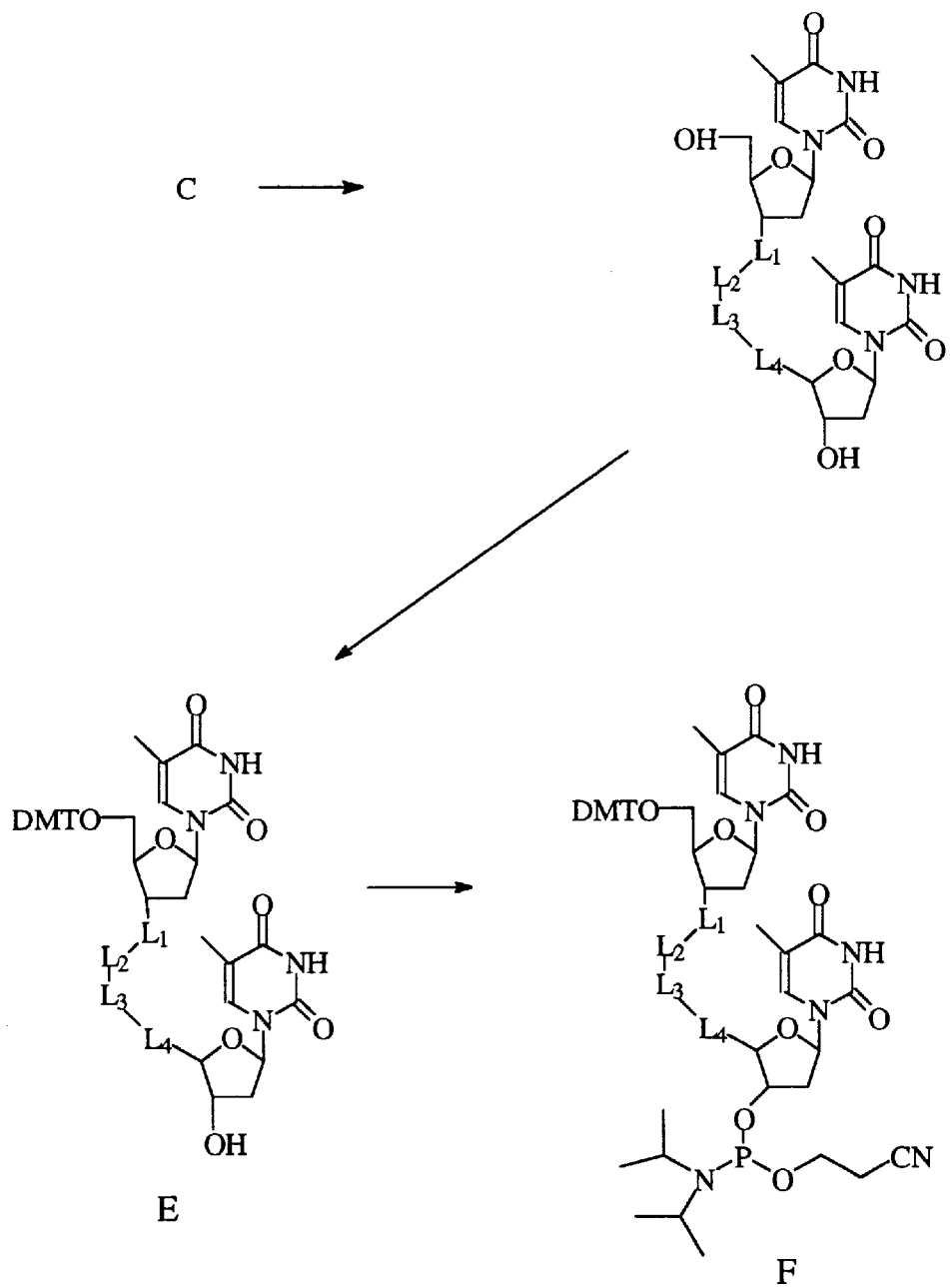
Figure 5:
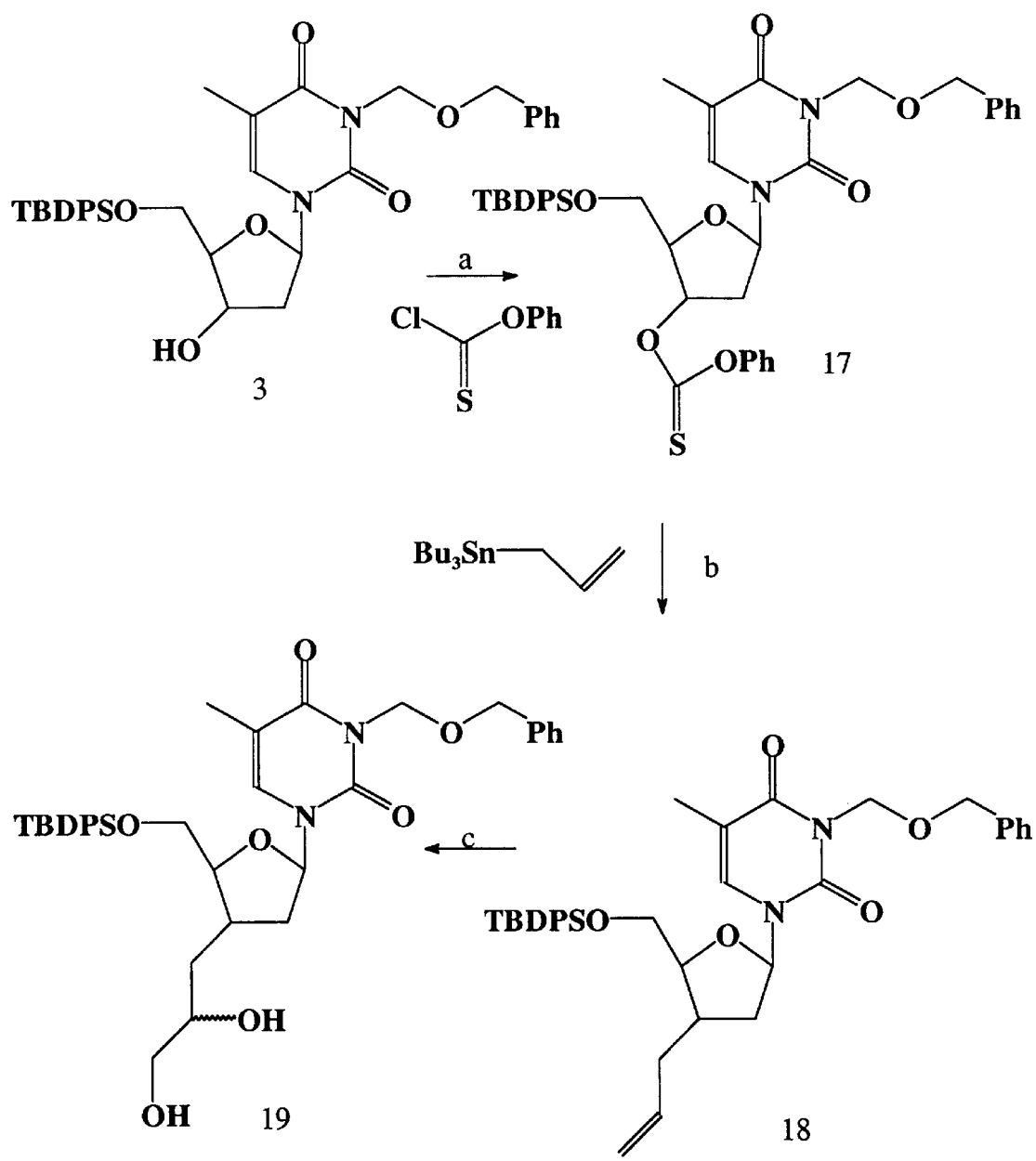
FIGS. 5 to 23 illustrate representative synthetic schemes for the preparation of compounds of the invention.
Figure 6:
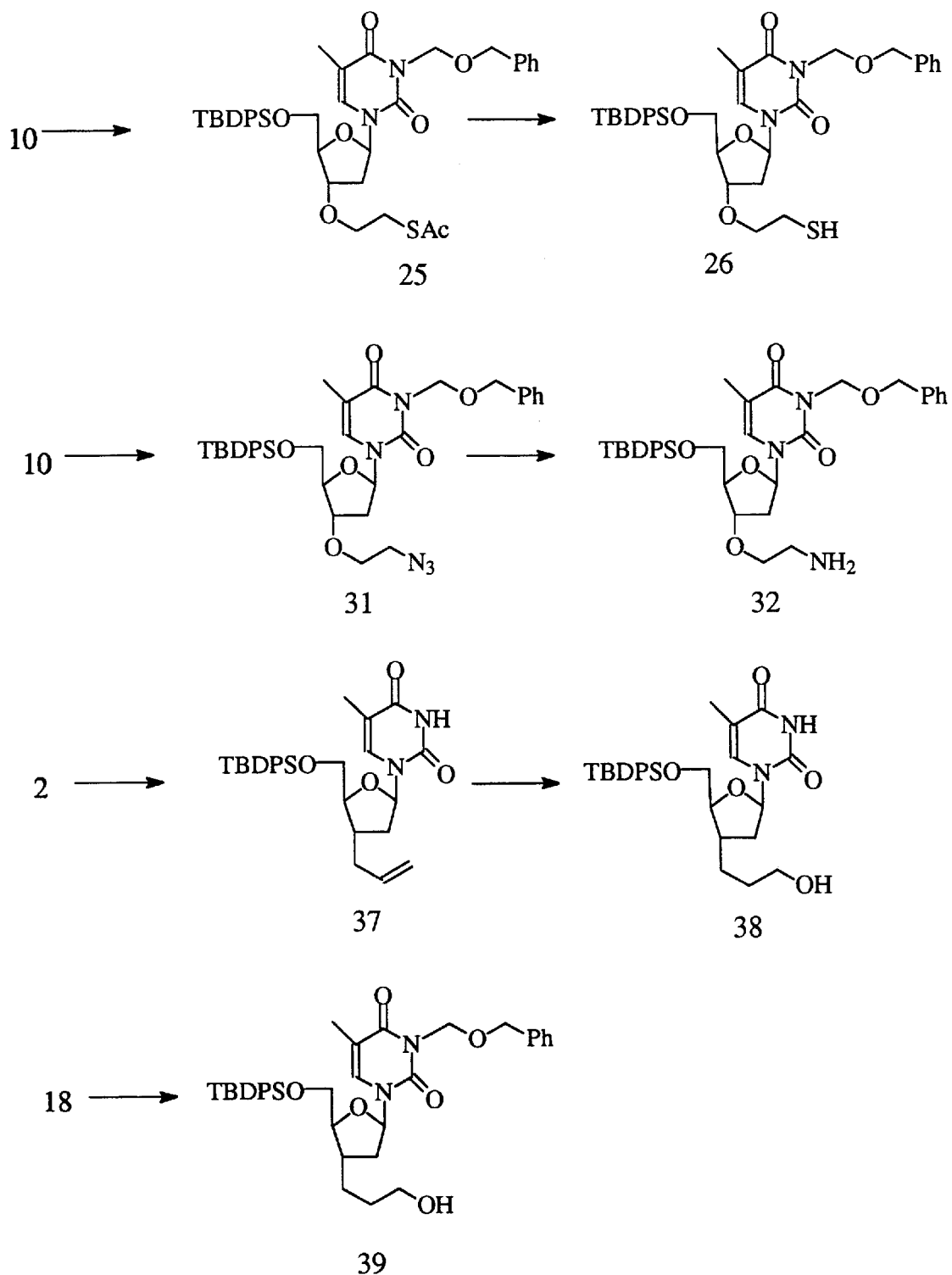
Figure 7:
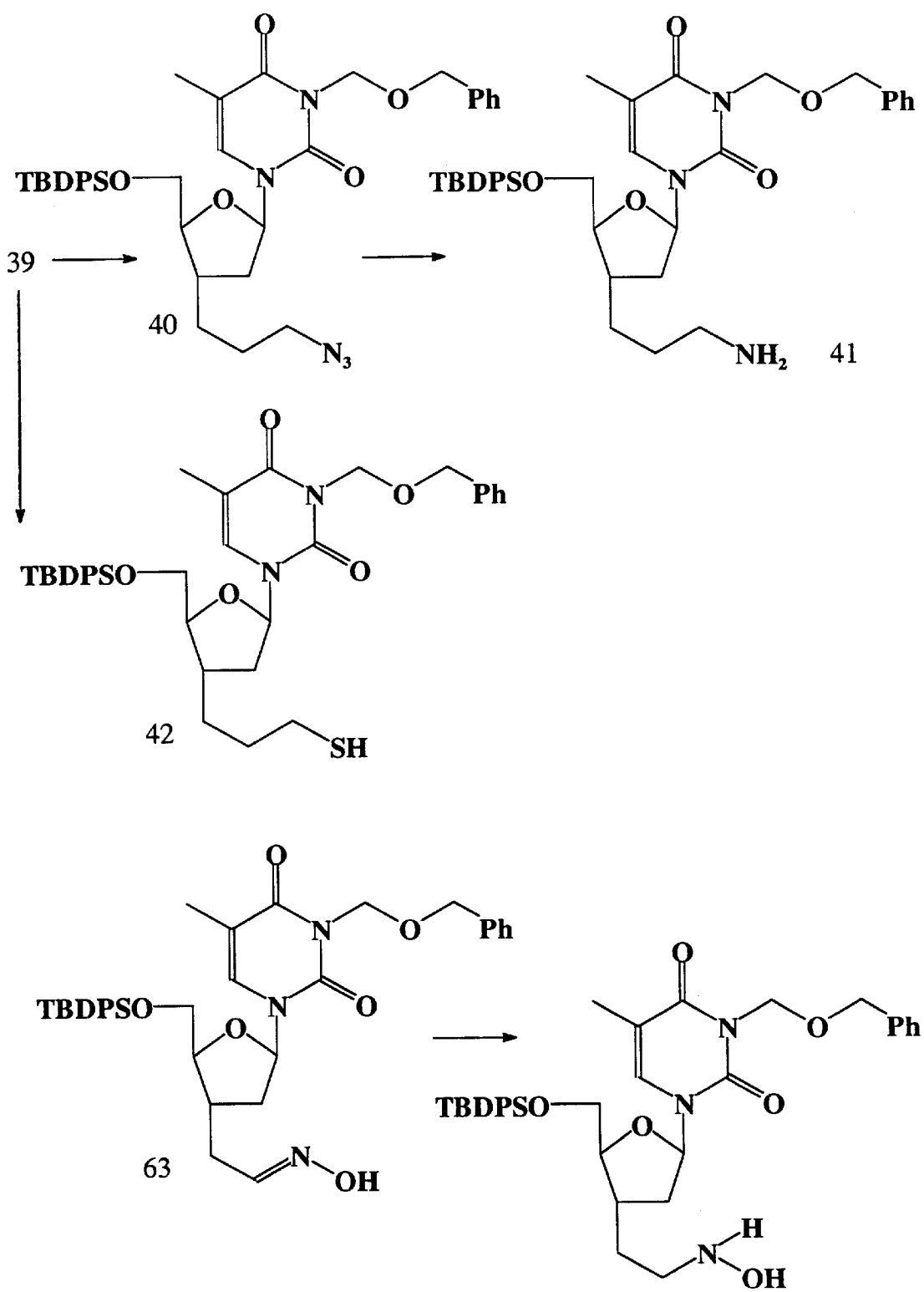
Figure 8:
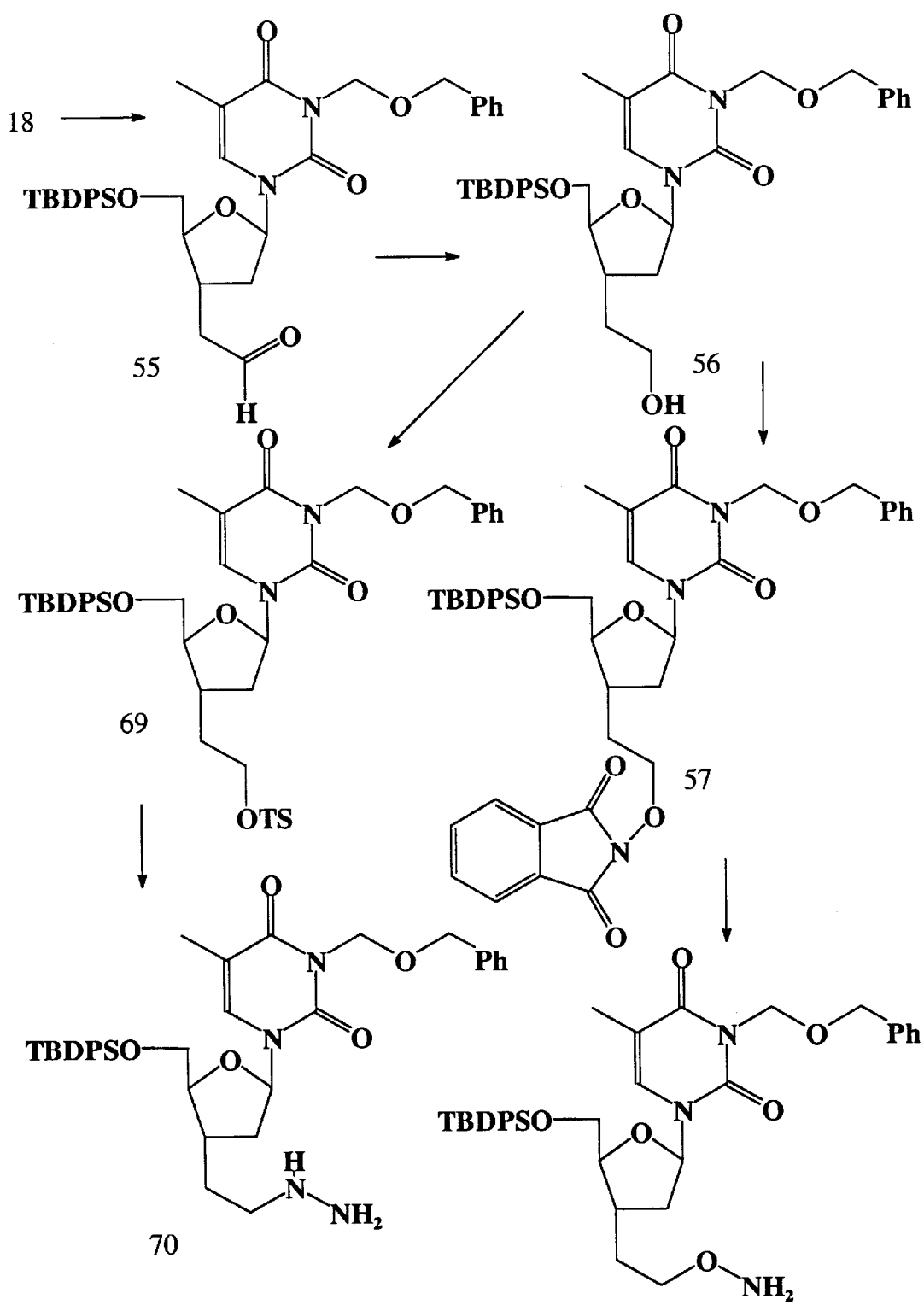
Figure 9:
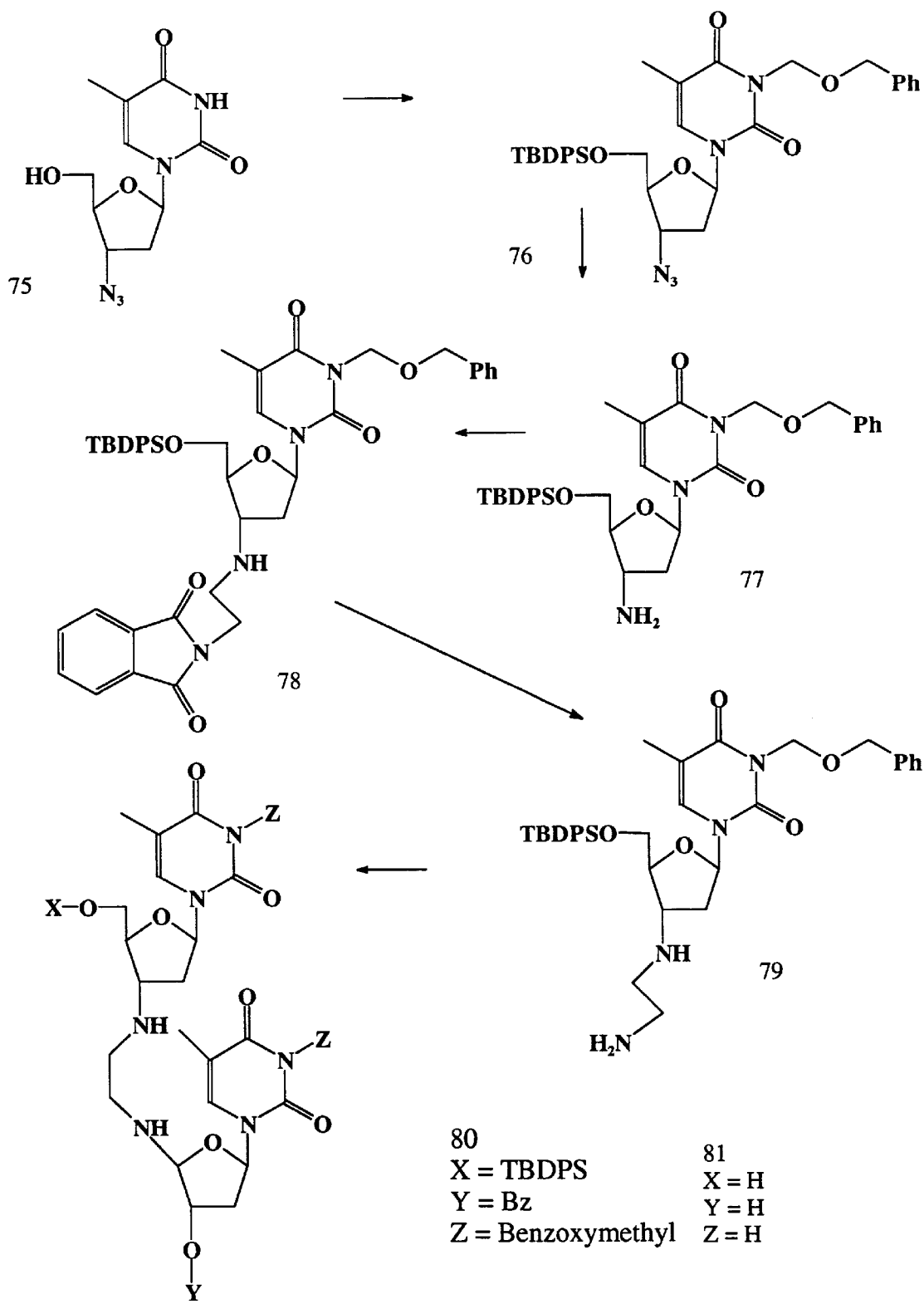
Figure 10:
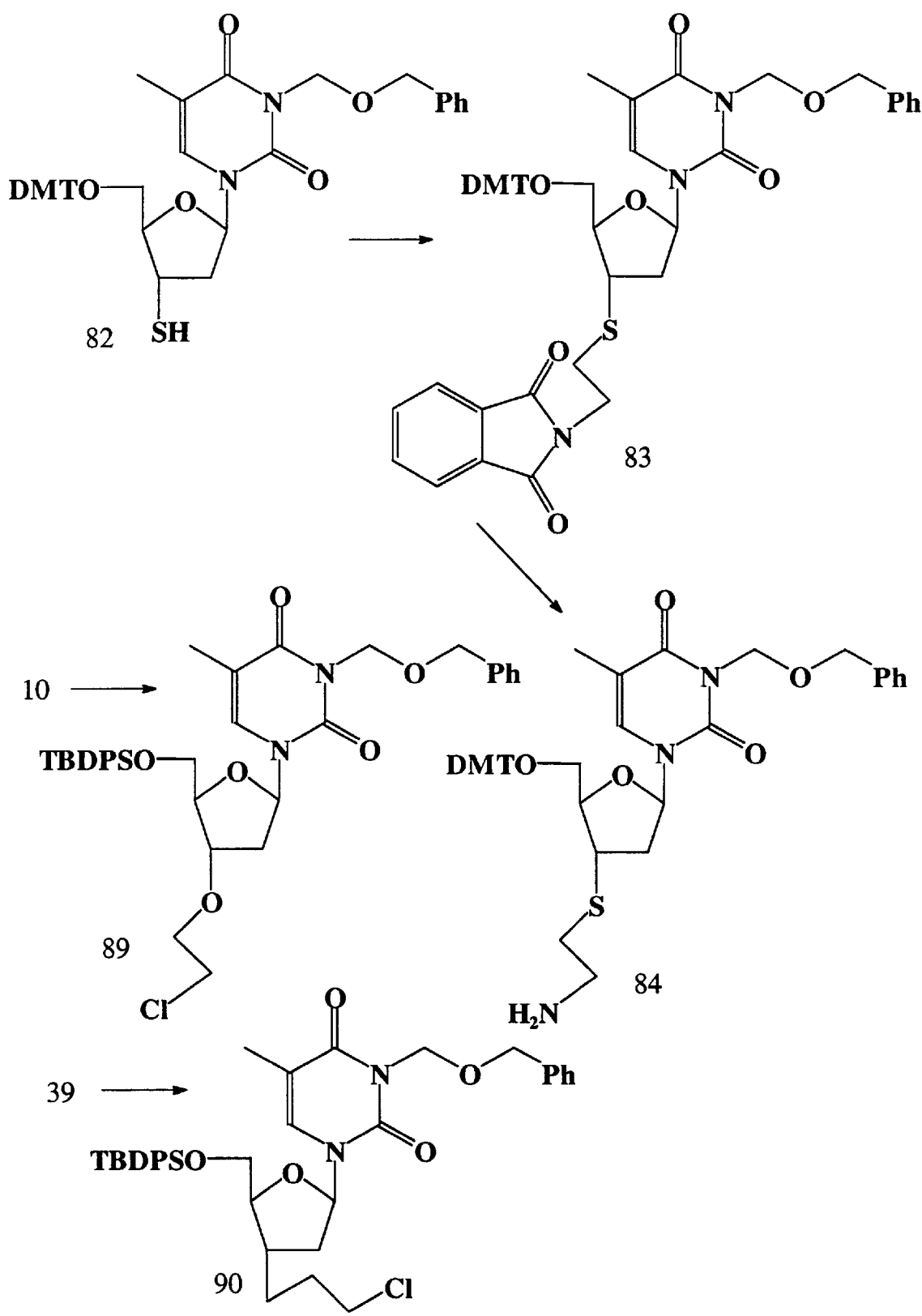
Figure 11:
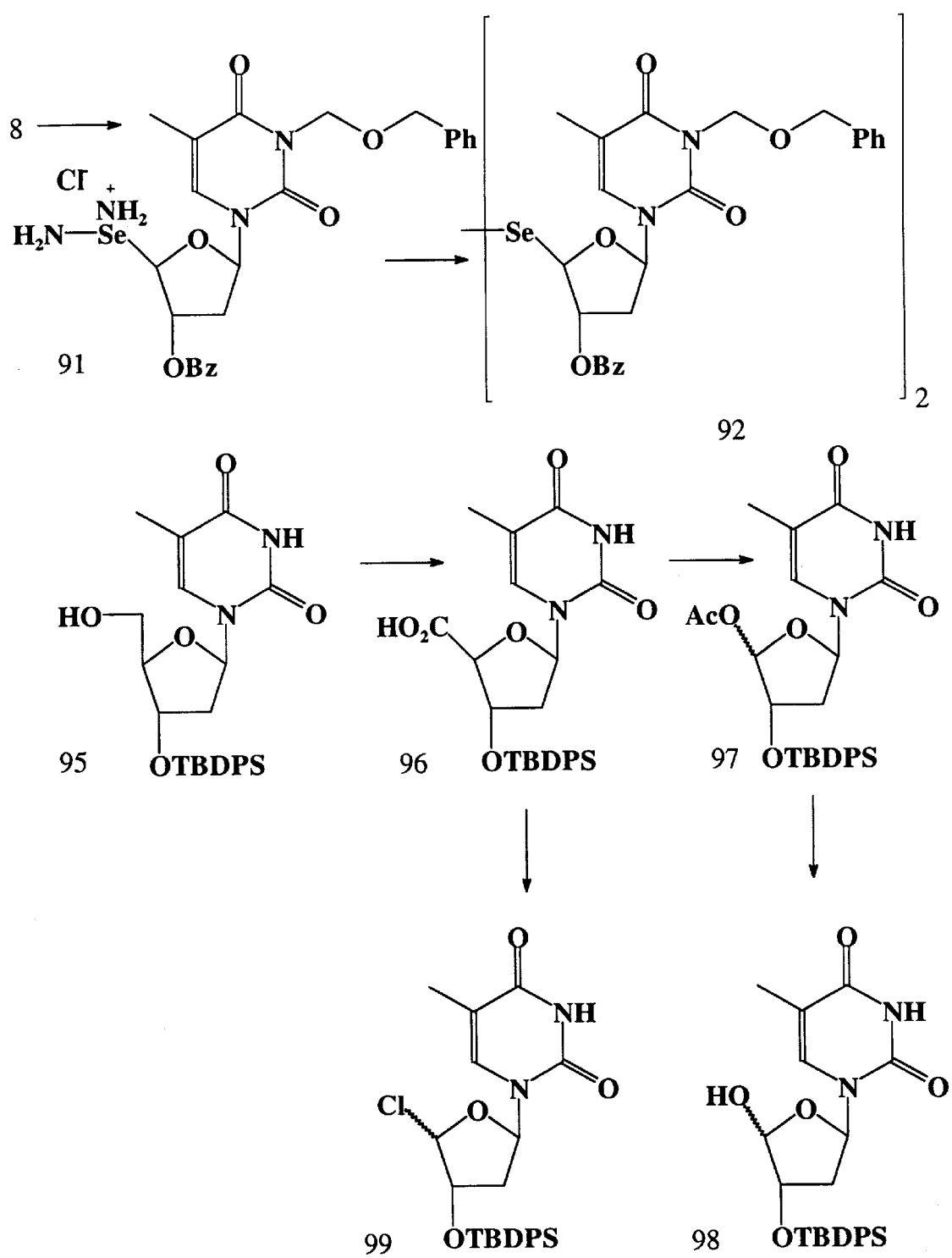
Figure 12:
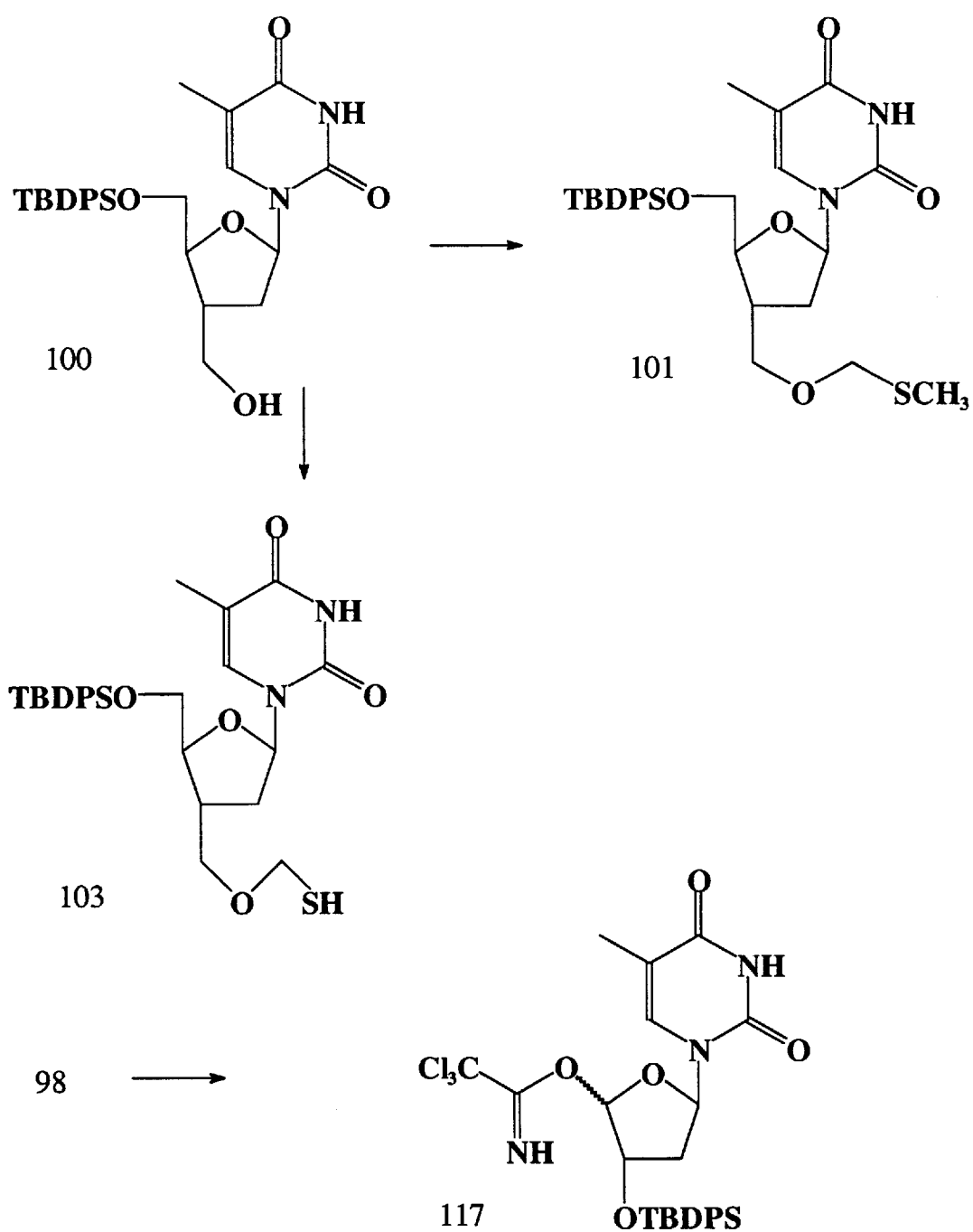
Figure 13:
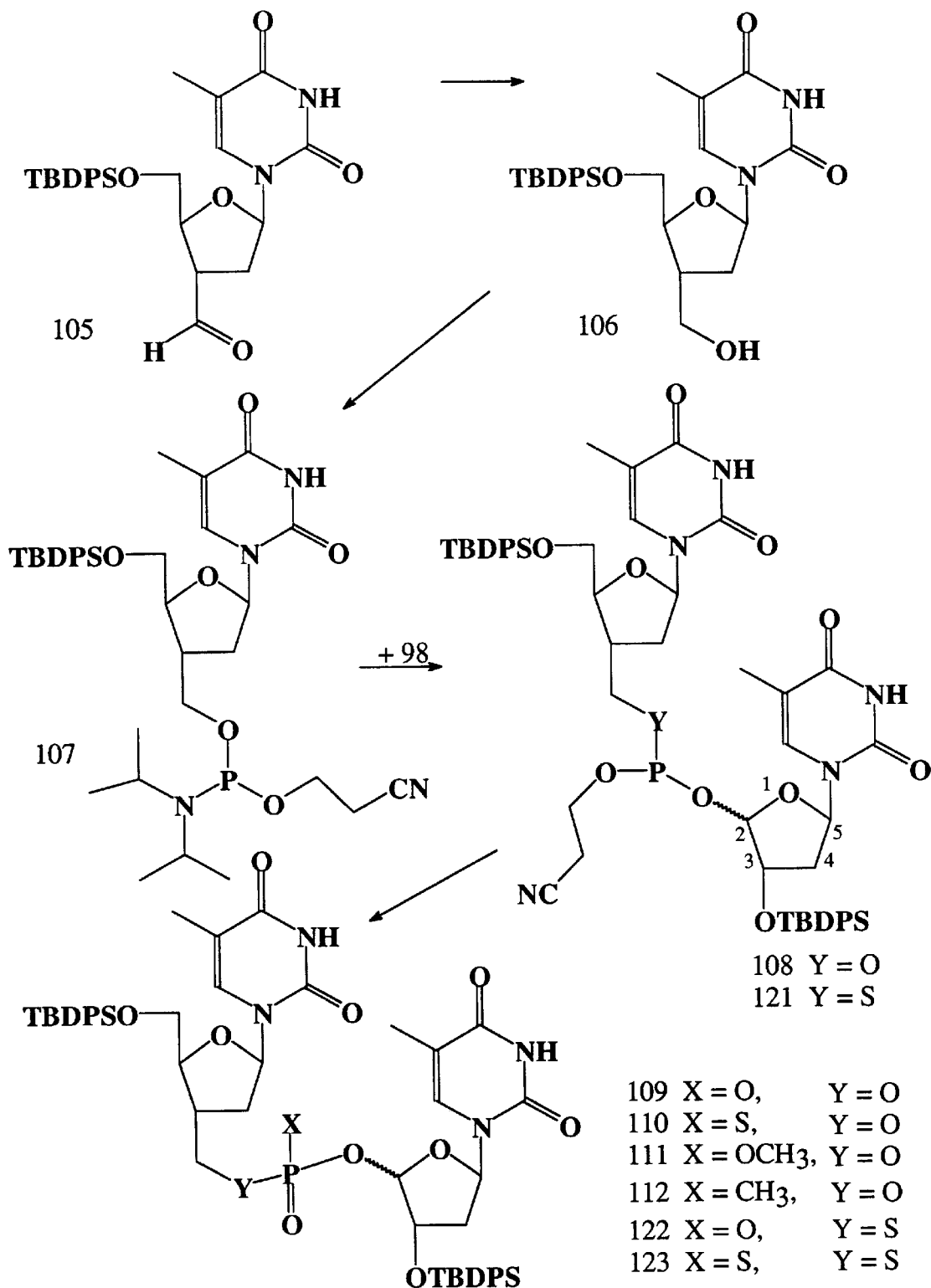
Figure 14:
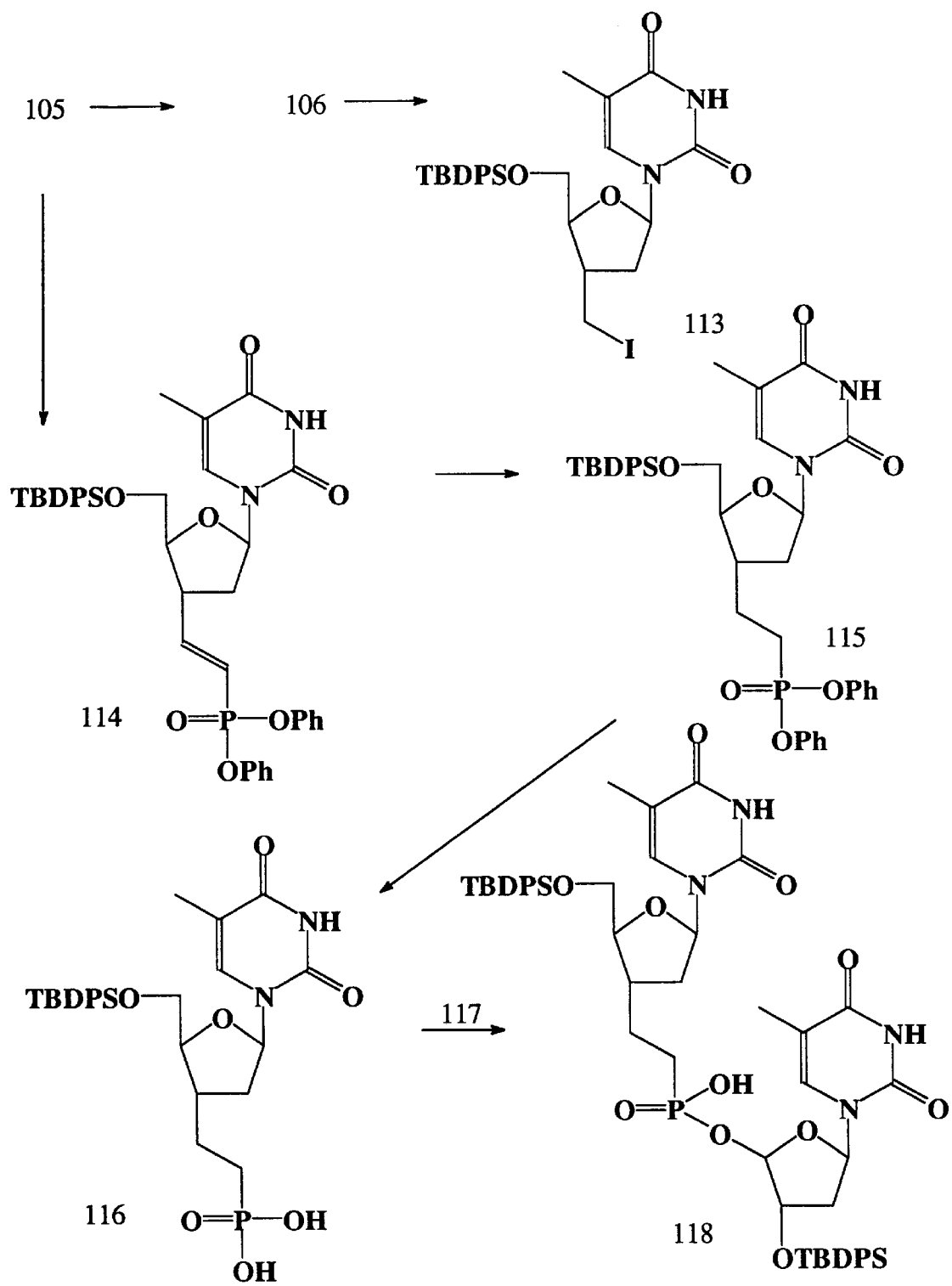
Figure 15:
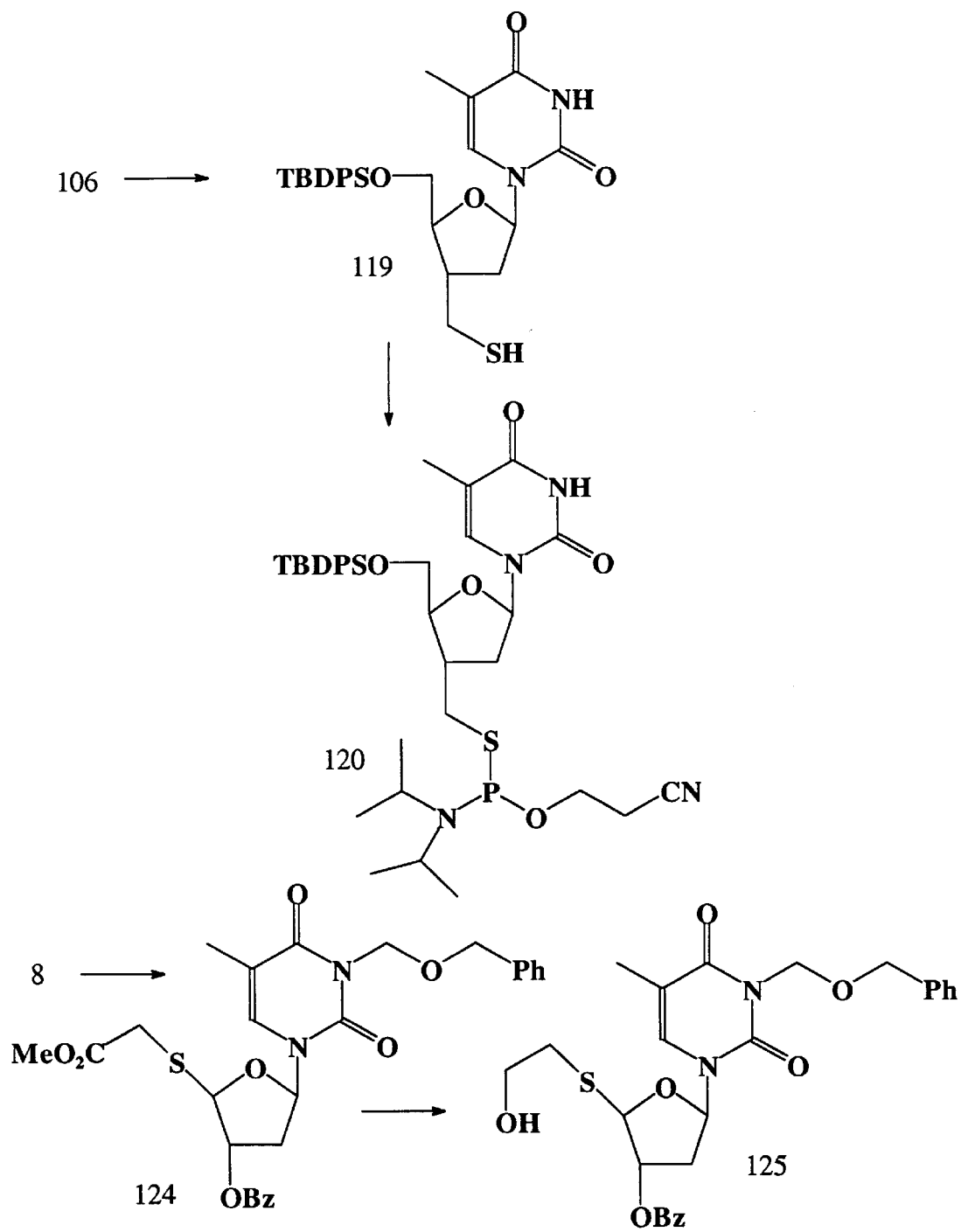
Figure 16:
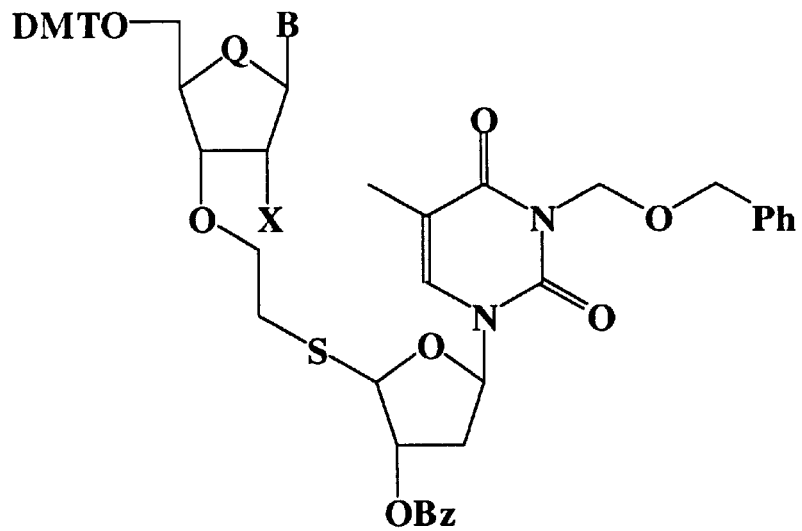
Figure 17:
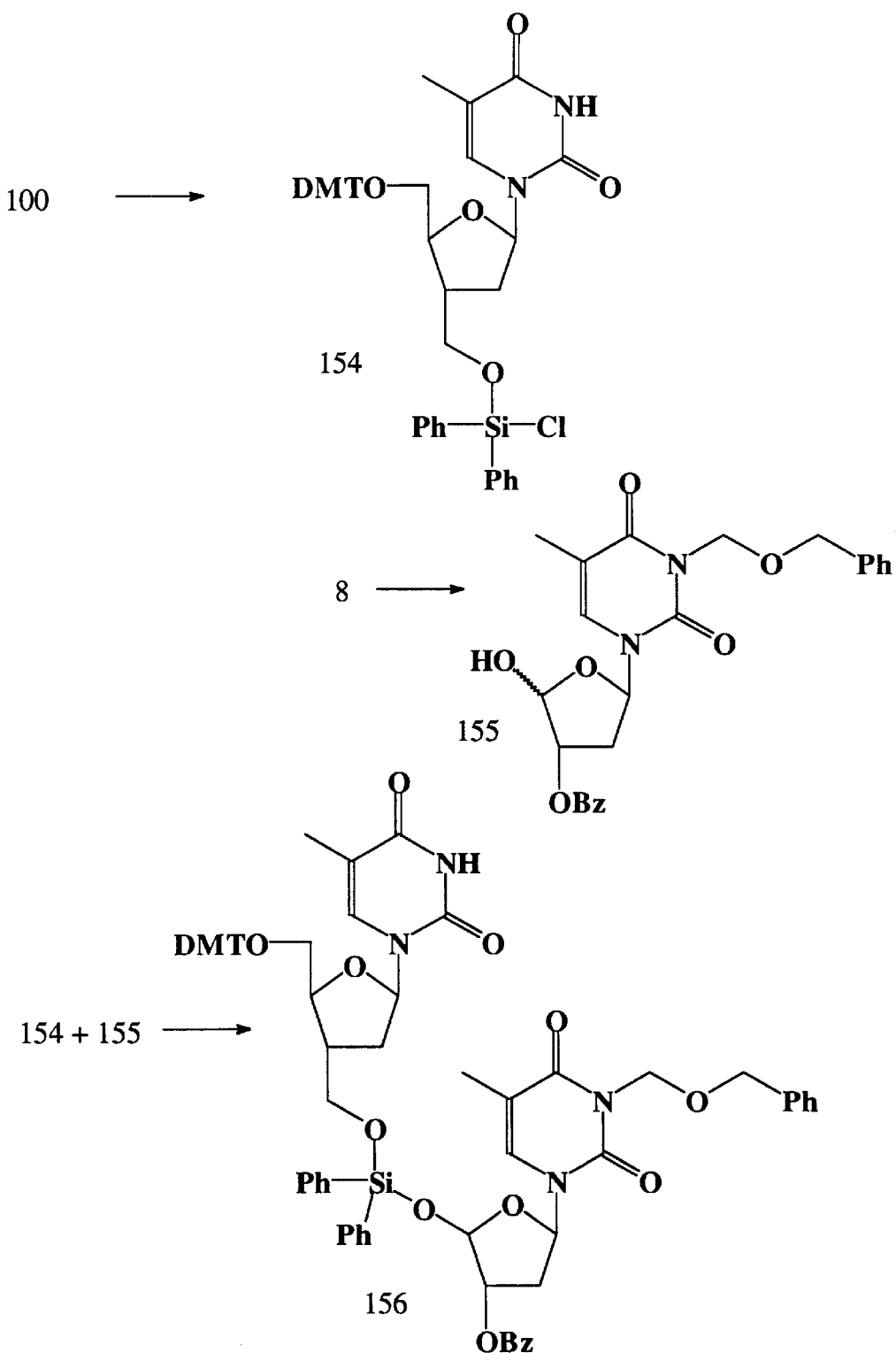
Figure 18:
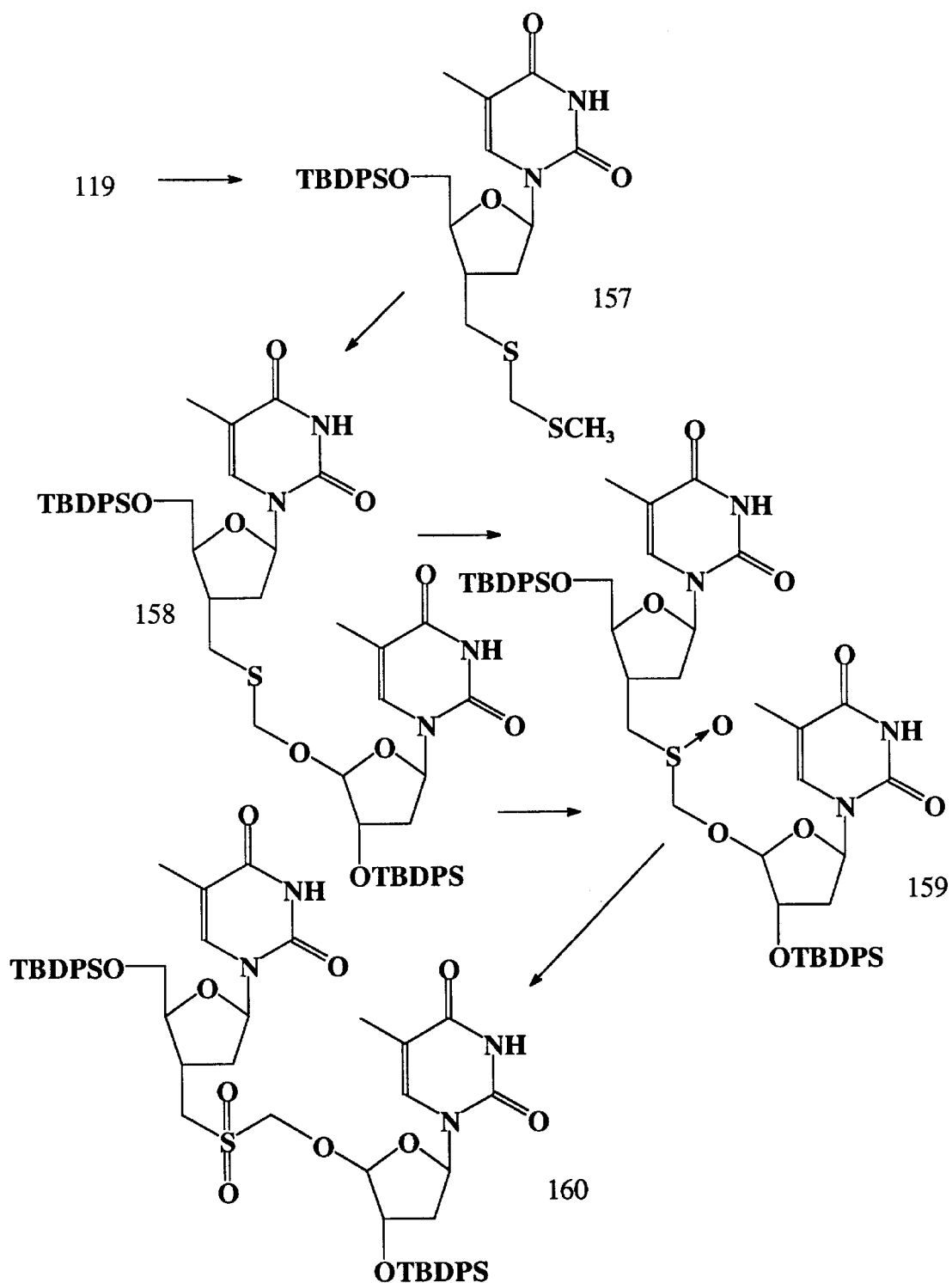
Figure 19:
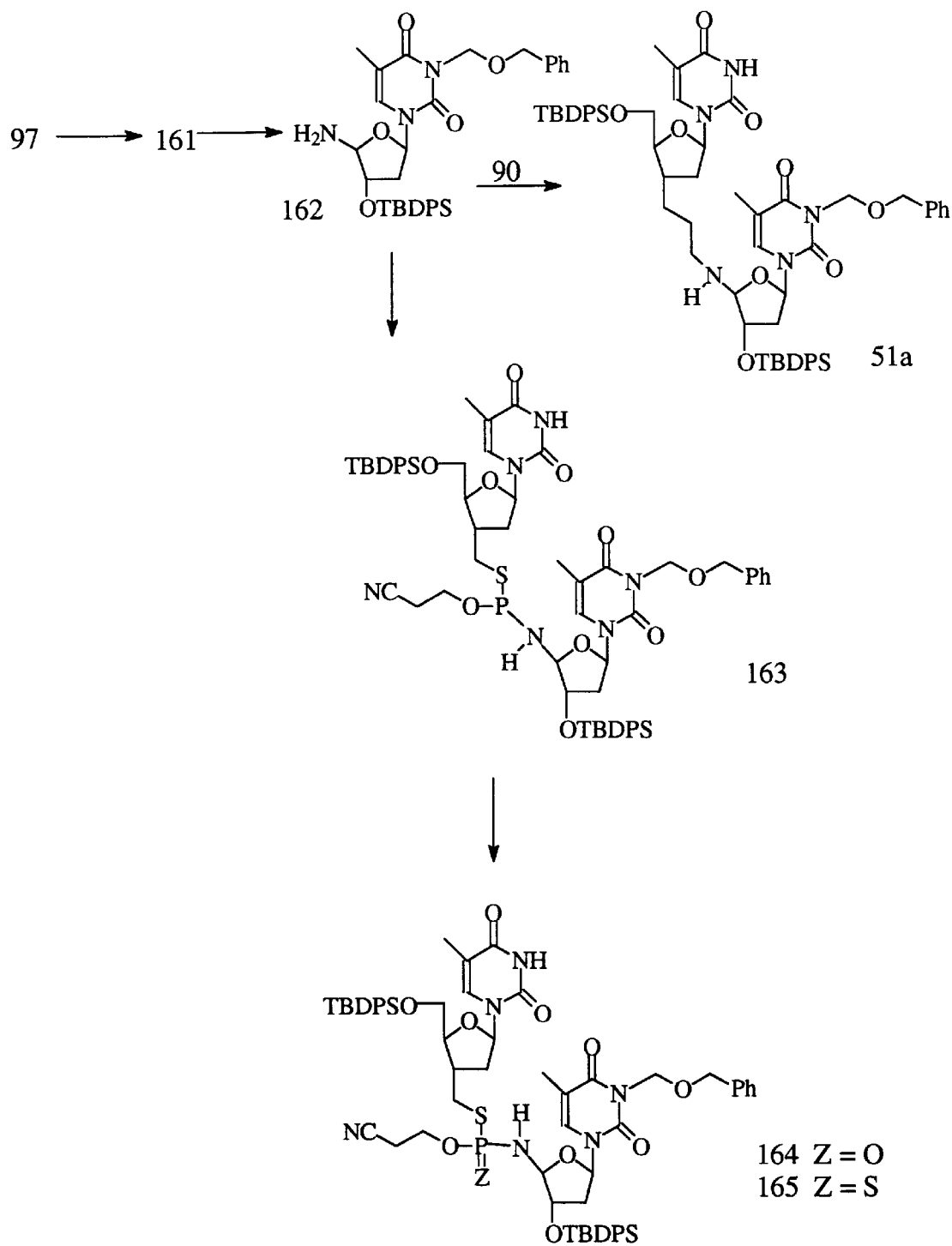
Figure 20:
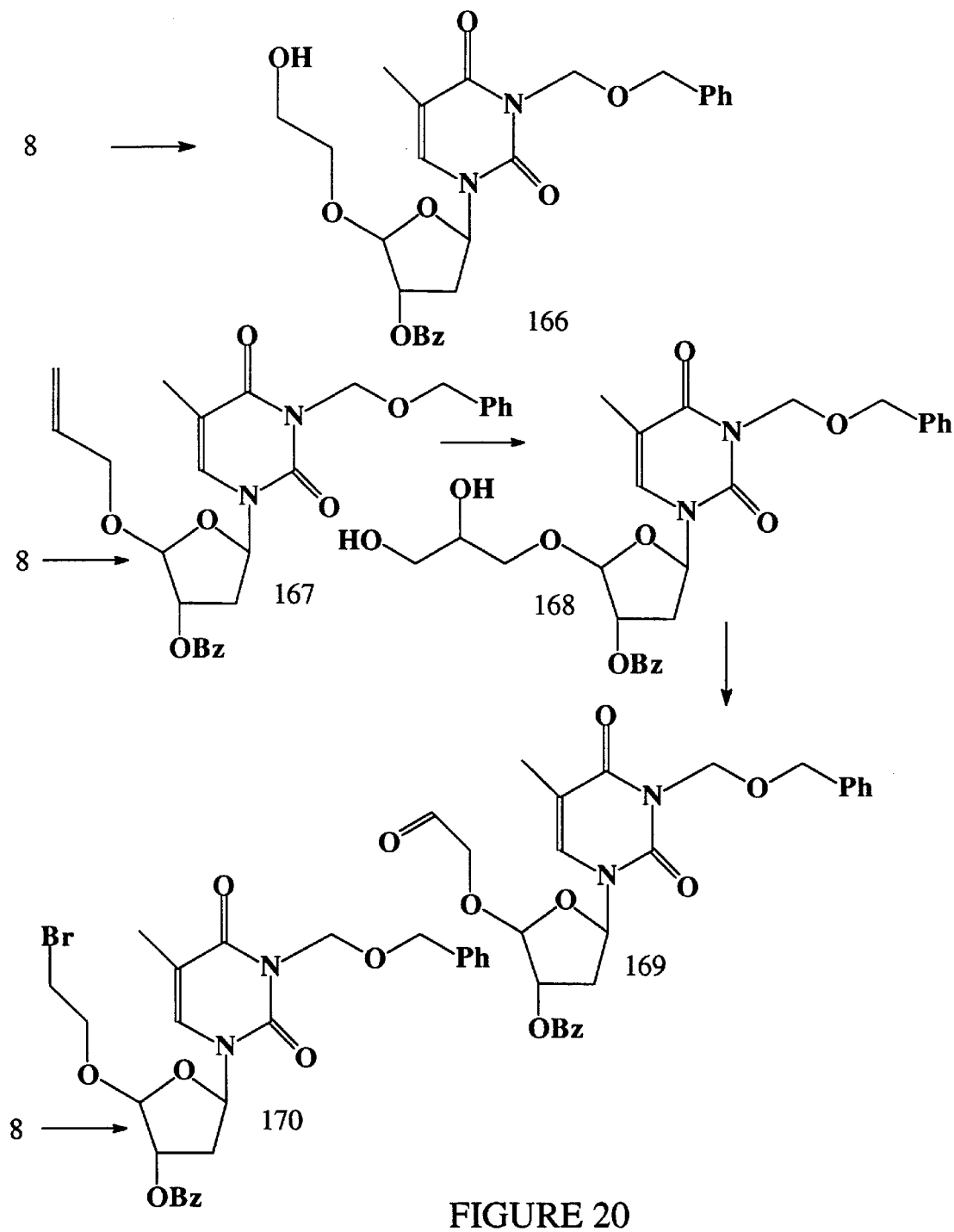
Figure 21:
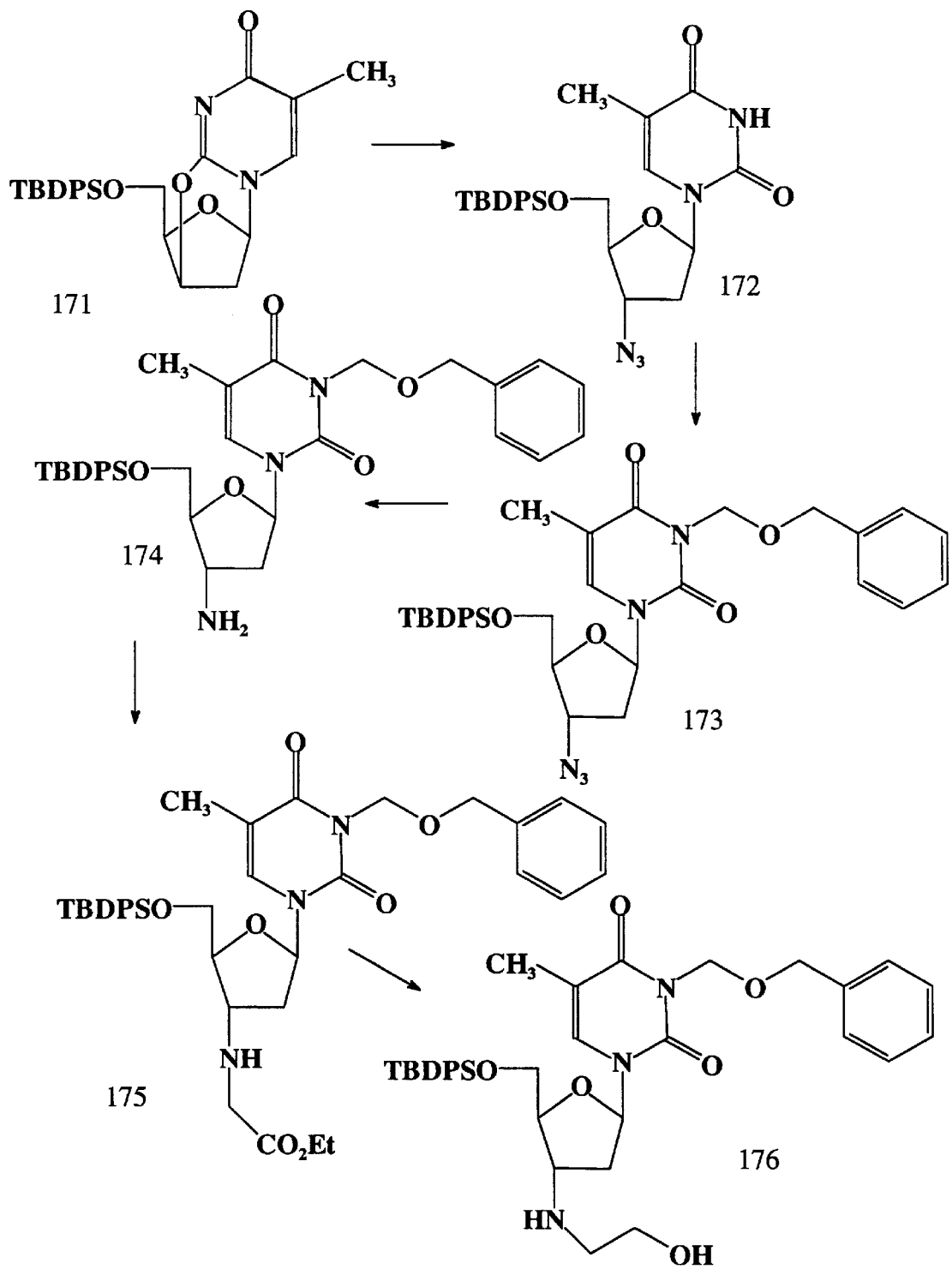
Figure 22:
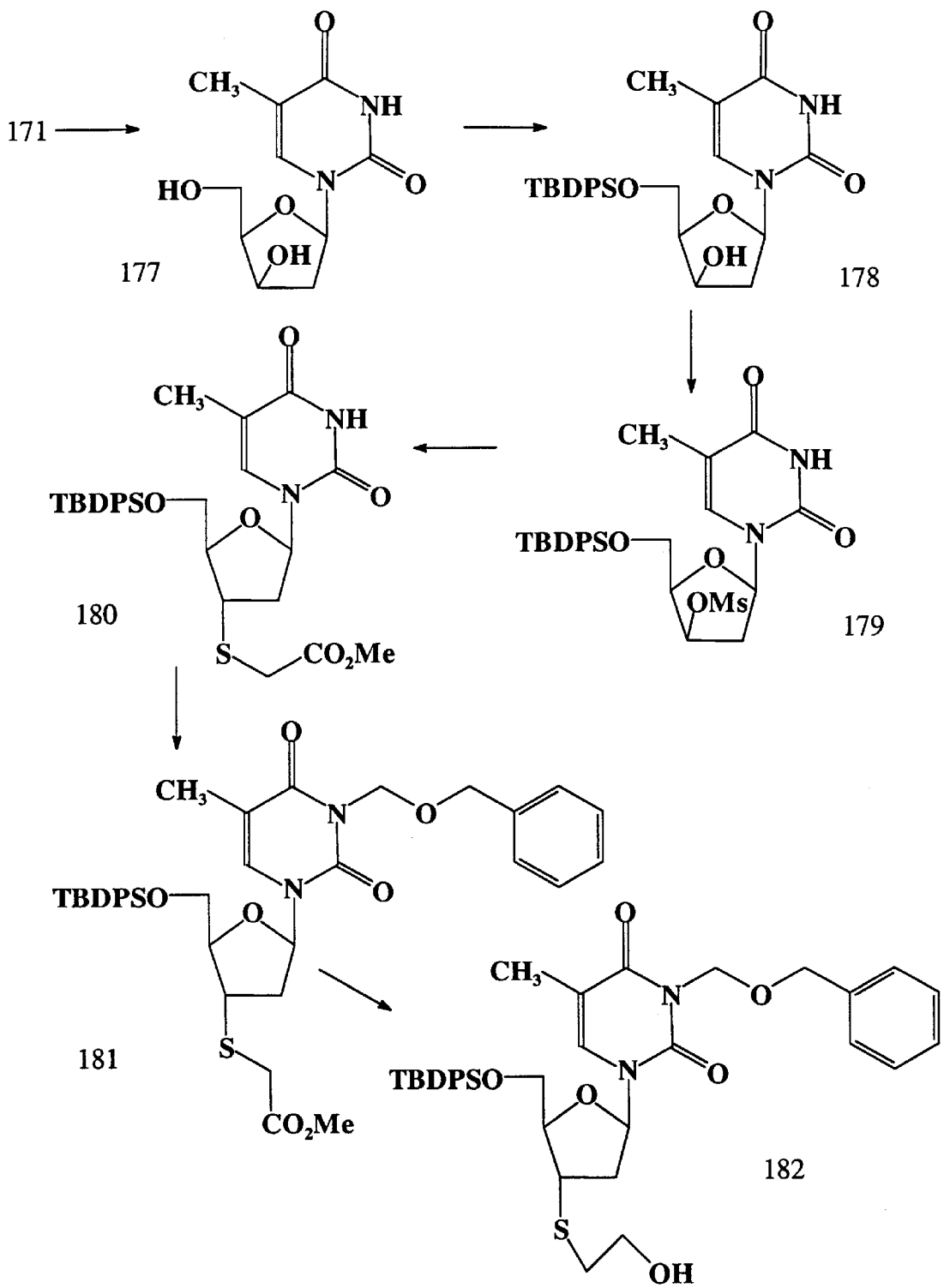
Figure 23:
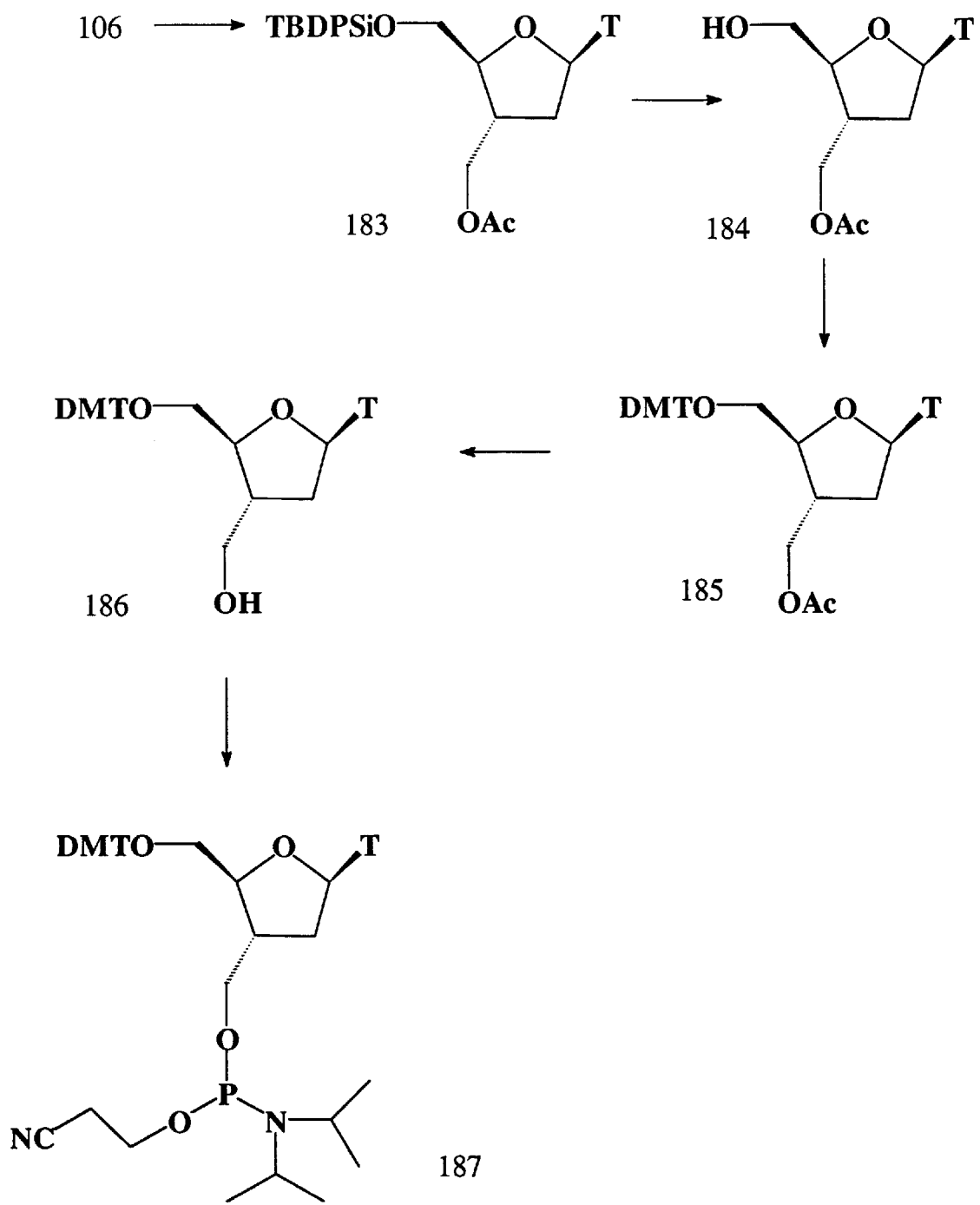

FIG. 4 illustrates a reaction scheme wherein a compound, as for instances, compound 10 having an $L_1$-$L_2$-$L_3$-$L_4$ group attached there to is reacted with a compound having a leaving group in the 4' position to form a dimer. An example is the coupling of compounds 8 and 10 using trimethylsilyltriflate in methylene chloride to provide glycol-linked dimer 11. FIG. 4 further illustrates deprotection, re-protection and activation (phosphitylation) with groups suitable for solid state oligonucleoside synthesis. For the glycol-linked dimer 11, base deprotection by catalytic hydrogenation and hydrolysis yields dimer 13 having free base and free 3' and 5' hydroxyl termini. Compound 13 is the protected with a 5' DMT group and 3' phosphitylated.

FIGS. 5 through 18 illustrates synthetic schemes for the preparation of nucleoside intermediates as well as dimeric structures. Nucleoside intermediate compounds of FIGS. 5 through 18 are further reacted to form dimeric structures of FIG. 4. In these examples, reference is made in certain instances to FIG. 4 and to the $L_1$, $L_2$, $L_3$ or $L_4$ identifiers of FIG. 4. To assist in identifying the compounds of the examples, in all instances wherein one or more of $L_1$, $L_2$, $L_3$ or $L_4$ are a hetero atom, that hetero atom is specifically identified, e.g. $L_1$=O. Any of $L_1$, $L_2$, $L_3$ or $L_4$ that are not specifically identified as hetero atoms are "$CH_2$" groups. The following examples are illustrative and are not meant to be limiting of the present invention.

EXAMPLE 1

5'-O-Tert-Butyldiphenylsilylthymidine, 2

A stirring solution of thymidine (50.0 g, 207 mmol) and DMAP (10 mg, $8.2\times10^{-2}$ mmol) in 400 mL of pyridine was treated with TBDPSCl (43.4 g, 248 mmol) at 25° C. for 16 h. The solvent was removed under reduced pressure and the residue was diluted with 1 L of AcOEt. The mixture was washed with 5% aqueous HCl (2×100 mL) and $H_2O$ (100 mL). The organic layer was dried ($MgSO_4$) and concentrated under reduced pressure. The product was purified by silica gel chromatography ($CH_2Cl_2$/MeOH 20:1) to give 87.3 g (88%) of 2 as a white solid. An analytical sample was crystallized from diethylether. mp 164–166° C. (170–171° C. per Matulic-Adamic, *J. Chem. Soc., Chem. Comm.* 1985, 21, 1535) $R_f$($CH_2Cl_2$/MeOH 10:1) 0.31. $^1$H-NMR ($CDCl_3$): 1.08 (s, 9H, C-$Me_3$), 1.61 (s, 3H, 5-Me), 2.18 (ddd, 1H, J=13.8, 8.5, 6.0 Hz, 2'$H_\beta$), 2.19 (br s, 1H, $D_2O$ exchangeable, 3'-OH), 2.44 (ddd, 1H, J=13.8, 5.6, 2.1 Hz, 2'-$H_\alpha$), 3.25 (br s, 1H, 5'-OH, $D_2O$ exchangeable), 3.85 (dd, 1H, J=11.5, 2.5 Hz, 5'-CHH), 3.98 (dd, 1H J=11.5, 2.3 Hz, 5'-CHH), 4.06 (dd, 1H, J=2.5, 2.3 Hz, 4'H), 4.55 (dd, 1H J=6.0, 5.6 Hz, 3'-H), 6.43 (dd, 1H, J=8.5, 5.6 Hz, 1'-H), 7.26–7.51 (m, 6H, aromatic-H), 7.64–7.68 (m, 5H, 6-H and aromatic-H), 9.57 (s, 1H, NH, $D_2O$ exchangeable).

EXAMPLE 2

$N^3$-Benzyloxymethyl-5'-O-Tert-Butyldiphenylsilylthymidine, 3

To a stirred solution of 2 (117.0 g, 243.8 mmol) and Hunig's base (diisopropylethylamine, 63.0 g, 487.5 mmol) in $CH_2Cl_2$ (400 mL) at 23° C. was added a solution of benzyl chloromethyl ether (40.7 g, 260.0 mmol) over a 15 min. period. The resultant mixture was maintained at 23° C. and stirred for 14 h. Ether (1 L) was added to the mixture and the ethereal solution was washed with 10% aqueous HCl (2×100 mL) and $H_2O$ (200 mL). The organic layer was dried ($MgSO_4$) and concentrated under reduced pressure. The residue was purified by silica gel column chromatography ($CH_2Cl_2$/AcOEt 40:1 then 10:1) to yield 128.9 g (88%) of 3 as a white solid. $R_f$($CH_2Cl_2$/AcOEt 10:1) 0.31. $^1$H-NMR ($CDCl_3$): 1.10 (s, 9H, C-$Me_3$), 1.65 (s, 3H, 5-Me), 2.16 (m, 1H, 2'-$H_\beta$), 2.41 (m, 1H, 2'-$H_\beta$), 2.53 (br s, 1H 3'-OH), 3.84 (d, 1H, J=8.8 Hz, 5'-CHH), 3.98 (d, 1H, J=8.8 Hz, 5'-CHH), 4.01 (s, 1H, 4'-H), 6.64 (br s, 1H, 3'-H), 4.70 (s, 2H, $OCH_2Ph$), 5.50 (s, 2H, $NCH_2O$), 6.41 (dd, 1H, J=8.0, 5.8 Hz, 1'-H), 7.20–7.50 (m, 13H, aromatic-H), 7.65–7.69 (m, 3H, 6-H and aromatic-H). $^{13}$C-NMR ($CDCl_3$): 12.86 (–5-$CH_3$) 19.45 (+, C-$Me_3$), 27.09 (–, C-$Me_3$), 41.16 (+, 2'-C), 64.25 (+, 5'-C), 70.70 (+, O—C—Ph), 71.97 (–, 4'-C), 72.29 (+, N—C—O), 85.51 (–, 3'-C), 87.20 (–, 1'-C), 110.47 (+, 5-C), 127.72, 128.08, 128.36 (–, aromatic-C), 130.25 (–, 6-C), 132.42, 133.00 (+, aromatic-C) 134.39, 135.37, 135.62 (–, aromatic-C), 137.95 (+, aromatic-C), 151.01 (+, 2-C), 163.68 (+, 4-C).

EXAMPLE 3

$N^3$-Benzyloxymethyl-3'-O-Benzoyl-5'-O-Tert-Butyldiphenylsilylthymidine, 4

A stirred solution of 3 (128.0 g, 213.3 mmol) in a 4:1 mixture of $CH_2Cl_2/Et_3N$ (500 mL) was treated with (48.4 g, 40 mL, 344.6 mmol) of BzCl at 23° C. for 8 h. The resultant precipitate was removed by filtration. The filtrate was concentrated under reduced pressure to leave the crude product as a brownish syrup. Purification of the syrup by silica gel column chromatography (hexanes/AcOEt 10:1 then 1:1) gave 130.7 g (87%) of 4 as a white solid. $R_f$(Hexanes/AcOEt 1:1) 0.82 $^1$H-NMR ($CDCl_3$): 1.40 (s, 9H, C-$Me_3$), 1.60 (s, 3H, 5-Me), 2.37 (ddd, 1H, J=13.8, 9.3, 7.2 Hz, 2'-$H_\beta$), 2.62 (dd, 1H, J=13.8, 4.3 Hz, 2'-$H_\beta$), 4.09 (m, 2H, 5'-$H_\beta$), 4.26 (m, 1H, 4'-H), 4.74 (s, 2H, O—CH$_2$—Ph), 5.54 (s, 2H, N—CH$_2$—O), 5.71 (d, 1H, J=7.2 Hz, 3'-H), 6.57 (dd, 1H, J=9.3, 4.3 Hz, 1'-H), 7.24–7.74 (m, 13H, aromatic-H), 8.05–8.15 (m, 3H, 6-H and aromatic-H). $^{13}$C-NMR (CDCl$_3$): 12.82 (−, 5-Me), 19.54 (+, C-Me$_3$), 27.16 (C-Me$_3$), 38.28 (+, 2'-C), 64.41 (+, 5'-C), 70.80 (+, O—C—Ph), 72.29 (+, N—C—O), 75.60 (−, 4'-C), 85.28 (−, 1'-C and 3'-C), 110.95 (+, 5-C), 127.72, 128.23, 128.37, 128.50, 128.63 (−, aromatic-C), 129.43 (+, aromatic-C), 129.84, 130.22 (−, aromatic-C), 132.14, 133.07 (+, aromatic-C), 133.60 (−, 6-C), 133.94, 135.32, 135.65 (−, aromatic-C), 138.15 (+, aromatic-C), 151.19 (+, 2-C), 163.50 (+, 4-C), 166.11 (+, benzoyl C=O).

EXAMPLE 4

N$^3$-Benzyloxymethyl-3'-O-Benzoylthymidine, 5

The silyl ether 4 (96.0 g, 136.4 mmol) in THF (600 mL) was treated with hydrogen fluoride-pyridine (70% HF in pyridine, 30 mL) at 0° C. for 4 h under a N$_2$ atmosphere. The resultant mixture was diluted with AcOEt (600 mL) and washed with H$_2$O (2×300 mL). The organic layer was dried (MgSO$_4$) and concentrated at reduced pressure. The residue was purified by silica gel column chromatography (CH$_2$Cl$_2$/AcOEt 10:1) to give 61.6 g (97%) of 5 as a white solid. R$_f$(CH$_2$Cl$_2$/AcOEt 10:1) 0.29. $^1$H-NMR (CDCl$_3$+D$_2$O): 1.95 (s, 3H, 5-Me), 2.53 (m, 2H, 2'-H), 4.00 (m, 2H, 5'-H), 4.25 (m, 1H, 4'-H), 4.71 (s, 2H, O—CH$_2$—Ph), 5.51 (s, 2H, N—CH$_2$—O), 5.60 (m, 1H 3'-H), 6.36 (dd, 1H, J=7.6, 6.6 Hz, 1'-H), 7.25–7.66 (m, 9H, 6-H and aromatic-H), 8.05 (d, 2H, J=7.1 Hz, aromatic-H). $^{13}$C-NMR (CDCl$_3$): 13.29 (−, 5-Me), 37.82 (+, 2'-C), 62.54 (+, 5'-C), 70.73 (+, O—C—Ph), 72.25 (+, N—C—O), 75.82 (−, 4'-C), 85.43 (−, 3'-C), 86.13 (−, 1'-C), 110.41 (+, 5-C), 127.65, 128.36, 128.59 (−, aromatic-C), 129.34 (+, aromatic-C), 129.69 (−, 6-C), 133.60, 135.40 (−, aromatic-C), 137.87 (+, aromatic-C), 151.18 (+, 2-C), 163.65 (+, 4-C), 166.11 (+, benzoyl C=O).

EXAMPLE 5

Tert-Butyl-N$^3$-Benzoxymethyl-3'-O-Benzoylthymidine-5'-Carboxylate, 6

The reaction was performed as described by Corey and Samuelsson, *J. Org. Chem.* 1984, 49, 4735, for the oxidation of 5'-OH of the uridine derivative to its corresponding 5'-tert-butyl carboxylate. Chromium(VI) oxide (31.4 g, 314.2 mmol) in CH$_2$Cl$_2$ (480 mL) was cooled to 0° C. and then pyridine (49.7 g, 638.4 mmol) in DMF (120 mL) was added dropwise to the reaction mixture (caution: extremely exothermic) over a period of 1 h. The mixture was stirred at 0° C. for 30 min. Alcohol 5 (36.6 g, 78.5 mmol) in CH$_2$Cl$_2$/DMF (4:1 v/v, 100 mL) was added followed by acetic anhydride (64.1 g, 628.4 mmol) and t-BuOH (116.4 g, 1.57 mmol). The resultant mixture was warmed to 23° C. and stirred for 18 h. Ethanol (20 mL) was added to the reaction and the mixture was stirred for additional 15 min. The reaction mixture was poured into AcOEt (400 mL) and the insoluble material was filtrated through a Buchner funnel padded with 200 g of silica gel and 50 g of MgSO$_4$. The solid left in the funnel was rinsed with AcOEt (4×100 mL). The combined filtrate and rinses were concentrated under reduced pressure. The residue was purified by silica gel column chromatography (hexanes/AcOEt 3:1) to give 25.6 g (61%) of 5 as a white solid. An analytical sample (about 400 mg) was crystallized from ether/hexanes afforded white, needle-like crystals. mp 80–82° C. R$_f$(hexanes/AcOEt 3:1) 0.23. $^1$H-NMR (CDCl$_3$): 1.55 (s, 9H, C-Me$_3$), 2.21 (ddd, 1H, J=14.3, 9.1, 5.0 Hz, 2'-H$_\beta$), 2.61 (dd, 1H, J=14.3, 5.2 Hz, 2'-H$_\alpha$), 4.63 (s, 1H, 4'-H), 4.71 (s, 2H, O—CH$_2$—Ph), 5.51 (s, 2H, N—CH$_2$—O), 5.65 (d, 1H, J=5.0 Hz, 3'-H), 6.61 (dd, 1H, J=9.1, 5.2 Hz, 1'-H), 7.24–7.63 (m, 8H, aromatic-H), 8.07 (d, 2H, J=7.1 Hz, aromatic-H), 8.09 (s, 1H, 6-H). $^{13}$C-NMR (CDCl$_3$): 13.40 (−, 5-Me), 27.92 (−, C-Me$_3$), 36.65 (+, 2'-C), 70.58 (+, O—C—Ph), 72.09 (+, N—C—O), 76.66 (−, 4'C), 82.55 (−, 3'-C), 83.36 (+, C-Me$_3$), 86.88 (−, 1'-C), 110.61 (+, 5-C), 127.55, 127.24 128.23, 128.53 (−, aromatic-C), 128.99 (+, aromatic-C), 129.78 (−, 6-C), 133.71, 134.72 (−, aromatic-C), 138.06 (+, aromatic-C), 151.14 (+, 2-C), 163.28 (+, 4-C), 165.26 (+, benzoyl C=O), 169.40 (+, 5'-C).

EXAMPLE 6

N$^3$-Benzoxylmethyl-3'-O-Benzoylthymidine-5'-Carboxylic Acid, 7

A solution of 6 (22.0 g, 41.0 mmol) in CF$_3$COOH (100 mL) was stirred at 23° C. for 2 h. Toluene (200 Ml) was then added and the mixture was concentrated under reduced pressure. The coevaporation of toluene was repeated twice to ensure complete removal of the CF$_3$COOH. The resultant light yellow powder was purified by silica gel column chromatography (CH$_2$Cl$_2$/AcOEt 8:1) to afford 19.3 g (87%) of 7 as a white powder. R$_f$(CHCl$_3$/MeOH 4:1) 0.39, $^1$H-NMR (CDCl$_3$+D$_2$O): 1.95 (s, 3H, 5-Me), 2.27 (ddd, 1H, J=14.3, 9.1, 4.9 Hz, 2'-H$_\beta$), 2.68 (dd, 1H, J=14.3, 5.2 Hz, 2'H$_\beta$), 4.71 (s, 2H, O—CH$_2$—Ph), 4.79 (s, 1H, 4'-H), 5.52 (s, 2H, N—CH$_2$—O), 5.76 (d, 1H, J=4.9 Hz, 3'-H), 6.55 (dd, 1H, J=9.1, 5.2 Hz, 1'-H), 7.24–7.60 (m, 8H, aromatic-H), 7.97 (s, 1H, 6-H), 8.06 (d, 2H, J=7.1 Hz, aromatic-H). $^{13}$C-NMR (CDCl$_3$): 13.42 (+, 5-Me), 36.68 (+, 2'-C), 70.83 (+, O—C—Ph), 73.38 (+, N—C—O), 76.93 (−4'-C), 82.01 (−, 3'-C), 87.58 (−, 1'-C), 110.80 (+, 5-C), 127.72, 127.86, 128.39, 128.70 (−, aromatic-C), 128.71 (+, aromatic-C), 129.90 (−, 6-C), 133.95, 135.63 (−, aromatic-C), 128.53 (+, aromatic-C), 11.20 (+, 2-C), 163.94 (+, 4-C), 165.61 (+, benzoyl C=O), 171.93 (+, 5'-C).

EXAMPLE 7

(2'S, 4'S, 5'R)-1-[5'-Acetoxy-4'-Benzoyloxy-Tetrahydrofuran-2'-Yl]-N$^3$-Benzoxymethylthymine, 8

A stirred solution of 7 (10.6 g, 22.0 mmol) in DMF (75 mL) was treated with Pb(OAc)$_4$ (11.8 g, 26.5 mmol) at 23° C. for 2 h under darkness. The mixture was diluted with AcOEt (250 mL) and the resultant suspension was filtrated through a Celite pad (50 g). The solid was rinsed several times with AcOEt. The combined filtrate and rinses were concentrated under reduced pressure. The residue was purified by silica gel column chromatography (hexanes/AcOEt 1:1) to give 6.5 g (60%) of a 3:7 α/β (as determined by the $^1$H-NMR 4'-C ratio) anomeric mixture of 8 as a light yellow syrup. An aliquot of the anomeric mixture (~0.2 g) was separated on a silica gel column (hexanes/AcOEt 8:1→2:1 gradient) to afford 53 mg of 8α and 121 mg of 8β, both as white foams.

8α: R$_f$(hexanes/AcOEt, 1:1) 0.53. $^1$H-NMR (CDCl$_3$): 1.95 (d, 3H, J=1.1 Hz, 5-CH$_3$), 2.05 (s, 3H, acetoxy-CH$_3$), 2.52–2.75 (m, 2H, 3'-H), 4.70 (s, 2H, OCH$_2$Ph), 5.49 (s, 2H, NCH$_2$O), 5.60–5.65 (m, 1H, 4'-H), 6.40 (dd, 1H, J=7.9, 3.8 Hz, 2'-H), 6.72 (d, 1H, J=4.0 Hz, 5'-H), 7.06 (d, 1H, J=1.1 Hz, 6-H), 7.22–7.60 (m, 8H, aromatic-H), 8.02 (d, 2H, J=7.6 Hz, aromatic-H). $^{13}$C-NMR (CDCl$_3$): 13.04 (−, 5-CH$_3$), 20.73 (−, acetoxy-$CH_3$), 33.81 (+, 3'-C), 70.45 (+, O—C—Ph), 71.08 (−, 4'-C), 72.11 (+, N—C—O), 85.47 (−, 2'-C), 94.10 (−, 5'-C), 110.90 (+, 5-C), 127.47, 128.11, 128.45 (−, aromatic-C), 128.64 (+, aromatic-C), 129.54 (−, 6-C), 133.55, 133.92 (−, aromatic-C), 137.75 (+, aromatic-C), 150.55 (+, 2-C), 163.01 (+, 4-C), 165.43 (+, benzoyl C=O), 169.18 (+, acetoxy C=O). Anal. Calcd. for $C_{26}H_{26}N_2O_8$: C, 63.16; H, 5.26; N, 5.67. Found: C, 63.12; H, 5.38; N, 5.45.

8β: $R_f$(hexanes/AcOEt 1:1) 0.47. $^1$H-NMR ($CDCl_3$): 1.95 (s, 3H, 5-$CH_3$), 2.18 (s, 3H, acetoxy-$CH_3$), 2.33 (ddd, 1H, J=14.9, 8.2, 4.9 Hz, 3'-$H_β$), 2.75 (dd, 1H, J=14.9, 6.2 Hz, 3'-$H_α$), 4.70 (s, 2H, $OCH_2$Ph), 5.50 (s, 2H, $NCH_2$O), 5.52 (d, 1H, J=4.9 Hz, 4'-H), 6.42 (s, 1H, 5'-H), 6.73 (dd, 1H, J=8.2, 6.2 Hz, 2'-H), 7.22–7.63 (m, 9H, 6-H and aromatic-H), 8.04 (d, 2H, J=7.5 Hz, aromatic-H). $^{13}$C-NMR ($CDCl_3$): 13.40 (−, 5-$CH_3$), 20.82 (−, acetoxy-$CH_3$), 34.95 (+, 3'-C), 70.51 (+, O—C—Ph), 72.07 (+, N—C—O), 76.64 (−, 4'-C), 87.15 (−, 2'-C), 98.61 (−, 5'-C), 111.03 (+, 5-C), 127.45, 128.11, 128.45 (−, aromatic-C), 129.68 (−, 6-C), 133.02, 133.69 (−, aromatic-C), 137.77 (+, aromatic-C), 150.91 (+, 2-C), 162.84 (+, 4-C), 165.12 (+, benzoyl C=O), 169.13 (+, acetoxy C=O). Anal. Calcd for $C_{26}H_{26}N_2O_8 \cdot H_2O$: C, 60.94; H, 5.47; N, 5.47. Found: C, 60.98; H, 5.18; N, 5.30.

EXAMPLE 8

$N^3$-Benzyloxymethyl-3'-O-Ethoxycarbomethyl-5'-O-Tert-Butyldiphenylsilylthymidine, 9

A stirred solution of 8 (20.2 g, 33.7 mmol) in DMF (80 mL) was treated with NaH (1.2 g, 50.0 mmol) for 30 min at 0° C. Ethyl bromoacetate (9.0 g, 54.1 mmol) was added via a syringe to the resulting solution over a 5 min period. The reaction mixture was stirred for 16 h at 0° C. then diluted with AcOEt (400 mL) and washed with $H_2O$ (2×50 mL). The organic layer was dried ($MgSO_4$) and concentrated under reduced pressure. The residue was purified by silica gel column chromatography (hexanes/AcOEt 10:1 then 3:1) to afford 17.6 g (76.2%) of 9 as a light yellow syrup. $R_f$(hexanes/AcOEt 3:1) 0.23. $^1$H-NMR ($CDCl_3$): 1.09 (s, 9H, C-$Me_3$), 1.21 (t, 3H, J=7.1 Hz, ethoxy $CH_3$), 1.63 (s, 3H, 5-$CH_3$), 2.04 (ddd, 1H, J=14.3, 8.6, 6.2 Hz, 2'-$H_β$), 2.52 (ddd, 1H, J=14.3, 5.4, 0.9 Hz, 2'-$H_α$), 3.86 (dd, 1H, J=11.4 2.6 Hz, 5'-CHH), 3.99 (dd, 1H, J=11.4, 3.0 Hz, 5'-CHH), 4.07 (ABq, 2H, J=14.6 Hz, $OCH_2CO_2$Et), 4.16 (m, 1H, 3'-H), 4.21 (q, 2H, J=7.1 Hz, ethoxy $CH_2$), 4.27 (m, 1H, 4'-H), 4.71 (s, 2H, $OCH_2$Ph), 5.50 (s, 2H, $NCH_2$O), 6.36 (dd, 1H, J=8.6, 5.4 Hz, 1'-H), 7.26–7.50 (m, 12H, 6-H and aromatic-H), 7.42–7.67 (m, 4H, aromatic-H). $^{13}$C-NMR ($CDCl_3$): 12.86 (−, 5-$CH_3$), 14.27 (−, ethoxy $CH_3$), 19.40 (+, C-$Me_3$), 27.05 (−, C-$Me_3$), 37.85 (+, 2'-C), 61.16 (+, 5'-C), 64.21 (+, O—C—$CO_2$Et), 66.69 (+, ethoxy $CH_2$), 70.58 (+, O—C—Ph), 72.23 (+, N—C—O), 80.54 (−, 4'-C), 85.05 (−, 3'-C), 85.43 (−, 1'-C), 110.49 (+, 5-C), 127.65, 127.75, 128.05, 128.33 (−, aromatic-C), 130.15 (−, 6-C), 132.38, 132.86 (+, aromatic-C), 133.98, 135.36, 135.59 (−, aromatic-C), 138.06 (+, aromatic-C), 150.96 (+, 2-C), 163.51 (+, 4-C), 169.88 (+, carbonyl C=O).

EXAMPLE 9

$N^3$-Benzyloxymethyl-3'-O-(2-Hydroxyethyl)-5'-O-Tert-Butyldiphenylsilylthymidine, 10

A stirred solution of 9 (16.6 g, 24.2 mmol) in MeOH (100 mL) at 0° C. was treated with $NaBH_4$ (5.0 g, 132.2 mmol) added in 5 portions over a 30 min period. The resultant mixture was warmed to 23° C. and stirred for an Additional 8 h. The pH of the reaction was adjusted to 6 by titrating with 5% aqueous HCl. The reactions mixture was concentrated and the residue was coevaporated with MeOH (3×100 mL). The resultant residue was diluted AcOEt (300 mL) and the undissolved solid was filtrated through a pad of Celite. The filtrate was concentrated under vacuum and the residue was purified by silica gel column chromatography (hexanes/AcOEt 5:1 then 2:1) to give 14.0 g (89.8%) of 10 as a pale yellow foam. $R_f$(hexanes/AcOEt 1:1) 0.39 $^1$H-NMR ($CDCl_3$): 1.10 (s,9H, C-$Me_3$), 1.66 (s, 3H, 5-$CH_3$), 1.90 (br s, 1H, $D_2O$ exchangeable, OH), 2.03 (ddd, 1H, J=14.3, 8.6, 4.3 $H_z$, 2'-$H_β$), 2.48 (ddd, 1H, J=14.3, 5.5, 0.9 $J_z$, 2'-$H_α$), 3.45–3.60 (m, 2H, $OCH_2CH_2$OH), 3.70–3.79 (m, 2H, $OCH_2CH_2$OH), 3.81 (dd, 1H, J=11.6, 2.5 $H_z$, 5'-CHH), 3.99 (dd, 1H, J=11.6, 2.7 $H_z$, 5'-CHH), 4.10 (m, 1H, 4'-H), 4.17 (m, 1H, 3'-H), 4.71 (s, 2H, $OCH_2$Ph), 5.50 (s, 2H, $NCH_2$O), 6.34 (dd, 1H, J=8.6, 5.5 Hz, 1'-H), 7.21–7.50 (m, 12H, 6-H and aromatic-H), 7.64–7.67 (m, 4H, aromatic-H). $^{13}$C-NMR ($CDCl_3$): 12.87 (−, 5-$CH_3$), 19.41 (+, C-$Me_3$), 27.09 (−, C-$Me_3$), 37.95 (+, 2'-C), 61.70 (+, O—C—C—OH), 64.46 (+, 5'-C), 70.70 (+, O—C—C—OH), 70.73 (+, O—C—Ph), 72.24 (−, 4'-C), 80.15 (+, N—C—O), 84.96 (−, 3'-C), 85.52 (−, 1'-C), 110.50 (+, 5-C), 127.70, 128.06, 128.33 (−, aromatic-C), 130.18 (−, 6-C), 132.41, 132.90 (+, aromatic-C), 134.14, 135.38, 135.61 (−, aromatic-C), 138.07 (+, aromatic-C), 151.04 (+, 2-C), 163.57 (+, 4-C).

EXAMPLE 10

[2S-(2α,3β,5α)]-3'-O-[2-[[3-(Benzoyloxy)-5-[3,4-Dihydro-5-Methyl-2,4-Dioxo-3-[(Phenylmethoxy)Methyl]-1(2H)-Pyrimidinyl]-Tetrahydro-2-Furanyl]Oxy]Ethyl]-5-O-[(1,1-Dimethylethyl)Diphenylsilyl]-3-[(Phenylmethoxy)Methyl]-Thymidine 11 (Ethyleneglycol linked dimer, FIG. 4, Compound A, $L_1$=O, $L_4$=O)

Trimethylsilyl triflate (TMSOTf, 0.25 mL, 288 mg, 1.30 mmol) was added a via syringe in one portion to a stirred solution of 8 (410 mg, 0.83 mmol) and 10 (609 mg, 0.95 mmol) in $CH_2Cl_2$ (20 mL) at −23° C. The resultant yellow solution was stirred at −23° C. for 4 h under $N_2$. The reaction mixture was poured into a bilayer solution of AcOEt/$H_2O$ (10:1, 110 mL) containing $Et_3N$ (1 mL). The organic layer was dried ($MgSO_4$) and concentrated under reduced pressure. The residue was purified by $SiO_2$ column chromatography (hexanes/AcOEt 5:1 then 2:1) to give 252 mg (28%) of 11 as a white foam. $R_f$(hexanes/AcOEt 1:1) 0.41. $^1$H-NMR ($CDCl_3$): 1.10 (s, 9H, C-$Me_3$), 1.64 (s, 3H, ribo-5-$CH_3$), 1.96 (s, 3H, THF-5-$CH_3$), 2.00 (m, 1H, ribo-2'-$H_β$), 2.32 (m, 1H, THF-2'-$H_α$), 2.50 (m, 1H, ribo-2'-$H_β$), 2.62 (m, 1H, THF-2'-$H_α$), 3.55–3.75 and 3.83–3.90 (m, 4H, $OCH_2CH_2$O), 3.84 (dd, 1H, J=11.6, 2.4 Hz, ribo-5'CHH), 3.99 (dd, 1H, J=11.6, 2.7 Hz, ribo-5'-CHH), 4.10–4.17 (m, 2H, ribo-3'-H and ribo-4'-H), 4.69 and 4.72 (s, 2H, $OCH_2$Ph), 5.26 (s, 1H, THF-4'-H), 5.44 (m, 1H, THF-3'-H), 5.47 and 5.52 (s, 2H, $NCH_2$O), 6.33 (dd, 1H, J=8.8, 5.4 Hz, ribo-1'-H), 6.79 (dd, 1H, J=7.3, 6.5 Hz, THF-1'-H), 7.21–7.50 (m, 14H, 6-H and aromatic-H), 7.55–7.72 (m, 5H, aromatic-H), 8.03 (m, 2H, aromatic-H). $^{13}$C-NMR ($CDCl_3$): 12.87 (−, ribo-5-$CH_3$), 13.45 (−, THF-5-$CH_3$), 19.41 (+, C-$Me_3$) 27.10 (−, C-$Me_3$), 35.01 (+, THF-2'-C), 37.73 (+, ribo-2'-C), 64.47 (+, 5'-C), 67.75 (+, O—C—C—O), 68.50 (+, O—C—C—O), 70.61 and 70.73 (+, O—C—Ph), 72.24 (+, N—C—O), 77.71 (−, ribo-4'-C), 80.63 (−ribo-3'-C), 84.97 (−, THF-3'-C), 85.57 (−, ribo-1'-C), 86.61 (−, THF-1'-C), 106.69 (−, THF-4'-C), 110.45 (+, ribo-5-C), 111.38 (+, THF-5-C), 127.67, 128.09, 128.33 (−, aromatic-C), 128.63 (−, ribo-6-C), 129.07 (+, aromatic-C), 129.86 (−, THF-6-C), 130.20, 130.30 (+, aromatic-C), 132.44 132.85 (+, aromatic-C), 133.74, 134.00, 135.24, 135.38, 135.62 (−, aromatic-C), 138.06 (+, aromatic-C), 150.95 (+, THF-2-C), 151.42 (+, ribo-2-C), 163.24 (+, THF-4-C), 163.49 (+, ribo-4-C), 165.65 (+, benzoyl C=O).

EXAMPLE 11

[2S-(2α,3β,5α)]-3'-O-[2-[[3-(Benzoyloxy)-5-[3,4-Dihydro-5-Methyl-2,4-Dioxo-1(2H)-Pyrimidinyl] Tetrahydro-2-Furanyl]Oxy]Ethyl]-5-O-[(1,1-Dimethylethyl)Diphenylsilyl]-Thymidine 12

(Deprotection of BOM blocking group via catalytic hydrogenation, FIG. 4, Compound B, $L_1$=O, $L_4$=O)

Pd(OH)$_2$/C (1.2 g) and 1 mL of HCO$_2$H (1 mL) was added to a solution of 11 (336 mg, 0.31 mmol) in MeOH/acetone (1:1, 30 mL). The mixture was hydrogenated at 40 psi for 14 h. The catalyst was filtered and washed with MeOH (2×50 ml). The combined filtrate and washings were concentrated under reduced pressure and the residue was purified by flash column chromatography (CH$_2$Cl$_2$/AcOEt 3:1) to afforded 211 mg (84.6%) of 12 as a white foam. R$_f$(CH$_2$Cl$_2$/AcOEt 4:1) 0.10. $^1$H-NMR (CDCl$_3$): 1.11 (s, 9H, C-Me$_3$), 1.63 (s, 3H, ribo-5-CH$_3$), 1.96 (s, 3H, THF-5-CH$_3$), 2.07–2.09 (m, 1H, ribo-2'-H$_\beta$), 2.40–2.45 (m, 1H, THF-2'-H$_\alpha$), 2.49–2.54 (m, 1H, ribo-2'-H$_\beta$), 2.62–2.68 (m, 1H, THF-2'-H$_\alpha$), 3.62–3.74 and 3.91–3.95 (m, 4H, OCH$_2$CH$_2$O), 3.85 (dd, 1H, J=11.6, 2.4 Hz, ribo-5'-CHH), 3.99 (dd, 1H, J=11.6, 2.8 Hz, ribo-5'-CHH), 4.12 (dd, 1H, J=2.8, 2.4 Hz, ribo-4'-H), 4.16 (d, 1H, J=5.2 Hz, ribo-3'-H), 4.69 (s, 2H, OCH$_2$Ph), 4.72 (s, 2H, OCH$_2$Ph), 5.26 (s, 1H, THF-4'-H), 5.44 (m, 1H, THF-3'-H), 5.47 (s, 2H, NCH$_2$O), 5.52 (s, 2H, NCH$_2$O), 6.32 (dd, 1H, J=8.8, 5.2 Hz, ribo-1'-H), 6.79 (dd, 1H, J=8.0, 6.8 Hz, THF-1$^1$-H), 7.39–7.48 (m, 10H, ribo-6-H and aromatic-H), 7.59–7.68 (m, 5H, THF-6-H and aromatic-H), 8.03 (m, 2H, aromatic-H), 8.85 (s, 1H, D$_2$O exchangeable, NH), 8.90 (s, 1H, D$_2$O exchangeable, NH). $^{13}$C-NMR (CDCl$_3$): 12.18 (−, ribo-5-CH$_3$), 12.82 (−, THF-5-CH$_3$), 19.39 (+, C-Me$_3$), 27.09 (−, C-Me$_3$), 34.94 (+, THF-2'-C), 37.69 (+, ribo-2'-C), 64.46 (+, 5'-C), 67.71 (+, O—C—C—O), 68.41 (+, O—C—C—O), 77.55 (−, ribo-4'-C), 77.78 (−, ribo-3'-C), 80.58 (−, THF-3'-C), 84.91 (−, ribo-1'-C), 85.88 (−, THF-1'-C), 106.63 (−, THF-4'-C), 111.23 (+, ribo-5-C), 112.20 (+, THF-5-C), 128.07, 128.58 (−, aromatic-C), 129.07 (+, aromatic-C), 129.88, 130.17 (−, aromatic-C), 132.43, 132.86 (+, aromatic-C), 133.66 (−, aromatic-C), 135.38 (−, ribo-6-C), 135.60 (−, THF-6-C), 150.79 (+, THF-2-C), 151.26 (+, ribo-2-C), 164.23 (+, THF-4-C), 164.48 (+, ribo-4-C), 165.69 (+, benzoyl C=O).

EXAMPLE 12

[2S-(2α,3β,5α)]-3'-O-[2-[[3-Hydroxy-5-[3,4-Dihydro-5-Methyl-2,4-Dioxo-1(2H)-Pyrimidinyl] Tetrahydro-2-Furanyl]Oxy]Ethyl]-5'-O-[(1,1-Dimethylethyl)Diphenylsilyl]-Thymidine 13

(Deprotecting of benzoyl blocking group, FIG. 4, Compound C, $L_1$=O, $L_4$=O)

A solution of 12 (1.99 g, 2.37 mmol) and NaOH (0.16 g, 4.00 mmol) in a mixture of MeOH:THF (2:1, 60 mL) was stirred for 2 h at 23° C. The reaction was quenched by adjusting the pH to 7.0 with dropwise addition of 5% aqueous HCl. The solvent was evaporated under reduced pressure and the resulting residue was purified by flash chromatography to give 1.66 g (95.2%) of 13 as a white foam. R$_f$(CH$_2$Cl$_2$/AcOEt, 1:1) 0.04. $^1$H-NMR (CDCl$_3$): 1.09 (s, 9H, C-Me$_3$), 1.63 (s, 3H, ribo-5-CH$_3$), 1.90 (s, 3H, THF-5-CH$_3$), 1.92 (br s, 1H, D$_2$O exchangeable, OH), 2.00–2.05 (m, 1H, ribo-2'-H$_\beta$), 2.14–2.19 (m, 1H, THF-2'-H$_\alpha$), 2.42–2.47 (m, 1H, ribo-2'-H$_\beta$), 2.48–2.53 (m, 1H, THF-2'-H$_\alpha$), 3.59–3.79 and 3.86–3.90 (m, 4H, OCH$_2$CH$_2$O), 3.80 (dd, 1H, J=11.6, 2.4 Hz, ribo-5'-CHH), 3.98 (dd, 1H, J=11.6, 2.8 Hz, ribo-5'-CHH), 4.11 (d, 1H, J=4.8 Hz, ribo-3'-H), 4.14 (dd, 1H, J=2.8, 2.4 Hz, ribo-4'-H), 4.44 (d, 1H, J=4.4 Hz, THF-3'-H), 5.12 (s, 1H, THF-4'-H), 6.30 (dd, 1H, J=9.2, 4.8 Hz, ribo-1'-H), 6.70 (dd, 1H, J=7.6, 7.2 Hz, THF-1'-H), 7.38–7.50 (m, 7H, ribo-6-H and aromatic-H), 7.63–7.66 (m, 3H, THF-6-H and aromatic-H), 9.52 (br s, 1H, D$_2$O exchangeable, NH), 10.05 (br s, 1H, D$_2$O exchangeable, NH). $^{13}$C-NMR (CDCl$_3$): 12.18 (−, ribo-5-CH$_3$), 12.72 (−, THF-5-CH$_3$), 19.37 (+, C-Me$_3$), 27.06 (−, C-Me$_3$), 37.68 (+, THF-2'-C and ribo-2'-C), 64.54 (+, 5'-C), 67.09 (+, O—C—C—O), 68.03 (+, O—C—C—O), 77.24 (−, ribo-4'-C), 77.47 (−, ribo-3'-C), 80.55 (−, THF-3'-C), 84.93 (−, ribo-1'-C), 86.18 (−, THF-1'-C), 109.05 (−, THF-4'-C), 111.43 (+, ribo-5-C), 111.75 (+, THF-5-C), 128.06, 130.19 (−, aromatic-C), 132.36, 132.81 (+, aromatic-C), 135.35 (−, ribo-6-C), 135.58 (−, THF-6-C), 136.25 (−, aromatic-C), 151.09 (+, THF-2-C), 151.30 (+, ribo-2-C), 164.48 (+, ribo-4-C and THF-4-C).

EXAMPLE 13

[2S-(2α,3β,5α)]-3'-O-[2-[[3-Hydroxy-5-[3,4-Dihydro-5-Methyl- 2,4-Dioxo-1(2H)-Pyrimidinyl] Tetrahydro-2-Furanyl]Oxy]Ethyl]-Thymidine 14

(Deprotecting of silyl group, FIG. 4, Compound D, $L_1$=O, $L_4$=O)

A solution of 13 (1.53 g, 2.08 mmol) in THF (10 mL) was treated with hydrogen fluoride-pyridine (70% HF in pyridine, 2.5 mL) at 23° C. for 16 h. The resulting suspension was filtered and the filtrate was concentrated under reduced pressure. The residue was purified by silica gel column chromatography (CHCl$_3$/MeOH, 20:1) to give 1.01 g (97.7%) of 14 as a white solid. R$_f$(CHCl$_3$/MeOH, 10:1) 0.29. $^1$H-NMR (DMSO-d$_6$): 1.77 (s, 3H, ribo-5-CH$_3$), 1.79 (s, 3H, THF-5-CH$_3$), 2.05–2.25 (m, 4H, ribo-2'- and THF-2'-H), 3.27–3.73 (m, 7H, OCH$_2$CH$_2$O, ribo-3' and ribo-5'-H), 3.92 (dd, 1H, J=6.0, 3.4 Hz, ribo-4'-H), 4.10 (m, 1H, THF-3'-H), 4.15 (d, 1H, J=2.6 Hz, THF-4'-H), 5.11 (t, 1H, J=5.1 Hz, D$_2$O exchangeable, ribo-5'-OH), 5.44 (d, 1H, J=3.8 Hz, D$_2$O exchangeable, THF-3'-OH), 6.11 (dd, 1H, J=8.6, 6.0 Hz, ribo-1'-H), 6.44 (t, 1H, J=7.3 Hz, THF-1'-H), 7.34 (s, 1H, ribo-6-H), 7.68 (s, 1H, THF-6-H), 11.30 (s, 1H, D$_2$O exchangeable, NH), 11.34 (s, 1H, D$_2$O exchangeable, NH). $^{13}$C-NMR (CD$_3$OD): 12.24 (−, ribo-5-CH$_3$), 12.34 (−, THF-5-CH$_3$), 36.23 (+, THF-2'-C), 36.73 (+, ribo-2'-C), 61.53 (+, 5'-C), 66.65 (+, O—C—C—O), 67.68 (+, O—C—C—O), 74.04 (−, ribo-3'-C), 79.83 (−, ribo-4'-C), 83.75 (−, THF-3'-C), 84.58 (−, ribo-1'-C), 85.03 (−, THF-1'-C), 108.53 (−, THF-4'-C), 109.50 (+, ribo-5-C), 110.28 (+, THF-5-C), 135.55 (−, ribo-6-C), 135.92 (−, THF-6-C), 150.44 (+, THF-2-C), 150.65 (+, ribo-2-C), 163.54 (+, ribo-4-C), 163.66 (+, THF-4-C). Anal. Calcd for C$_{21}$H$_{28}$N$_4$O$_{10}$·⅓ H$_2$O: C, 50.20; H, 5.71; N, 11.15. Found: C, 50.30; H, 5.82; N, 10.77.

EXAMPLE 14

[2S-(2α,3β,5α)]-3-O-[2-[[3-Hydroxy-5-[3,4-Dihydro-5-Methyl-2,4-Dioxo-1(2H)-Pyrimidinyl] Tetrahydro-2-Furanyl]Oxy]Ethyl]-5'-O-[Dimethoxytrityl]-Thymidine 15

5'-DMT-Glycol-Dimer via tritylation with DMT-Cl, FIG. 4, Compound E, $l_1$=O, $L_4$=O)

To a solution of 14 (420 mg, 0.85 mmol) in pyridine (30 mL) was added DMT-Cl (689 mg, 2.03 mmol) and Et$_3$N (205 mg) at room temperature. The reaction was heated to 80–85° C. and stirred for 6 h. The reaction mixture was cooled and the solvent was evaporated under reduced pressure. The residue was purified by silica gel column chromatography (CHCl$_3$/MeOH, 20:1→10:1) to give 638 mg (94%) of 15 as a light yellow foam. R$_f$(CHCl$_3$/MeOH, 10:1) 0.39. $^1$H-NMR (CDCl$_3$): 1.45 (d, 3H, J=1.1 Hz, ribo-5-CH,), 1.89 (br d, 4H, J=1.3 Hz, THF-5-CH and OH), 2.14–2.22 (m, 2H, ribo-2'-H), 2.44 (dd, 1H, J=14.0, 6.4 Hz, THF-2'-H$_\beta$), 2.53 (dd, 1H, J=14.0, 4.6 Hz, THF-2'-H$_\alpha$), 3.29 (dd, 2H, J=10.8, 2.8 Hz, ribo-5'-CHH), 3.51 (dd, 2H, J=10.8, 3.2 Hz, ribo-5'-CHH), 3.50–3.69 and 3.82–3.90 ( m, 4H, OCH$_2$CH$_2$O), 3.79 (s, 6H, 2×OCH$_3$), 4.17–4.94 (m, 2H, ribo-3' and -4'-H), 4.20 (d, 1H, J=4.6 Hz, THF-3'-H), 5.10 (s, 1H, THF-4'-H), 6.34 (dd, 1H, J=9.0, 5.1 Hz, ribo-1'-H), 6.69 (dd, 1H, J=8.1, 6.6 Hz, THF-1'-H), 6.84 (d, 2H, J=9.0 Hz, aromatic-H), 7.23–7.40 (m, 12H, ribo-6-H and aromatic-H), 7.63 (d, 1H, J=1.3 Hz, THF-6-H), 9.39 (s, 1H, NH), 9.91 (s, 1H, NH).

EXAMPLE 15

[2S-(2α,3β,5α)]-3'-O-[2-[[3-Hydroxy-5-[3,4-Dihydro-5-Methyl-2,4-Dioxo-1(2H)-Pyrimidinyl]Tetrahydro-2-Furanyl]Oxy]Ethyl]-5'-O-[Dimethoxytrityl]-3'-[(β-Cyanoethoxy)-N-(Diisopropyl)Phosphiryl]-Thymidine 16
DMT-Phosphoramidite-glycol dimer, FIG. 4, Compound F, L$_1$=O, L$_4$=O)

To a solution of 15 (798 mg, 1 mmol) in CH$_2$Cl$_2$ (40 mL) was added tetrazole diisopropylamine salt (35 mg, 0.2 mmol) and 2-cyanoethyl-N,N,N',N'-tetraisopropylphosphorodiamidite (603 mg, 2.0 mmol). The reaction was stirred at 23° C. for 16 h under an argon atmosphere. The mixture was diluted with 60 mL of CH$_2$Cl$_2$, washed with sat. aqueous NaHCO$_3$ (30 mL) and then washed with brine (30 mL). The organic layer was dried (MgSO$_4$) and concentrated at reduced pressure. The residue was purified by flash column chromatography (0.5% Et$_3$N in AcOEt) to give 788 mg (79%) of 16. R$_f$(0.5% Et$_3$N in AcOEt) 0.38. $^1$H-NMR (CDCl$_3$): 6.34 (dd, 1H, J=8.4, 5.4 Hz, ribo-1'-H), 6.63 (dd, 1H, J=8.0, 6.5 Hz, THF-1'-H). $^{31}$P-NMR (CDCl$_3$): 149.41 and 149.73.

EXAMPLE 16

N$^3$-Benzyloxymethyl-3'-O-(Phenoxythiocarbonyl)-5'-O-Tert-Butyl-Diphenylsilylthymidine, 17

N-hydroxysuccinimide (3.9 g, 34 mmol) and pyridine (24.3 mL, 300 mmol) were added to a solution of the alcohol 3 (90.0 g, 150 mmol) in 1 L of toluene. The mixture was warmed up to 80° C. and stirred for 10 min. Phenyl chlorothionoformate (30 g, 174 mmol) was added to the solution and the resultant reaction mixture was stirred at 80° C. for 8 h. The hot toluene solution was decanted from solids. The solids were rinsed with AcOEt (2×30 mL) and the combined toluene solution and AcOEt washes were concentrated under reduced pressure. The residue was purified by silica gel column chromatography (hexanes/AcOEt 9:1 then 3:1) to give 83.0 g (75.2%) of the title compound, 17, as a light yellow foam. R$_f$(hexanes/AcOEt 9:1) 0.24. $^{13}$C-NMR (CDCl$_3$): 12.97 (5-CH$_3$), 19.49 (2'-C), 27.16 (Me$_3$C), 38.32 (Me$_3$C), 64.87 (O—C—Ph), 70.75 (N—C—O), 72.28 (5'-C), 84.21 (4'-C), 84.90 (3'-C), 85.39 (1'-C), 110.82 (5-C), 121.95, 126.94, 127.72, 128.27, 128.40, 129.81 (Ar—C), 130.35 (6-C), 131.93, 132.79, 133.76, 135.38, 135.76, 138.30 (Ar—C), 151.05 (2-C), 153.42 (Ar—C), 163.40 (4-C), 194.36 (thioformate-C).

EXAMPLE 17

N$^3$-Benzyloxymethyl-3'-Deoxy-3'-(Allyl)-5'-O-Tert-Butyldiphenylsilylthymidine, 18

A solution of 17 (72.0 g, 98 mmol) and allyl tributyltin (69.8 g, 211 mmol) in 520 mL of benzene (520 mL) was purged by bubbling a stream of Ar through the solution for 10 min. The resultant mixture was warmed to 45–50° C. and AIBN (3.2 g, 20 mmol) was added. The solution was heated to refluxed for 10–12 h. The solution was cooled to 45–50° C., a further aliquot of AIBN (0.4 g, 2.5 mmol) was added and the mixture was refluxed for an additional 10–12 h. The addition of AIBN followed by refluxing was repeated (4×) until the starting material was completely consumed (as detected by tlc). The reaction mixture was cooled to 23° C. and the benzene was removed under reduced pressure. The residue was purified by silica gel column chromatography (hexanes/AcOEt 10:1 then 4:1) to give 39.4 g (64.5%) of the title compound, 18, as a colorless syrup. R$_f$(hexanes/AcOEt 4:1) 0.20. $^1$H-NMR (CDCl$_3$, 400 MHz): 1.10 (s, 9H, Me$_3$C), 1.63 (d, 3H, J=0.9 Hz, 5-CH$_3$), 2.05 (ddd, 1H, J=14.1, 7.0, 5.6 Hz, 2'-H$_\alpha$), 2.15–2.22 (m, 3H, 2'-H$_\beta$, and CH$_2$-CH=CH$_2$), 2.43 (m, 1H, 3'-H), 3.76 (dd, 1H, J=12.6, 3 2 Hz, 5'-CHH), 3.77 (ddd, 1H, J=7.2, 3.6, 3.2 Hz, 4'-H), 4.07 (dd, 1H, J=12.6, 3.6 Hz, 5'-CHH), 4.71 (s, 2H, OCH$_2$Ph), 5.03 (ddd, 1H, J=9.3, 1.7, 1.1 Hz, CH$_2$—CH═CHH$_{cis}$), 5.05 (ddd, 1H, J=16.8, 3.2, 1.5 Hz, CH$_2$—CH═CHH$_{trans}$), 5.49 (s, 2H, NCH$_2$O), 5.70 (ddt, 1H, J=16.8, 9.3, 6.8 Hz, CH$_2$—CH═CH$_2$), 6.11 (t, 1H, J=5.6 Hz, 1'-H), 7.23–7.51 (m, 12H, 6-H and Ar—H), 7.66–7.69 (m, 4H, Ar—H). $^{13}$C-NMR (CDCl$_3$): 13.04 (5-CH$_3$), 19.52 (2'-C), 27.18 (Me$_3$C), 36.41 (Me$_3$C), 36.95 (3'-C), 38.92 (C—C═C), 63.81 (O—C—Ph), 70.56 (N—C—O), 72.22 (5'-C), 85.54 (4'-C), 85.78 (1'-C), 109.66 (5-C), 117.14 (C—C═C), 127.64, 127.76, 128.04, 128.31, 129.70, 130.10, 132.80, 133.26 (Ar—C), 134.36 (C—C═C), 135.47, 135.64, 138.31 (Ar—C), 150.98 (2-C), 163.57 (4-C).

EXAMPLE 18

N$^3$-Benzyloxymethyl-3'-Deoxy-3'-(2,3-Dihydroxypropyl)-5'-O-Tert-Butyldiphenylsilylthymidine, 19

A suspension of 18 (16.3 g, 26.1 mmol) and NMO (4.0 g, 34.2 mmol) in a mixture of THF/H$_2$O (1:1, 160 mL) was treated with OsO$_4$ (3.6 mL of a 2.5 wt % solution in t-BuOH, 2.8×10$^{-1}$ mmol) at 23° C. for 14 h. Na$_2$S$_2$O$_5$ (12.0 g, 63.1 mmol) and Celite (20 g) in H$_2$O (100 mL) was added and the suspension was stirred for additional 20 min. The suspension was filtrated and the solids were rinsed with acetone. The combined filtrate and washings were concentrated under reduced pressure and the residue was purified by silica gel column chromatography (CH$_2$Cl$_2$/AcOEt 4:1) to give 16.9 g (98.3%) of 1:1 diastereomers of the title compound, 19, as a white foam. R$_f$(CH$_2$Cl$_2$/AcOEt 4:1) 0.24. $^{13}$C-NMR (CDCl$_3$): assignment for 1'-C. 86.39 and 86.75 ppm (diastereomer).

EXAMPLE 19

3'-Deoxy-3'-[3-[[3-(Benzoyloxy)-5-[3,4-Dihydro-5-Methyl-2,4-Dioxo-3-[(Phenylmethoxy)Methyl]-1 (2H)-Pyrimidinyl]Tetrahydro-2-Furanyl]Oxy]-2-Hydroxypropyl]-5-O-[(1,1-Dimethylethyl) Diphenylsilyl]-3-[(Phenylmethoxy)Methyl]-Thymidine 20
FIG. 4, Compound A, L$_2$=COH, L$_3$=CH$_2$, L$_4$=O)

Compound 19 is reacted with compound 8 as per the procedure of Example 10 to yield the title dimeric compound, 20.

EXAMPLE 20

3'-Deoxy-3'-[3-[[5-(3,4-Dihydro-5-Methyl-2,4-Dioxo-1(2H)-Pyrimidinyl)Tetrahydro-3-Hydroxy-2-Furanyl]Oxy]-2-Hydroxypropyl]-Thymidine 21

FIG. 4, Compound D, $L_2$=COH, $L_3$=$CH_2$, $L_4$=O)

Compound 20 is de-blocked as per the procedures of Examples 11, 12 and 13 to give the title compound, 21.

EXAMPLE 21

3'-Deoxy-5'-O-(Dimethoxytrityl)-3'-[3-[[5-[3,4-Dihydro-5-Methyl-2,4-Dioxo-1(2H)-Pyrimidinyl]Tetrahydro-3-Hydroxy-2-Furanyl]Oxy]-2-Hydroxypropyl]-Thymidine 22

FIG. 4, Compound E, $L_2$=COH, $L_3$=$CH_2$, $L_4$=O)

Compound 21 is protected with a DMT group on the 5'-OH of the 5' nucleoside of this dimer as per the procedure of Example 14 to give the title compound, 22.

EXAMPLE 22

3'-Deoxy-5'-O-(Dimethoxytrity)-3'-[3-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Oxy]-2-Hydroxypropyl]-Thymidine 23

FIG. 4, Compound F, $L_2$=COH, $L_3$=$CH_2$, $L_4$=O)

The dimer 22 is converted to its phosphoramidite as per the phosphitylation procedure of Example 15 to give the title compound, 23.

EXAMPLE 23

3'-Deoxy-3'-[3-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Oxy]-2-Oxopropyl]-5-O-[(1,1-Dimethylethyl)Diphenylsilyl]-3-[(Phenylmethoxy)Methyl]-Thymidine 24

FIG. 4, Compound A, $L_2$=C(=O), $L_3$=$CH_2$, $L_4$=O)

Compound 20 will be oxidized with $RuO_4$ as per the procedure of Varma, R. S. and Hogan, M. E., *Tetrahedron Letts.* 1992, 33, 7719 to yield the title dimeric compound, 24.

EXAMPLE 24

$N^3$-Benzyloxymethyl-3'-O-[2-(Thioacetyl)Ethyl]-5'-O-Tert-Butyl-Diphenylsilylthymidine, 25

Compound 10 will be treated with thioacetic acid (Aldrich Chemical) utilizing Mitsunobu reaction conditions (see Mitsunobu, O., *Synthesis* 1981, 1 and references cited therein) to yield the title compound, 25.

EXAMPLE 25

$N^3$-Benzyloxymethyl-3'-O-(2-Thiolethyl)-5'-O-Tert-Butyldiphenylsilylthymidine, 26

Compound 25 will be hydrolyzed with base to yield the title compound, 26.

EXAMPLE 26

3'-O-[2-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Thio]Ethyl]-5-O-[(1,1-Dimethylethyl)Diphenylsilyl]-3-[(Phenylmethoxy)Methyl]-Thymidine 27

(FIG. 4, Compound A, $L_1$=O, $L_4$=S)

Compound 26 is reacted with compound 8 as per the procedure of Example 10 to yield the title dimeric compound, 27.

EXAMPLE 27

3'-O-[2-[[5-(3,4-Dihydro-5-Methyl-2,4-Dioxo-1(2H)-Pyrimidinyl)Tetrahydro-3-Hydroxy-2-Furanyl]Thio]-Ethyl]-Thymidine 28

(FIG. 4, Compound D, $L_1$=O, $L_4$=S)

Compound 27 is de-blocked as per the procedures of Examples 11, 12 and 13 to give the title compound, 28.

EXAMPLE 28

5'-O-(Dimethoxytrityl)-3'-O-[2-[[5-[3,4-Dihydro-5-Methyl-2,4-Dioxo-1(2H)-Pyrimidinyl]Tetrahydro-3-Hydroxy-2-Furanyl]Thio]Ethyl]-Thymidine 29

(FIG. 4, Compound E, $L_1$=O, $L_4$=S)

Compound 28 is protected with a DMT group on the 5'-OH of the 5' nucleoside of this dimer as per the procedure of Example 14 to give the title compound, 29.

EXAMPLE 29

5'-O-(Dimethoxytrity)-3'-O-[2-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Thio]Ethyl]-Thymidine 30

(FIG. 4, Compound F, $L_1$=O, $L_4$=S)

The dimer 28 is converted to its phosphoramidite as per the phosphitylation procedure of Example 15 to give the title compound, 30.

EXAMPLE 30

$N^3$-Benzyloxymethyl-3'-O-(2-Azidoethyl)-5'-O-Tert-Butyldiphenylsilylthymidine, 31

Compound 10 in DMF will be treated with lithium azide (Eastman Kodak Co.) in the presence of triphenylphosphine and carbon tetrabromide to yield the title compound, 31.

EXAMPLE 31

$N^3$-Benzyloxymethyl-3'-O-(2-Aminoethyl)-5-O-Tert-Butyldiphenylsilylthymidine, 32

Compound 31 will be reduced with tributyl hydride to yield the title compound, 32.

EXAMPLE 32

3'-O-[2-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Amino]Ethyl]-5-O-[(1,1-Dimethylethyl)Diphenylsilyl]-3-[(Phenylmethoxy)Methyl]-Thymidine 33

(FIG. 4, Compound A, $L_1$=O, $L_4$=NH)

Compound 32 is reacted with compound 8 as per the procedure of Example 10 to yield the title dimeric compound, 33.

EXAMPLE 33

3'-O-[2-[[5-(3,4-Dihydro-5-Methyl-2,4-Dioxo-1(2H)-Pyrimidinyl)Tetrahydro-3-Hydroxy-2-Furanyl]Amino]Ethyl]-Thymidine 34

(FIG. 4, Compound D, $L_1$=O, $L_4$=NH)

Compound 33 is de-blocked as per the procedures of Examples 11, 12 and 13 to give the title compound, 34.

EXAMPLE 34

5'-O-(Dimethoxytrityl)-3'-O-[2-[[5-[3,4-Dihydro-5-Methyl-2,4-Dioxo-1(2H)-Pyrimidinyl]Tetrahydro-3-Hydroxy-2-Furanyl]Amino]Ethyl]-Thymidine 35

(FIG. 4, Compound E, $L_1$=O, $L_4$=NH)

Compound 34 is protected with a DMT group on the 5'-OH of the 5' nucleoside of this dimer as per the procedure of Example 14 to give the title compound, 35.

EXAMPLE 35

5'-O-(Dimethoxytrity)-3'-O-[2-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Amino]Ethyl]-Thymidine 36

(FIG. 4, Compound F, $L_1$=O, $L_4$=NH)

The dimer 35 is converted to its phosphoramidite as per the phosphitylation procedure of Example 15 to give the title compound, 36.

EXAMPLE 36

3'-Deoxy-3'-Allyl-5'-O-Tert-Butyldiphenylsilylthymidine 37

Utilizing the procedures of Examples 16 and 17 wherein compound 18 was obtained from compound 3 via compound 17, compound 2 is used as the starting material in place of compound 3. Compound 2 is converted via the procedure of Example 16 to an intermediate compound similar to compound 17 except this intermediate differs from compound 17 in that it does not have a blocking group on its heterocyclic base. The intermediate is then treated as per the procedure of Example 17 to give the title compound in 58% yield.

EXAMPLE 37

3'-Deoxy-3'-(3-Hydroxypropyl)-5'-O-Tert-Butyldiphenylsilylthymidine 38

Compound 37 (0.74 g, 2 mmol) was treated with $BH_3Me_2S$ (0.388 g, 5.12 mmol) in THF (10 ml). The reaction mixture was quenched with MeOH (0.7 mL). $H_2O$ (3 mL) and $NaHCO_3$ (1.11 g, 13.3 mmol) were added to the reaction mixture followed by $H_2O_2$ (30%, 1.91 mL, 16.92 mmol). After work-up, the residue was purified by silica gel chromatography. The product was crystallized from ether/hexane to furnish 0.41 g of the product as white needles. mp 150–151° C.

EXAMPLE 38

$N^3$-Benzyloxymethyl-3'-Deoxy-3'-(3-Hydroxypropyl)-5'-O-Tert-Butyldiphenylsilylthymidine 39

$BH_3$ (2.7 mL, 1.0 M solution in THF) was added to a solution of 18 (1.12 g, 1.8 mmol) in THF (15 ml) followed by stirring for 3 hr at 23° C. The reaction was quenched by the slow addition of MeOH (0.2 mL). A NaOH solution (6 mL, 3 M) was added and the reaction mixture concentrated under reduced pressure to a white solid. The solid was suspended in THF (15 mL) and oxidized by the addition of $H_2O_2$ (3 mL, 30% aqueous solution) for 3 hr at 23° C. The solvent was evaporated under reduced pressure and the residue purified by silica gel chromatography ($CH_2Cl_2$/AcOEt, 10:1 then 3:1) to give 0.51 g (44.3%) of the title compound as a white foam. $^1$H NMR ($CDCl_2$) δ1.10 (s, 9H, $Me_3C$); 1.18–1.54 (m, 4H); 1.65 (s, 3H, 5-$CH_3$); 2.10–2.40 (m, 3H); 2.18 (t, 1H, J=5.7 Hz, OH); 3.62 (m, 2H, $CH_2CH_2CH_2OH$); 3.65 (m, 2H, 5'-H); 4.07 (d, 1H, J=9.8 Hz, 4'-H); 4.71 (s, 2H, $OCH_2Ph$), 5.50 (s, 2H, $NCH_2O$); 6.11 (t, 1H, J=5.1 Hz, 1'-H); 7.26–7.51 (m, 12H, 6-H and aromatic-H); and 7.67–7.70 (m, 4H, aromatic-H).

EXAMPLE 39

$N^3$-Benzyloxymethyl-3'-Deoxy-3'-(3-Azidopropyl)-5'-O-Tert-Butyldiphenylsilylthymidine 40

Utilizing the conditions of Hetz et. al., *J. C. S. Perkin* 1 1980, 306, to a solution of compound 39 (1 eq) in DMF is added triphenylphosphine (1 eq) and lithium azide (5 eq) at room temperature. Carbon tetrabromide (1 eq) is added and the reaction mixture is stirred until judged complete by tlc. MeOH is added to quench the reaction mixture and the solvent is evaporated under reduced pressure. The residue is purified by silica gel chromatography to yield the title compound, 40.

EXAMPLE 40

$N^3$-Benzyloxymethyl-3'-Deoxy-3'-(3-Aminopropyl)-5'-O-Tert-Butyldiphenylsilylthymidine 41

Compound 40 will be reduced with tributyl hydride to yield the title compound, 41.

EXAMPLE 41

$N^3$-Benzyoxymethyl-3'-Deoxy-3'-(3-Mercaptopropyl)-5'-O-Tert-Butyldiphenylsilylthymidine 42

Compound 39 will be treated as per Examples 24 and 25 to yield the title compound, 42.

EXAMPLE 42

3'-Deoxy-3'-[3-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Oxy]Propyl]-5-O-[(1,1-Dimethylethyl)Diphenylsilyl]-3-[(Phenylmethoxy)Methyl]-Thymidine 43

(FIG. 4, Compound A, $L_4$=O)

A solution of 39 (1.2 g, 1.87 mmol) and 8 (9.2 g, 1.87 mmol) in $CH_2Cl_2/CH_3CN$ (25 mL, 4:1 mixture) was chilled to −23° C. under an argon atmosphere followed by the addition of $Et_3N$ (0.2 g, 2.0 mmol) and TMSOTf (1.04 g, 4.68 mmol). The reaction mixture was stirred at −23° C. for 4 hr followed by storage at −15° C. for 20 hr. A further aliquot of TMSOTf (0.5 g, 2.25 mmol) was added and the mixture was stored at −15° C. for an additional 16 hr. The reaction mixture was added to a bilayer of AcOEt/$H_2O$ (100 mL, 9:1 mixture) and $Et_3N$ (3 mL). The organic phase was separated, dried over $MgSO_4$ and evaporated under reduced pressure. The residue was purified by silica gel chromatography (hexanes/AcOEt, 10:1→2:1) to yield 0.61 g (30.3%) of the title compound as a yellow syrup. $^1$H NMR ($CDCl_3$): 1.11 (s, 9H, $Me_3C$); 1.25–1.36 (m, 1H, ribo-3'-H); 1.49–1.70 (m, 2H, $CH_2CH_2CH_2O$); 1.64 (s, 3H, ribo-5-$CH_3$); 1.81–1.88 (m, 1H, $CH_2CHHCH_2O$); 1.92 (s, 3H, THF-5-$CH_3$); 2.11–2.18 (m, 1H, $CH_2CHHCH_2O$); 2.22–2.36 (m, 3H, ribo-2'-H and THF-4-$H_β$); 2.65 (dd, 1H, J=15.0, 6.6 Hz, THF-4-$H_α$); 3.51–3.57 (m, 1H, $CH_2CH_2CHHO$); 3.74–3.81 (m, 3H, ribo-5'-H and $CH_2CH_2HHO$); 4.08–4.12 (m, 1H, ribo-4'-H); 4.71 (s, 4H, $OCH_2Ph$); 5.17 (s, 1H, THF-2-H); 5.41 (d, 1H, J=4.7 Hz, THF-3-H); 5.49 (s, 2H, $NCH_2O$), 5.52 (s, 2H, NCH$_2$O); 6.13 (dd, 1H, J=6.6, 3.8 Hz, ribo-1'-H); 6.80 (t, 1H, J=6.8 Hz, THF-2'-H); 7.23–7.69 (m, 24H, ribo-6-H, THF-6-H, and aromatic-H); and 8.04–8.06 (m, 2H, aromatic-H).

EXAMPLE 43

3'-Deoxy-3'-[3-[[5-(3,4-Dihydro-5-Methyl-2,4-Dioxo-1(2H)-Pyrimidinyl)Tetrahydro-3-Hydroxy-2-Furanyl]Oxy]Propyl]-Thymidine 44

(FIG. 4, Compound D, L$_4$=O)

Compound 43 is de-blocked as per the procedures of Examples 11, 12 and 13 to give the title compound, 44 as a white solid. R$_f$(CHCl$_3$/MeOH 10:1) 0.19; $^1$H NMR (D$_2$O): δ1.40–1.78 (m, 4H, CH$_2$CH$_2$CH$_2$O), 1.95 (s, 6H, ribo-5- and THF-5-CH$_3$), 2.20–2.53 (m, 5H, ribo-2'-H and -3'-H and THF-3'-H), 3.62–3.78 (m, 5H, CH$_2$CH$_2$CH$_2$O, ribo-4'-H, THF-4'-H and 5'-CHH), 3.97 (dd, 1H, J=12.6, 2.5 Hz, ribo-5'-CHH), 5.15 (s, 1H, THF-5'-H), 6.13 (dd, 1H, J=7.1, 3.7 Hz, ribo-1'-H), 6.59 (t, 1H, J=7.1 Hz, THF-2'-H), 7.58 (s, H, THF-6-H), 7.84 (s, 1H, ribo-6-H); $^{13}$C NMR (D$_2$O): δ26.37 (–, ribo-5-CH$_3$), 26.61 (–, THF-5-CH$_3$), 41.14 (+, ribo-2'-C), 41.64 (+, THF-3'-C), 50.89 (+, C—C—C—O), 51.50 (–, ribo-3'-C), 52.83 (+, C—C—C—O), 75.54 (+, C—C—C—O), 83.45 (+, ribo-5'-C), 98.15 (–, ribo-4'-C), 100.01 (–, THF-4'-C), 100.62 (–, ribo-1'-C), 101.49 (–, THF-2'-C), 123.36 (–, THF-5'-C), 125,25 (+, ribo-5-C), 126.34 (+, THF-5-C), 152.04 (–, ribo-6-C), 152.42 (–, THF-6-C), 166.21 (+, THF-2-C), 166.63 (+, ribo-2-C), 180.83 (+, ribo-4-C), 181.19 (+, THF-4-C).

EXAMPLE 44

3'-Deoxy-5'-O-(Dimethoxytrityl)-3'-[3-[[5-[3,4-Dihydro-5-Methyl-2,4-Dioxo-1(2H)-Pyrimidinyl]Tetrahydro-3-Hydroxy-2-Furanyl]Oxo]Propyl]-Thymidine 45

(FIG. 4, Compound E, L$_4$=O)

Compound 44 is protected with a DMT group on the 5'-OH of the 5' nucleoside of this dimer as per the procedure of Example 14 to give the title compound, 45 as a light yellow foam. R$_f$(CHCl$_3$/MeOH 10:1): 0.41; $^1$H NMR (CDCl$_3$): δ1.26–1.68 (m, 4H, CH$_2$CH$_2$CH$_2$O), 1.76 (s, 3H, ribo-5-CH$_3$), 1.85 (s, 3H, THF-5-CH$_3$), 2.08–2.43 (m, 5H, ribo-2'- and -3'-H and THF-3'-H), 3.23 (dd, 1H, J=7.5, 2.1 Hz, ribo-5'-CHH), 3.41–3.57 (m, 3H, CH$_2$CH$_2$CH$_2$O and ribo-4'-H), 3.60 (dd, 1H, J=7.5, 2.1 Hz, ribo-5'-CHH), 3.70–3.80 (m, 1H, ribo-4'-H), 3.79 (s, 6H, OCH$_3$×2), 4.27 (s, 1H, THF-4'-H), 4.98 (s, 1H, THF-5'-H), 6.05 (dd, 1H, J=6.7, 2.8 Hz, ribo-1'-H), 6.67 (t, 1H, J=6.9 Hz, THF-2'-H), 6.83–6.86 (m, 4H, aromatic-H), 7.21–7.78 (m, 10H, aromatic-H and THF-6-H), 7.77 (s, 1H, ribo-6-H), 9.24 (s, 1H, NH), 9.37 (s, 1H, NH); $^{13}$C NMR (CDCl$_3$): δ12.20 (–, ribo-5-CH$_3$), 12.84 (–, THF-5-CH$_3$), 27.97 (+, C—C—C—O), 28.58 (+, C—C—C—O), 37.47 (–, ribo-3'-C), 37.78 (+, ribo-2'-C), 39.54 (–, THF-3'-C), 55.30 (–, OCH$_3$), 62.76 (+, C—C—C—O), 68.18 (+, ribo-5'-C), 75.27 (–, THF-4'-C), 77.37 (–, ribo-4'-C), 85.68 (–, ribo-1'-C), 85.70 (–, THF-2'-C), 86.57 (+. Ph$_3$-C), 108.90 (–, THF-5'-C), 110.48 (+, ribo-5-C), 111.66 (+, THF-5-C), 113.30 (–, aromatic-C), 127.17 (–, aromatic-C), 128.04 (–, ribo-6-C), 128.16 (–, THF-6-C), 130.13 (–, aromatic-C), 135.51 (+, aromatic-C), 135.98 (–, aromatic-C),144.21 (+, aromatic-C), 150.85 (+, THF-2-C), 51.20 (+, ribo-2-C), 158.68 (+, aromatic-C), 164.22 (+, ribo-4-C), 164.67 (+, THF-4-C).

EXAMPLE 45

3'-Deoxy-5'-O-(Dimethoxytrity)-3'-[3-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Oxo]Propyl]-Thymidine 46

The dimer 45 is converted to its phosphoramidite as per the phosphitylation procedure of Example 15 to give the title compound, 46 as a white foam. R$_f$(CHCl$_3$/MeOH 10:1): 0.73; $^{31}$P NMR (CDCl$_3$): δ149.26 and 149.60 ppm (diastereomer).

EXAMPLE 46

3'-Deoxy-3'-[3-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Thio]Propyl]-5-O-[(1,1-Dimethylethyl)Diphenylsilyl]-3-[(Phenylmethoxy)Methyl]-Thymidine 47

(FIG. 4, Compound A, L$_4$=S)

Compound 42 is reacted with compound 8 as per the procedure of Example 10 to yield the title dimeric compound, 47.

EXAMPLE 47

3'-Deoxy-3'-[3-[[5-(3,4-Dihydro-5-Methyl-2,4-Dioxo-1(2H)-Pyrimidinyl)Tetrahydro-3-Hydroxy-2-Furanyl]Thio]Propyl]-Thymidine 48

(FIG. 4, Compound D, L$_4$=S)

Compound 47 is de-blocked as per the procedures of Examples 11, 12 and 13 to give the title compound, 48.

EXAMPLE 48

3'-Deoxy-5'-O-(Dimethoxytrityl)-3'-[3-[[5-[3,4-Dihydro-5-Methyl-2,4-Dioxo-1(2H)-Pyrimidinyl]Tetrahydro-3-Hydroxy-2-Furanyl]Thio]Propyl]-Thymidine 49

(FIG. 4, Compound E, L$_4$=S)

Compound 48 is protected with a DMT group on the 5'-OH of the 5' nucleoside of this dimer as per the procedure of Example 14 to give the title compound, 49.

EXAMPLE 49

3'-Deoxy-5'-O-(Dimethoxytrity)-3'-[3-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Thio]Propyl]-Thymidine 50

(FIG. 4, Compound F, L$_4$=S)

The dimer 49 is converted to its phosphoramidite as per the phosphitylation procedure of Example 15 to give the title compound, 50.

EXAMPLE 50

3'-Deoxy-3'-[3-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Amino]Propyl]-5-O-[(1,1-Dimethylethyl)Diphenylsilyl]-3-[(Phenylmethoxy)Methyl]-Thymidine 51

(FIG. 4, Compound A, L$_4$=NH)

Compound 41 is reacted with compound 8 as per the procedure of Example 10 to yield the title dimeric compound, 51.

EXAMPLE 51

3'-Deoxy-3'-[3-[[5-(3,4-Dihydro-5-Methyl-2,4-Dioxo-1(2H)-Pyrimidinyl)Tetrahydro-3-Hydroxy-2-Furanyl]Amino]Propyl]-Thymidine 52

(FIG. 4, Compound D, L$_4$=NH)

Compound 51 is de-blocked as per the procedures of Examples 11, 12 and 13 to give the title compound, 52.

EXAMPLE 52

3'-Deoxy-5'-O-(Dimethoxytrityl)-3'-[3-[[5-[3,4-Dihydro-5-Methyl-2,4-Dioxo-1(2H)-Pyrimidinyl]Tetrahydro-3-Hydroxy-2-Furanyl]Amino]Propyl]-Thymidine 53

(FIG. 4, Compound E, L$_4$=NH)

Compound 52 is protected with a DMT group on the 5'-OH of the 5' nucleoside of this dimer as per the procedure of Example 14 to give the title compound, 53.

EXAMPLE 53

3'-Deoxy-5'-O-(Dimethoxytrity)-3'-[3-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Amino]Propyl]-Thymidine 54

(FIG. 4, Compound F, $L_4$=NH)

The dimer 53 is converted to its phosphoramidite as per the phosphitylation procedure of Example 15 to give the title compound, 54.

EXAMPLE 54

$N^3$-Benzyloxymethyl-3'-Deoxy-3'-(C-Formylmethyl)-5'-O-Tert-Butyldiphenylsilylthymidine, 55

A solution of 18 (1 mmol), $OsO_4$ (0.1 mmol) and 4-methylmorpholine N-oxide (2 mmol) in diethyl ether and water are stirred overnight. A solution of $NaIO_4$ is added and the solution further stirred. The aqueous layer is extracted with diethyl ether and the combined organic layer is evaporated under vacuum to yield the crude product, compound 55.

EXAMPLE 55

$N^3$-Benzyloxymethyl-3'-Deoxy-3'-(2-Hydroxyethyl)-5'-O-Tert-Butyldiphenylsilylthymidine, 56

Compound 55 will be treated with $NaBH_4$ to furnish the title compound 56.

EXAMPLE 56

$N^3$-Benzyloxymethyl-3'-Deoxy-3'-[Hydroxyethyl-O-(Phthalimido)]-5'-O-Tert-Butyldiphenylsilylthymidine, 57

Triphenylphosphine (6 mmol) and N-hydroxyphthalimide (6 mmol) are added to a solution of 56 in dry THF. The solution is cooled to 0° C. and diisopropylazodicarboxylate (7.5 mmol) is added dropwise over a period of 3 h while stirring under nitrogen. The reaction mixture is then stirred at room temperature for 12 h. The solution is evaporated and the residue dissolved in $CH_2Cl_2$, extracted with sat. $NaHCO_3$ and water, dried ($MgSO_4$), filtered and concentrated to furnish a crude. The residue is purified by silica gel column chromatography to give the title compound, 57.

EXAMPLE 57

$N^3$-Benzyloxymethyl-3'-Deoxy-3'-(2-Aminohydroxyethyl)-5'-O-Tert-Butyldiphenylsilylthymidine, 58

Cold methylhydrazine is added to a stirred solution of 57 in dry $CH_2Cl_2$ at 5–10° C. After addition, precipitation of 1,2-dihydro-4-hydroxy-2-methyl-1-oxophthalizine will occurred. The suspension is stirred at room temperature for 1 h. The suspension is filtered and the precipitate is washed with $CH_2Cl_2$. The combined filtrates are concentrated and the residue purified by silica gel column chromatography to furnished the title compound, 58.

EXAMPLE 58

3'-Deoxy-3'-[2-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Aminohydroxy]Ethyl]-5-O-[(1,1-Dimethylethyl)Diphenylsilyl]-3-[(Phenylmethoxy)Methyl]-Thymidine 59

(FIG. 4, Compound A, $L_3$=O, $L_4$=NH)

Compound 58 is reacted with compound 8 as per the procedure of Example 10 to yield the title dimeric compound, 59.

EXAMPLE 59

3'-Deoxy-3'-[2-[[5-(3,4-Dihydro-5-Methyl-2,4-Dioxo-1(2H)-Pyrimidinyl)Tetrahydro-3-Hydroxy-2-Furanyl]Aminohydroxy]Ethyl]-Thymidine 60

(FIG. 4, Compound D, $L_3$=O, $L_4$=NH)

Compound 59 is de-blocked as per the procedures of Examples 11, 12 and 13 to give the title compound, 60.

EXAMPLE 60

3'-Deoxy-5'-O-(Dimethoxytrityl)-3'-[2-[[5-[3,4-Dihydro-5-Methyl-2,4-Dioxo-1(2H)-Pyrimidinyl]Tetrahydro-3-Hydroxy-2-Furanyl]Aminohydroxy]Ethyl]-Thymidine 61

(FIG. 4, Compound E, $L_3$=O, $L_4$=NH)

Compound 60 is protected with a DMT group on the 5'-OH of the 5' nucleoside of this dimer as per the procedure of Example 14 to give the title compound, 61.

EXAMPLE 61

3'-Deoxy-5'-O-(Dimethoxytrity)-3'-[2-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Aminohydroxy]Ethyl]-Thymidine 62

(FIG. 4, Compound F, $L_3$=O, $L_4$=NH)

The dimer 61 is converted to its phosphoramidite as per the phosphitylation procedure of Example 15 to give the title compound, 62.

EXAMPLE 62

$N^3$-Benzyloxymethyl-3'-Deoxy-3'-(Methyloxime)-5'-O-Tert-Butyldiphenylsilylthymidine, 63

The title compound will be prepared in a manner analogous to the preparation of 3'-deoxy-3'-(methyloxime)-5'-O-tert-butyldiphenylsilylthymidine using the method described by Flandor, J and Tam. S. Y., *Tetrahedron Letts.* 1990 31, 597 by substituting compound 18 as the starting intermediate in place of compound 5 of the reference.

EXAMPLE 63

$N^3$-Benzyloxymethyl-3'-Deoxy-3'-[2-N-(Hydroxyamino)Ethyl]-5'-O-Tert-Butyldiphenylsilylthymidine, 64

Compound 64 will be reduced with sodium cyanoborohydride in THF to give the title compound, 64.

EXAMPLE 64

3'-Deoxy-3'-[2-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Hydroxyamino]Ethyl]-5-O-[(1,1-Dimethylethyl)Diphenylsilyl]-3-[(Phenylmethoxy)Methyl]-Thymidine 65

(FIG. 4, Compound A, $L_3$=NH, $L_4$=O)

Compound 64 is reacted with compound 8 as per the procedure of Example 10 to yield the title dimeric compound, 65.

EXAMPLE 65

3'-Deoxy-3'-[2-[[5-(3,4-Dihydro-5-Methyl-2,4-Dioxo-1(2H)-Pyrimidinyl)Tetrahydro-3-Hydroxy-2-Furanyl]Hydroxyamino]Ethyl]-Thymidine 66

(FIG. 4, Compound D, $L_3$=NH, $L_4$=O)

Compound 65 is de-blocked as per the procedures of Examples 11, 12 and 13 to give the title compound, 66.

EXAMPLE 66

3'-Deoxy-5'-O-(Dimethoxytrityl)-3'-[2-[[5-[3,4-Dihydro-5-Methyl-2,4-Dioxo-1(2H)-Pyrimidinyl]Tetrahydro-3-Hydroxy-2-Furanyl]Hydroxyamino]Ethyl]-Thymidine 67

(FIG. 4, Compound E, $L_3$=NH, $L_4$=O)

Compound 66 is protected with a DMT group on the 5'-OH of the 5' nucleoside of this dimer as per the procedure of Example 14 to give the title compound, 67.

EXAMPLE 67

3'-Deoxy-5'-O-(Dimethoxytrity)-3'-[2-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Hydroxyamino]Ethyl]-Thymidine 68

(FIG. 4, Compound F, $L_3$=NH, $L_4$=O)

The dimer 67 is converted to its phosphoramidite as per the phosphitylation procedure of Example 15 to give the title compound, 68.

EXAMPLE 68

$N^3$-Benzyloxymethyl-3'-Deoxy-3'-[2-O-(Tosyl)Hydroxymethyl]-5'-O-Tert-Butyldiphenylsilylthymidine, 69

Tosyl chloride is added to a solution of compound 56 in pyridine. The reaction mixture is stirred until tlc indicates disappearance of the starting material. The solid pyridine HCl is filtered and the filtrate is evaporated under vacuum. The residue purified by silica gel chromatography to give the title compound, 69.

EXAMPLE 69

$N^3$-Benzyloxymethyl-3'-Deoxy-3'-[Hydrazinoethyl]-5'-O-Tert-Butyldiphenylsilylthymidine 70

Method A. (retention the $N^3$-benzyloxymethyl blocking group)

Compound 69 will treated with anhydrous hydrazine at room temperature as per the procedure of Fikes, et. al., *J. Am. Chem. Soc.* 1992 114, 1493 to give to title compound, 70.

Method B. (with co-current removal of the $N^3$-benzyloxymethyl blocking group)

Compound 69 will treated with benzylcarbazat and activated molecular sieves (3A) in dimethylacetamide under anhydrous conditions at 110° C. utilizing the protocol of *Nucleosides & Nucleotides* 1990 9, 89. The solvent will be removed under vacuum and the residue purified by silica gel chromatography to give a 3'-(benzylcarbazat)ethyl intermediate. The intermediate carbazat is treated with palladium on charcoal in anhydrous MeOH/HCl (2% HCl by weight) under an atmosphere of hydrogen. The reaction mixture is filtered and the solvent evaporated under vacuum. The residue will be added to ethyl acetate to participate 3'-deoxy-3'-[hydrazinoethyl]-5'-O-tert-butyldiphenylsilylthymidine hydrochloride salt.

EXAMPLE 70

3'-Deoxy-3'-[2-[[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Hydrazino]Ethyl]-5-O-[(1,1-Dimethylethyl)Diphenylsilyl]-3-[(Phenylmethoxy)Methyl]-Thymidine 71

(FIG. 4, Compound A, $L_3$=NH, $L_4$=NH)

Compound 70 is reacted with compound 8 as per the procedure of Example 10 to yield the title dimeric compound, 71.

EXAMPLE 71

3'-Deoxy-3'-[2-[[5-(3,4-Dihydro-5-Methyl-2,4-Dioxo-1(2H)-Pyrimidinyl)Tetrahydro-3-Hydroxy-2-Furanyl]Hydrazino]Ethyl]-Thymidine 72

(FIG. 4, Compound D, $L_3$=NH, $L_4$=NH)

Compound 71 is de-blocked as per the procedures of Examples 11, 12 and 13 to give the title compound, 72.

EXAMPLE 72

3'-Deoxy-5'-O-(Dimethoxytrityl)-3'-[2-[[5-[3,4-Dihydro-5-Methyl-2,4-Dioxo-1(2H)-Pyrimidinyl]Tetrahydro-3-Hydroxy-2-Furanyl]Hydrazino]Ethyl]-Thymidine 73

(FIG. 4, Compound E, $L_3$=NH, $L_4$=NH)

Compound 72 is protected with a DMT group on the 5'-OH of the 5' nucleoside of this dimer as per the procedure of Example 14 to give the title compound, 73.

EXAMPLE 73

3'-Deoxy-5'-O-(Dimethoxytrity)-3'-[2-[[5-[3,4-Dihydro-5-Methyl-2,4-Dioxo-1(2H)-Pyrimidinyl]Tetrahydro-3-[(β-Cyanoethoxy)-N-(Diisopropyl)Phosphiryl]-3-Hydroxy-2-Furanyl]Hydrazino]Ethyl]-Thymidine 74

(FIG. 4, Compound F, $L_3$=NH, $L_4$=NH)

The dimer 73 is converted to its phosphoramidite as per the phosphitylation procedure of Example 15 to give the title compound, 74.

EXAMPLE 74

1-[3-Azido-4-[-O-Tert-Butyldiphenylsilyl(Hydroxymethyl)]-Cyclopentyl]-5-Methyl-3-[(Phenylmethoxy)Methyl]-2,4-(1H,3H)-Pyrimidindione 76

(Carbocyclic analog of 3-azido thymidine)

(+)-1-[1R,3S,4S)-3-azido-4-(hydroxymethyl)-cyclopentyl]-5-methyl-2,4-(1H,3H)-pyrimidindione (75) is prepared as per the procedure of Bodenteich, M. and Griengl, H., *Tetrahedron Letts.* 1987 28, 5311. This 3-azido carbocyclic analogue of thymidine will be treated as per the procedures of Examples 1 and 2 to blocking both the base portion and the 5'-hydroxy moiety of the pseudo sugar portion to give the title compound, 76.

EXAMPLE 75

1-[3-Amino-4-[-O-Tert-Butyldiphenylsilyl(Hydroxymethyl)]-Cyclopentyl]-5-Methyl-3-[(Phenylmethoxy)Methyl]-2,4-(1H,3H)-Pyrimidindione 77

(Carbocyclic analog of protected 3-amino thymidine)

Compound 76 will be treated as per procedure vii of Hronowski, L. J. J. and Szarek, W. A., *J. Chem. Soc., Chem. Commun.* 1990 1547 to give the 3-amino analogue, compound 77.

EXAMPLE 76

1-[3-[N-[2-Ethyl-(N-Phthalimido)]]-Amino-4-[-O-Tert-Butyldiphenylsilyl(Hydroxymethyl)]-Cyclopentyl]-5-Methyl-3-[(Phenylmethoxy)Methyl]-2,4-(1H,3H)-Pyrimidindione 78

Compound 77 will be treated with N-(β-chloroethyl) phthalimide (Chem Service Inc., West Chester, Pa.) to give the title compound, 78.

EXAMPLE 77

1-[3-[Amino-(2-Aminoethyl)]-4-[-O-Tert-Butyldiphenylsilyl(Hydroxymethyl)]-Cyclopentyl]-5-Methyl-3-[(Phenylmethoxy)Methyl]-2,4-(1H,3H)-Pyrimidindione 79

Compound 78 will be treated with 5% methylhydrazine in $CH_2CCl_2$ to give the title compound, 79.

EXAMPLE 78

1-[3-[Amino-[2-[3-(Benzoyloxy)-5-[3,4-Dihydro-5-Methyl-2,4-Dioxo-3-[(Phenylmethoxy)Methyl]-1(2H)-Pyrimidinyl]Tetrahydro-2-Furanyl]Amino] Ethyl]-3-[(Phenylmethoxy)Methyl]-4-[-O-Tert-Butyldiphenylsilyl(Hydroxymethyl)]-Cyclopentyl]-5-Methyl-3-[(Phenylmethoxy)Methyl]-2,4-(1H,3H)-Pyrimidindione 80

(FIG. 4, Compound A where the 5' nucleoside is a carbocyclic nucleoside analogue, $L_1$=NH, $L_4$=NH)

Compound 79 is reacted with compound 8 as per the procedure of Example 10 to yield the title dimeric compound, 80.

EXAMPLE 79

1-[3-[Amino-[2-[3-Hydroxy-5-[3,4-Dihydro-5-Methyl-2,4-Dioxo-1(2H)-Pyrimidinyl]Tetrahydro-2-Furanyl]Amino]Ethyl]-4-Hydroxymethyl-Cyclopentyl]-5-Methyl-2,4-(1H,3H)-Pyrimidindione 81

Compound 80 is de-blocked as per the procedures of Examples 11, 12 and 13 to give the title compound, 81.

EXAMPLE 80

$N^3$-Benzyloxymethyl-3'-Deoxy-3'-Thiol-5'-O-(Dimethoxytrityl)Thymidine 82

In a modification of the procedure of Cosstick, R. and Vyle, J. S. *Nucleic Acids Research* 1990 18, 829 thymidine is dimethoxytritylated using the protocol of the reference followed by blockage of the heterocyclic base as per the procedure of Example 2 above to afford the intermediate $N^2$-benzyloxymethyl-5'-O-dimethoxytrityl thymidine. This intermediate is then further treated as per the Cosstick and Vyle reference to give the title compound, 82.

EXAMPLE 81

$N^3$-Benzyloxymethyl-3'-Deoxy-3'-[(2-N-Phthalimidoethyl)Thio]-5'-O-(Dimethoxytrityl) Thymidine 83

Compound 82 will be treated with N-(β-chloroethyl) phthalimide (Chem Service Inc., West Chester, Pa.) to give the title compound, 83.

EXAMPLE 82

$N^3$-Benzyloxymethyl-3'-Deoxy-3'-[(2-Aminoethyl) Thio]-5'-O-(Dimethoxytrityl)Thymidine 84

Compound 83 will be treated with 5% methylhydrazine in $CH_2Cl_2$ to give the title compound, 84.

EXAMPLE 83

3'-Deoxy-5'-(Dimethoxytrityl)-3'-Thio-[2-[[3-(Benzoyloxy)-5-[3,4-Dihydro-5-Methyl-2,4-Dioxo-3-[(Phenylmethoxy)Methyl]-1(2H)-Pyrimidinyl] Tetrahydro-2-Furanyl]Amino]Ethyl]-3-[(Phenylmethoxy)Methyl]-Thymidine 85

(FIG. 4, Similar to Compound A except has DMT instead of TBDPS group, $L_1$=S, $L_4$=NH)

Compound 84 is reacted with compound 8 as per the procedure of Example 10 to yield the title dimeric compound, 85.

EXAMPLE 84

3'-Deoxy-5'-O-(Dimethoxytrityl)-3'-Thio-[2-[[3-(Benzoyloxy)-5-[3,4-Dihydro-5-Methyl-2,4-Dioxo-1 (2H)-Pyrimidinyl]Tetrahydro-3-Hydroxy-2-Furanyl] Amino]Ethyl]-Thymidine 86

(FIG. 4, Similar to Compound B except has DMT instead of TBDPS group, $L_1$=S, $L_4$=NH)

The BOM group of compound 85 is de-blocked as per the procedure of Example 11 to give the title compound, 86.

EXAMPLE 85

3'-Deoxy-5'-O-(Dimethoxytrityl)-3'-Thio-[2-[[5-[3,4-Dihydro-5-Methyl-2,4-Dioxo-1(2H)-Pyrimidinyl] Tetrahydro-3-Hydroxy-2-Furanyl]Amino]Ethyl]-Thymidine 87

(FIG. 4, Compound E, $L_1$=S, $L_4$=NH)

The benzoyl group of compound 86 is de-blocked as per the procedure of Example 12 to give the title compound, compound 87, having a DMT group on the 5'-OH of the 5' nucleoside of the dimer.

EXAMPLE 86

3'-Deoxy-5'-O-(Dimethoxytrity)-3'-Thio-[2-[[5-[3,4-Dihydro-5-Methyl-2,4-Dioxo-1(2H)-Pyrimidinyl] Tetrahydro-3-[(β-Cyanoethoxy)-N-(Diisopropyl) Phosphiryl]-3-Hydroxy-2-Furanyl]Amino]Ethyl]-Thymidine 88

(FIG. 4, Compound F, $L_1$=S, $L_4$=NH)

The dimer 87 is converted to its phosphoramidite as per the phosphitylation procedure of Example 15 to give the title compound, 88.

EXAMPLE 87

$N^3$-Benzyloxymethyl-3'-O-(2-Chloroethyl)-5'-O-Tert-Butyldiphenylsilylthymidine, 89

Compound 10 is converted to the chloroethyl derivative with triphenylphosphine and carbon tetrachloride in DMF via the procedure of Verheydan, J. P. H. and Moffatt, J. G. *J. Org. Chem.* 1972 37, 2289 to give the title compound, 89.

EXAMPLE 88

$N^3$-Benzyloxymethyl-3'-Deoxy-(3-Chloropropyl)-5-O-Tert-Butyldiphenylsilylthymidine, 90

Compound 39 is converted to the chloropropyl derivative with triphenylphosphine and carbon tetrachloride in DMF via the procedure of Verheydan, J. P. H. and Moffatt, J. G. *J. Org. Chem.* 1972 37, 2289 to give the title compound, 90.

EXAMPLE 89

1-[3-Benzoyloxy-4-(Selenourido)-Tetrahydro-2-Furanyl]-5-Methyl-3-[(Phenylmethoxy)Methyl]-2,4-(1H,3H)-Pyrimidindione Hydrochloride 91

Compound 8 will be treated with seleno-urea utilizing protocol i) of Benhaddou, R., Czernecki, S. and Randriamandimby, D., *SYNLETT* Dec. 1992, 967 to give the title compound, 91.

EXAMPLE 90

Diselenide of [1-(3-Hydroxy-5-Seleno-Tetrahydro-2-Furanyl)-5-Methyl-3-[(Phenylmethoxy)Methyl]-2,4-(1H,3H)-Pyrimidindione]92.

Compound 91 will be treated with KOH utilizing protocol ii) of Benhaddou, R., Czernecki, S. and Randriamandimby, D., *SYNLETT Dec.* 1992, 967. The benzyl blocking group is removed concurrently with the formation of the diselenide to give the title compound, 92.

EXAMPLE 91

3'-O-[2-[[3-Hydroxy-5-[3,4-Dihydro-5-Methyl-2,4-Dioxo-3-[(Phenylmethoxy)Methyl]-1(2H)-Pyrimidinyl]Tetrahydro-2-Furanyl]Seleno]Ethyl]-5-O-[(1,1-Dimethylethyl)Diphenylsilyl]-3-[(Phenylmethoxy)Methyl]-Thymidine 93

(FIG. 4, Compound A, $L_1$=O, $L_4$=Se)

Compound 92 is reacted with compound 89 utilizing protocol iii) of Benhaddou, R., Czernecki, S. and Randriamandimby, D., *SYNLETT Dec.* 1992, 967 to give the title dimeric compound, 93.

EXAMPLE 92

3'-Deoxy-[3-[[3-Hydroxy-5-[3,4-Dihydro-5-Methyl-2,4-Dioxo-3-[(Phenylmethoxy)Methyl]-1(2H)-Pyrimidinyl]Tetrahydro-2-Furanyl]Seleno]Propyl]-5-O-[(1,1-Dimethylethyl)Diphenylsilyl]-3-[(Phenylmethoxy)Methyl]-Thymidine 94

(FIG. 4, Compound A, $L_4$=Se)

Compound 92 is reacted with compound 90 utilizing protocol iii) of Benhaddou, R., Czernecki, S. and Randriamandimby, D., *SYNLETT Dec.* 1992, 967 to give the title dimeric compound, 94.

EXAMPLE 93

3'-O-(Tert-Butyldiphenylsilyl)-Thymidine 95

Thymidine was converted to its 5'-O-trityl derivative with trityl chloride in pyridine in the normal manner followed by blocking of the 3'-hydroxyl with a t-butyldiphenylsilyl group utilizing the protocol of Example 1. Treatment with aqueous acetic acid at 80° C. gives the title compound, 95.

EXAMPLE 94

3-O-(Tert-Butyldiphenylsilyl)-Thymidine-5'-Carboxylic Acid 96

Compound 95 (200 mg., 0.42 mmol) was suspended in KOH (1 N. 5 mL). Potassium persulfate (0.45 g, 1.66 mmol, 4 eq) and ruthenium (III) chloride (several mg) were added. The reaction was stirred at RT for 2 hr. The mixture is filtered and the filtrated diluted with HCl (0.1 N) to pH 6 followed by extraction with $CH_2Cl_2$ (2×20 mL). The organic layer was dried over $MgSO_4$ and evaporated under reduced pressure. The residue was purified by silica gel chromatography using $CH_2Cl_2 \rightarrow 2\%$ MeOH (with 0.5% AcOH added) to give the product, 96. $^1$H NMR ($CDCl_3$+1 drop DMSO.d6) $\delta$8.82 (s, 1, NH); 8.12 (s, 1, H-6); 7.61 (d, 4, $C_6H_5$); 7.32–7.45 (m, 6, $C_6H_5$); 6.61 (t, 1, H-1); 4.60 (d, 1 H-3'); 4.58 (s, 1, H-4'); ≈2.60 (br, 1 ROOH); 2.18 (dd, 1, H-2'); 1.72 (dd, 1, H-2"); 1.86 (s, 3, $CH_3$) and 1.08 (s, 9, T-Bu).

EXAMPLE 95

1-[5-(Acetyloxy)-4(Tert-Butyldiphenylsilyl)-Tetrahydro-2-Furanyl]-5-Methyl-2,4(1H,3H)-Pyrimidindione 97

Compound 96 (1.66 g, 3.58 mmol) was treated with $Pb(OAC)_4$ (2.06 g, 4.65 mmol) as per the procedure of Example 7 to give 1.21 g (70.8%) of the title compound, 97.

EXAMPLE 96

1-[5-(Hydroxy)-4 (Tert-Butyldiphenylsilyl)-Tetrahydro-2-Furanyl]-5-Methyl-2,4(1H,3H)-Pyrimidindione 98

Compound 97 is treated as per the protocol of Baptistella et. al., *Synthesis* 1989, 436 with DBU to give the title compound, 98. The compound was identified by a reduction in its $R_f$ on a TLC. The compound proved to be unstable to isolation. It is therefore further used directly in situ following its preparation.

EXAMPLE 97

1-[5-(Chloro)-4(Tert-Butyldiphenylsilyl)-Tetrahydro-2-Furanyl]-5-Methyl-2,4(1H,3H)-Pyrimidindione 99

Compound 96 is treated with lead tetracetate and lithium chloride as per the procedure of Kochi, J. K. *J. Am. Chem. Soc.* 1965 87, 2502 or with lead tetracetate and N-chlorosuccinimide as per the procedure of Wang et. al., *Tet. Asym.* 1990 1, 527 or Wilson et. al., *Tet. Asym.* 1990 1, 525 to give the title compound, 99.

EXAMPLE 98

3'-Deoxy-3'-Hydroxymethyl-5'-O-(Tertbutyldiphenylsilyl)Thymidine 100

In a variation of the procedure of Debart, F., Vasseur, J.-J., Sanghvi, Y. S. and Cook, P. D., *Bioorganic & Medicinal Chemistry Letts.* 1992, 2 1479, 5'-O-(tert-butyldiphenylsilyl) thymidine is substituted for the 5'-O-trityl thymidine starting material of the reference to prepare the title compound, 100.

EXAMPLE 99

3'-Deoxy-3'-(Methylthiomethylhydroxymethyl)-5'-O-(Tert-Butyldiphenylsilyl)Thymidine 101

Compound 100 is treated as per the procedure of Step 1 of Example 1 of PCT published application WO 91/06629 (or via the procedure of Mattecuui, M., *Tet. Letts.* 1990 31, 2385) to give the title compound, 101.

EXAMPLE 100

3'-Deoxy-5'-O-(Dimethoxytrityl)-3'-Methyl-[O-[[5-[3,4-Dihydro-5-Methyl-2,4-Dioxo-1(2H)-Pyrimidinyl]Tetrahydro-3-Hydroxy-2-Furanyl]Oxy] Hydroxymethyl]-Thymidine 102

(FIG. 4, Compound E, $L_2$=O, $L_4$=O)

Compounds 101 and 98 will be reacted as per the procedure of Steps 2 and 3 of Example 1 of PCT published application WO 91/06629 followed deblocking of both the 3' and 5' (tert-butyldiphenylsilyl) blocking groups utilizing the procedure of Example 13 to give an intermediate corresponding to compound E of FIG. 4. The intermediate is treated as per the procedure of Example 14 to give the title compound, 102.

EXAMPLE 101

3'-Deoxy-3'-(Thiomethylhydroxymethyl)-5'-O-(Tert-Butyldiphenylsilyl)Thymidine 103

Compound 100 will be treated with chloromethyl-t-butyl mercaptan to form the intermediate 3'-deoxy-3'-(tert-butylthiomethylhydroxymethyl-5'-O-(tert-butyldiphenylsilyl)thymidine followed by treatment with 5% trifluoroacetic acid to give the title compound, 103. Alternately this compound can be prepared as per the procedure of Divakar, et. al., *J. Chem. Soc. Perkin. Trans.* 1 1990, 969.

EXAMPLE 102

3'-Deoxy-5'-O-(Dimethoxytrityl)-3'-Methyl-[O-[[5-[3,4-Dihydro-5-Methyl-2,4-Dioxo-1(2H)-Pyrimidinyl]Tetrahydro-3-Hydroxy-2-Furanyl]Thio] Hydroxymethyl]-Thymidine 104

(FIG. 4, Compound E, $L_2$=O, $L_4$S)

Compound 103 is reacted with compound 8 as per the procedure of Example 10 to yield the 5'-xytrityl equivalent of compound B of FIG. 4. Removal of the BOM, the benzoyl and tert-butyldiphenylsilyl blocking groups will be effected as per the procedures of Examples 11, 12 and 13 to give an intermediate corresponding to compound D of FIG. 4. This intermediate is treated as per the procedure of Example 14 to give the title compound, 104.

EXAMPLE 103

3'-Deoxy-3'-(C-Formyl)-5'-O-(Tert-Butyldiphenylsilyl)Thymidine 105

The compound was identified by a reduction in its $R_f$ on a TLC. The compound proved to be unstable to isolation. It is therefore further used directly in situ following its preparation.

In a variation of the procedure of Debart, F., Vasseur, J.-J., Sanghvi, Y. S. and Cook, P. D., *Bioorganic & Medicinal Chemistry Letts.* 1992, 2 1479, 5'-O-(tert-butyldiphenylsilyl) thymidine is substituted for the 5'-O-trityl thymidine starting material of the reference to prepare the title compound, 105.

EXAMPLE 104

3'-Deoxy-3'-Hydroxymethyl-5'-O-(Tert-Butyldiphenylsilyl)Thymidine 106

Compound 105 (4.0 g, 8.12 mmol) was dissolved in 100 ml of an 8:2 (v/v) mixture of ethanol and water. The reaction was cooled to 0° C. and sodium borohydride (1.08 g, 28.6 mmol) was added portionwise. The mixture was allowed to warm up to room temperature. The completion of the reaction (3 hours) was monitored by tlc in MeOH/$CH_2Cl_2$ (1:9). The reaction mixture was then poured onto 150 ml of ice-cold water, extrated twice with ethyl acetate (150 ml), and dried over anhydrous $MgSO_4$. The solvent was evaporated in vacuo and the residue was purified by silica gel flash column chromatography in EtOAc/$CH_2Cl_2$ (2:8–9:1, v/v) to afford 2 (2.73 g, 68%) as a white foam. Tlc ($R_f$ 0.52; EtOAc); $^1$H NMR (CDCl$_3$): δ8.88 (br, 1 H, NH), 7.69–7.66 (m, 4 H, Ph), 7.47–7.39 (m, 6 H, Ph), 7.37 (d, 1 H, J=1.1 Hz, H-6), 6.14 (dd, 1 H, J=5.7 Hz, J=6.7 Hz, H-1'), 4.02 (dd, 1 H, J=11.1 Hz, J=3.0 Hz, H-5'), 3.99–3.91 (m, 1 H, H-4'), 3.84 (dd, 1H, J=11.1 Hz, J=3.0 Hz, H-5"), 3.81–3.64 (m, 2 H, CH$_2$OH), 2.61–2. 59 (m, 1 H, H-3'), 2.38–2.29 (m, 2 H, OH & H-2'), 2.16–2.14 (m, 1 H, H-2"), 1.64 (s, 3 H, CH$_3$), 1.10 (s, 9 H, C(CH$_3$)$_3$),; $^{13}$C NMR (CDCl$_3$): δ163.7 (C4), 150.3 (C2), 135.5–135.4 (d), 132.9, 132.4, 130.1 (C6), 127.9, 110.8 (C5), 84.8 (C1'), 83.2 (C4'), 64.9 (CH$_2$OH), 63.3 (C5'), 41.6 (C3'), 35.5 (C2'), 26.9, 19.3, 12.2; FAB MS m/z 495 (MH$^+$); Anal. Calcd for $C_{2\_}H_{34}N_2O_5Si$ (494.662): C, 65.56; H, 6.93; N, 5.66; Si, 5.68. Found: C, 65.06; H 7.01; N, 5.60; Si, 5.82.

EXAMPLE 105

3'-Deoxy-3'-methyl-[(β-cyanoethoxy)-N-(diisopropyl)phosphiryl]-5'-O-(tert-butyldiphenylsilyl)thymidine 107.

Compound 106 is treated with tetrazole diisopropylamine salt (35 mg, 0.2 mmol) and 2-cyanoethyl-N,N,N',N'-tetra-isopropylphosphorodiamidite as per Example 15 to give the title compound, 107.

EXAMPLE 106

3'-Deoxy-3'- [2-[[3-(tert-butyldiphenylsilyl)-5-[3,4-dihydro-5-methyl-2, 4 -dioxo-1(2H) -pyrimidinyl] tetrahydro-2-furanyl]oxy][(β-cyanoethoxy) (oxyphosphiryl)]]-5'-O-(tert-butyl-diphenylsilyl)]-thymidine 108.

Compound 107 will be reacted with compound 98 in a acetonitrile solution the manner utilized for normal solid, state oligonucleotide synthesis (see *Oligonucleotide synthesis, a practical approach,* Gait, M. J. Ed, IRL Press, Oxford Press 1984) to give the title compound, 108.

EXAMPLE 107

3'-Deoxy-3'[2-[[3-(tert-butyldiphenylsilyl)-5-[3,4-dihydro-5-methyl-2,4-dioxo-1(2H)-pyrimidinyl]tetrahydro-2-furanyl]oxy][oxyphosphate]]-5'-O-[(1,1-dimethylethyl) diphenylsilyl]-thymidine 109

The $P^{III}$ compound 108 from Example 106 will be oxidized to the $p^V$ phosphate in the normal manner utilized for norma:L solid state oligonucleotide synthesis (see *Oligonucleotide synthesis, a practical approach,* Gait, M. J. Ed, IRL Press, Oxford Press 1984) to give the title compound, 109.

EXAMPLE 108

3 '-Deoxy-3-[[[3-(tert-butyldiphenysilyl)-5-[3,4-dihydro-5-methyl-2,4-dioxo-1(2H)-pyrimidinyl]tetrahydro-2-furanyl]oxy][thiophosphate]]-5'-O-[(1,1-di-methylethyl) diphenylsilyl]-thymidine 110

The $P^{III}$ compound 108 from Example 106 will be oxidized with the Beaucage reagent to the pV thiophosphate in the normal manner utilized for normal solid state phosphorothioate oligonucleotide synthesis (see *Oligonucleotide synthesis, a practical approach,* Eckstein, F. Ed, IRL Press, Oxford Press, 1991) to give the title compound, 110.

EXAMPLE 109

3'-Deoxy-3-[[[3-(tert-butyldiphenylsilyl)-5-[3,4-dihydro-5-methyl -2,4-dioxo-1(2H)-pyrimidinyl]tetrahydro-2- furanyl]oxy][methoxyphosphate]]-5'-O-(tert-butyldiphenylsilyl)-thymidine 111

In a manner analogous to Examples 105, 106 and 107 the phosphotriester analogue 111 is prepared utilizing the teaching of Sproat, B. S. and Gail, M. J., Chapter 4, *Oligonucleotide synthesis, a practical approach,* Gait, M. J. Ed, IRL Press, Oxford Press 1984, page 83.

EXAMPLE 110

3'-Deoxy-3-[[[3-tertbutyldiphenylsilyl)-5-[3,4-dihydro-5-methyl-2,4-dioxo-1(2H)-pyrimidinyl]tetrahydro-2-furanyl]oxy][-(methyl)phosphonate]]-5'-O-(tertbutyldiphenylsilyl)-thymidine 112

In a manner analogous to Examples 105, 106 and 107 the methyl phosphonate analogue 112 is prepared utilizing the teaching of Miller, P. S., Cushman, C. D. and Levis, J. T., Chapter 6, *Oligonucleotide synthesis, a practical approach,* Eckstein, F. Ed, IRL Press, Oxford Press 1991, page 137.

EXAMPLE 111

3'-Deoxy-3'-iodomethyl-5'-O-(tert-butyldiphenylsilyl)thymidine 113.

To a stirred solution of 106 in DMF is added methyltriphenoxyphosphonium iodide under argon at room temperature. After the reaction is completed, the solvent is evaporated under vacuum and the residue dissolved in $CH_2Cl_2$, washed with 20% aqueous $Na_2S_2O_3$, water and dried. The residue is purified by silica gel chromatography to give the title compound, 113.

EXAMPLE 112

3'-Deoxy-3'-[2-(phosphono)ethyl]-5'-O-(tert-butyldiphenyl-silyl)thymidine diphenylester 115.

Compound 105 (1.0 g, 2.03 mmol) was co-evaporated twice with dry pyridine and diphenyl triphenyl phosphoranylidene methyl phosphonate (2.2 g, 4.62 mmol) was added under an atmosphere of argon. The mixture was dissolved in anhydrous dimethyl sulfoxide (11 ml), and the reaction was stirred at room temperature overnight. Tlc showed that only part of the starting material had been converted into a new product. The reaction mixture was warmed at 50° C. for ca. 2 hours and quenched with 30 ml of ice-water. Dichloromethane (50 ml) was added to the white cloudy mixture and stirred for 30 min. The organic layer was then washed with saturated $NaHCO_3$ and saturated NaCl and dried over $MgSO_4$ then concentrated in vacuo. The residue was purified by silica gel flash column chromatography with $EtOAc/CH_2Cl_2$ (1:9–3:7, v/v) to give 114 (0.98 g, 67%) as a white foam. $^1$H NMR (CDCl$_3$):δ8.36 (br, 1 H, NH), 7.68–7.61 (m, 4 H, Ph), 7.49–7.13 (m, 17 H, H-6 & Ph), 6.68–6.92 (m, 1 H, C—CH=C$\underline{H}$—P), 6.15 (m, 1 H, H-1'), 6.10–5.89 (m, 1 H, C—C=C$\underline{H}$—P), 4.11–4.04 (m, L H, H-5'), 3.70–3.65 (m, 1 H, H-5"), 3.86–3.80 (m, 1 H, H-4'), 3.41–3.21 (m, 1 H. H-3'), 2.42–2.29 (m, 2 H, H-2' & H-2"), 1.64 (s, 3 H, CH$_3$) , 1.10 (s, 9 H, C(CH$_3$)$_3$); $^{31}$p NMR (CDCl$_3$): δ+10.29 (s).

Compound 114 (3.4 g, 4.70 mmol) was hydrogenated over 10% Pd/C (1.0 g) in EtOH (100 ml) at room temperature for 16 hours. The reaction mixture was filtered through a celite pad and the solid was washed with dichloromethane. The combined filtrates and washings were concentrated in vacuo to give a white foam, which was further purified by silica gel flash column chromatography with EtOAc/Hexane (4:6–9:1, v/v) to yield the title compound, 115, (2.41 g, 71%). $^1$H NMR (CDCl$_3$):δ 8.60 (s, 1 H, NH), 7.68–7.30 (m, 4 H, Ph), 7.53 (d, 1 H, J=1.7 Hz, H-6), 7.50–7.27 (m, 12 H, Ph), 7.20–7.10 (m, 4 H, Ph), 6.12 (dd, 1 H, J=4.4 Hz, J=6.7 Hz, H-1'), 4.06 (d, 1 H, J=9.2 Hz, H-5'), 3.80–3.74 (m, 2 H, H-5' & H-4'), 2.51–2.42 (m, 1 H, H-3'), 2.29–2.23 (m, 1 H, H-2'), 2.18–2.18–2.10 (m, 1 H, H-2"), 2.09–1.95 (m, 4 H, C—C$\underline{H}_2$—C$\underline{H}_2$—P), 1.62 (s, 3 H, CH$_3$) , 1.09 (s, 9 H, C(CH$_3$)$_3$); $^{13}$C NMR (CDCl$_3$): δ163.6 (C4) 150.2 (C2), 135.5–135.2 (d), 132.9–132.5 (d), 132.1–131.9 (d), 130.1 (C6), 130.0–129.8 (d), 128.5–128.4 (d), 128.4–127.9 (d) , 125.3 120.4, 110.6 (C5), 85.7 (C1'), 84.7 (C4') 63.8 (C5'), 38.5 (C3'), 38.3 (C2'), 27.0, 19.4; $^{31}$P NMR (CDCl$_3$): δ+22.1 and +29.5 (ratio 64:36).

EXAMPLE 113

3'-Deoxy-3'-[2-(phosphono)ethyl]-5'-O-(tert-butyldiphenyl-silyl)thymidine 116.

Compound 115 (0.21 g, 0.29 mmol) was dissolved in 15 ml of a 2:1 (v/v) mixture of THF and water. The pH of the reaction was adjusted between 11 and 12 with 1 N sodium hydroxide. The reaction was then stirred at room temperature for 48 hours. After completion of the reaction, as was monitored by tlc in EtOAc, the reaction was neutralized with a Dowex 50 W cation exchange resin (H$^+$form) . The resin was filtered off and washed well with methanol. The combined filtrates and washings were concentrated in vacuo, and co-evaporated with acetonitrile to give a yellow solid. The residue was purified by silica gel flash column chromatography in $CH_2Cl_2/CH_3OH$ (98:2–90:10) to give 116 (60 mg, 32%) . $^1$H NMR (DMSO): δ10.7 (br, 1 H, NH), 7.63–7.59 (m, 4 H, Ph), 7.40–6.90 (m, 12 H, Ph), 6.02–5.99 (m, 1 H, H1'), 3.86–3.84 (m, 1 H, H5'), 3.62–3.59 (m, 1 H, H5'), 3.50–3.21 (br, 3 H, H5" & OH), 2.25–2.16 (m, 1 H, H3'), 2.04–1.99 (m, 1 H, H2'), 1.80–1.72 (m, 1 H, H2"), 1.62–1.55 (m, 2 H, C—CH$_2$—CH$_2$—P), 1.50 (s, 3 H, CH$_3$) , 1.00 (s, 9 H, C(CH$_3$)$_3$) ; $^{13}$C NMR (DMSO): δ163.7 (C4), 150.2 (C2), 134.8, 132.7, 132.2, 129.4 (C6), 128.5, 127.3, 122.2 119.9, 109.5 (C5), 84.9 (C1'), 83.7 (C4'), 64.0 (C5'), 38.9 (C3'), 37.2 (C2'), 26.4, 18.7, 11.6; $^{31}$P NMR (DMSO): δ+20.7 (s).

EXAMPLE 114

1-[5-O-(trichloroacetylimido)-4-(tert-butyldiphenylsilyl)tetra-hydro-2-furanyl]-5-methyl-3-[(phenylmethoxy)methyl]-2,4(1H,3H)-pyrimidindione 117.

Compound 96 is treated with trichloroacetonitrile and sodium hydride as per the procedure of Schmidt, R. R. Angew. *Chem. Int. Engl.* 1986 25, 212, to give the title compound, 117.

EXAMPLE 115

3'-Deoxy-3-[[[(3-(tert-butyldiphenylsilyl)-5-[3,4-dihydro-5-methyl-2,4-dioxo-1(2H)-pyrimidinyl]tetrahydro-2-furanyl]oxy]-ethylphosphate]-5'-O-(t-ert-butyldiphenylsilyl)-thymidine 118

The reaction mixture of compound 98 (prepared in situ) is treated with trichloroacetonitrile and Compounds 116 and 117 are reacted together in the manner of Schmidt, R. S., Braun, H. and Jung, K. -H., *Tetrahedron Letts.* 1992 33 1585 to give the title compound, 118.

EXAMPLE 116

3'-Deoxy-3'-(3-mercaptomethyl)-5'-O-tert-butyldiphenylsilyl-thymidine 119.

Compound 106 will be treated as per Examples 24 and 25 to yield the title compound, 119.

EXAMPLE 117

3'-Deoxy-3'-[3-mercaptomethyl((β-cyanoethoxy)-N-(diisopropyl)-phosphiryl)-5'-O-tert-butyldiphenylsilylthymidine 120.

Compound 106 will be treated 2-cyanoethyl N,N-diisopropylmonochlorophosphoramidite as per the procedure of Cosstick, R. and Vyle, J. S. *Nucleic Acids Research* 1990 18, 829 to yield the title compound, 120.

EXAMPLE 118

3'-Deoxy-5'-O-(tert-butyldiphenylsilyl)-3'-[[[3-(tert-butyldi-phenylsilyl)-5-[3,4-dihydro-5-methyl-2,4-dioxo-1(2H)-pyrim-idinyl]tetrahydro-2-furanyl]oxy][(β-cyanoethoxy)(methylthiophosphiryl)]]-thymidine 121

Compound 120 will be reacted with compound 98 as per the procedure of Cosstick, R. and Vyle, J. S. *Nucleic Acids Research* 1990 18, 829 to give the title compound 121.

EXAMPLE 119

3'-Deoxy-5'-(tert-butyldiphenylsilyl)-3'-[[[3-(tert-butyldi-phenylsilyl)-5-[3,4-dihydro-5-methyl-2,4-dioxo-1(2H)-pyrim-idinyl]tetrahydro-2-furanyl]oxy][β-cyanoethoxy)(methylthiolphosphate)]]-thymidine 122

The $P^{III}$ compound 121 from Example 118 will be oxidized to the $p^V$ phosphate using tetrabutylammonium periodate as the oxidization agent to give the title compound, 122.

EXAMPLE 120

3'-Deoxy-5'-(tert-butyldiphenylsilyl)-3'-[[[3-(tert-butyldiphenylsilyl)-5-[3,4-dihydro-5-methyl-2,4-dioxo-1(2H)-pyrimidinyl]tetrahydro-2-furanylloxy][(β-cyanoethoxy)(methyl-thiothiophosphate)]]-thymidine 123

The $P^{III}$ compound 121 from Example 118 will be oxidized with sulfur to the $P^V$ thiophosphate as per the procedure of Cosstick, R. and Vyle, J. S. *Nucleic Acids Research* 1990 18, 829 to give the title compound 123.

EXAMPLE 121

1-[5'-(2-methoxy-2-oxy-ethylthio)-4'-benzoyloxy-tetrahydrofuran-2'-yl]-$N^3$-benzoxymethylthymine, 124.

Compound 8 is reacted with methylthioglycolate (Aldrich Chemical) in the manner of Example 10 to yield the title compound, 124.

EXAMPLE 122

1-[5'-(2-hydroxy-ethylthio)-4'-benzoyloxy-tetrahydrofuran-2'-yl]-$N^3$-benzoxymethylthymine, 125.

Compound 124 will be reduced with $NaBH_4$ as per the procedure of Taniguchi, M., Koga, K. and Yamada, S. *Tetrahedrcn* 1974 30, 3574 to give the title compound, 125.

EXAMPLE 123

Xyloadenosine 126.

Method A—Condensation Reaction

Adenine is condensed with 1,2,3,5-tetra-O-acetyl-D-xylopentofuranoside in the presence of $TiCl_4$ as the condensation catalyst in a polar solvent utilizing the method of Szarek, W. A., Ritchie, R. G. S., and Vyas, D. M. (1978), *Carbohydr. Res.,* 62:89.

Method B—Alkylation Reaction

8-Mercaptoadenine is alkylated with 5-deoxy-5-iodo-1,2-O-isopropylidine-xylofuranose followed by treatment with acetic acid/acetic anhydride/sulfuric acid and then ammonia. This yields an 8–5'-anhydro intermediate nucleoside that is oxidized with aqueous N-bromosuccinimide to give the sulfoxide. This is blocked with benzoic anhydride and after a Pummerer rearrangement can be desulfurized with Raney nickel to give 9-β-D-xylofuranosyladenine as per the procedure of Mizuno, Y., Knaeko, C., Oikawa, Y., Ikeda, T, and Itoh, T. (1972), *J. Am. Chem. Soc.,* 94:4737.

EXAMPLE 124

3-Deaza-9-(β-D-threo-pentofuranosyl)guanine 127.

In a manner similar to Example 123, Method A, 3-deazaguanine is condensed with 1,2,3,5-tetra-O-acetyl-D-xylopentofuranoside to yield the title compound.

EXAMPLE 125

$N^6$-Benzoyl-9-(2'-Deoxy-2'-fluoro-β-D-threo-pentofuranosyl)adenine 128.

In a manner similar to Example 123, Method A, $N^6$-benzoyladenine is condensed with 1,3,5-tri-O-acetyl-2-deoxy-2-fluoro-D-threo-pentofuranoside to yield the title compound.

EXAMPLE 126

1-(2'-Deoxy-2'-methoxy-β-D-threo-pentofuranosyl) uridine 129.

In a manner similar to Example 123, Method A, uracil iscondensedwithl,3,5-tri-O-acetyl-2-deoxy-2-methoxy-D-threo-pentofuranoside to yield the title compound.

EXAMPLE 127

1-(2'-Deoxy-2'-O-allyl-β-D-threo-pentofuranosyl) cytosine 130.

In a manner similar to Example 123, Method A, cytosine is condensed with 1,3,5-tri-O-acetyl-2-deoxy-2-O-allyl-D-threo-pentofuranoside to yield the title compound.

EXAMPLE 128

Xyloguanosine 131.

Method A

In a manner similar to Example 123, Method A, guanine is condensed with 1,2,3,5-tetra-O-acetyl-D-xylopentofuranoside to yield the title compound.

Method B

The chloromercury derivative of 2-acetamido-6-chloropurine is condensed with 2,3,5-tri-O-acetyl-β-D-ribofuranosylpurine utilizing the method of Lee et. al. (1971),*J. Med. Chem.,* 14:819. The condensation product was treated with ammonia to yield 2-amino-6-chloro-9-(β-D-xylofuranosyl)purine. Further treatment with sodium hydroxyethylmercaptide gives the title compound.

EXAMPLE 129

2-Amino-6-mercapto-9-(β-D-threo-pentofuranosyl) purine 132.

2-Amino-6-chloro-9-(β-D-xylofuranosyl)purine as prepared by the Example 128, Method B, is treated with sodium hydrosulfide to give the title compound.

EXAMPLE 130

9-(2'-Deoxy-2'-methyl-β-D-threo-pentofuranosyl) guanine 133.

In a manner similar to Example 123, Method A, guanine is condensed with 1,3,5-tri-O-acetyl-2-deoxy-2-methyl-D-threo-pentofuranoside to yield the title compound.

EXAMPLE 131

2-Amino-xyloadenosine 134.

2-amino-8-mercaptoadenine is treated in the manner as per Example 128, Method B to yield the title compound.

EXAMPLE 132

Carbocyclic Xyloadenosine 135.

5-Amino-4, 6-dichloropyrimidine is treated with (±)-4α-amino-2α, 3β-dihydroxy-1α-cyclopentanemethanol to give a pyrimidine intermediate that is aminated and ring closed to yield the carbocyclic analog of xylofuranosyladenine as per the procedure of Vince, R. and Daluge, S. (1972), *J. Med. Chem.*, 15 15:171.

EXAMPLE 133

Carbocyclic Xyloinosine 136.

5-Amino-6-chloro-pyrimidyl-4-one when treated with (±)-4α-amino-2α, 3β-dihydroxy-1α-cyclopentanemethanol will give a pyrimidine intermediate that is then aminated and ring closed to yield the carbocyclic analog of xylofuranosylinosine as per the procedure of Example 132.

EXAMPLE 134

1-(β-D-2'-Deoxy-2'-fluoro-threo-pentofuranosyl) uracil 137.

In a manner similar to Example 125, uracil is condensed with 1,3,5,-tri-O-acetyl-2-deoxy-2-fluoro-D-threo-pentofuranoside to yield the title compound.

EXAMPLE 135

1-(β-D-2'-Deoxy-2'-fluoro-threo-pentofuranosyl) guanine 138.

In a manner similar to Example 125, guanine is condensed with 1,3,5,-tri-O-acetyl-2-deoxy-2-fluoro-D-threo-pentofuranoside to yield the title compound.

EXAMPLE 136

1- (β-D-2'-Deoxy-2'-fluoro-threo-pentofuranosyl) cytosine 139.

In a manner similar to Example 125, cytosine is condensed with 1,3,5,-tri-O-acetyl-2-deoxy-2-fluoro-D-threo-pentofuranoside to yield the title compound.

EXAMPLE 137

3'-O-[2-[[3-(benzoyloxy)-5-[3,4-dihydro-5-methyl-2, 4-dioxo-3-[(phenylmethoxy)methyl]-1(2H)-pyrimidinyl]tetrahydro-2-furanyl]thio]ethyl]-5'-O-(dimethoxytrityl)-adenosine 140.

Compound 126 will be treated with DMT-CL in pyridine and Et$_3$N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 138

3'-O-[2-[[3-(benzoyloxy)-5-[3,4-dihydro-5-methyl-2,4-dioxo-3-[(phenylmethoxy)methyl]-1(2H)-pyrimidinyl]tetrahydro-2-furanyl]thio]ethyl]-5'-O-(dimethoxytrityl)-3-deazaguanosine 141

Compound 127 will be treated with DMT-C1 in pyridine and Et$_3$N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, I,. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 139

3'-O-[2-[[3-(benzoyloxy)-5-[3,4-dihydro-5-methyl-2,4-dioxo-3-[(phenylmethoxy)methyl]-1 (2H) -pyrimidinyl] tetrahydro-2-furanyl]thio]ethyl]-5'-O-(dimethoxytrityl)-2'-deoxy-2'-fluoro-adenosine 142

Compound 128 will be treated with DMT-C1 in pyridine and Et$_3$N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 140

3'-O-[2-[[3-(benzoyloxy)-5-[3,4-dihydro-5-methyl-2,4-dioxo-3-[(phenylmethoxy)methyl]-1(2H)-pyrimidinyl]tetrahydro-2-furanyl]thio]ethyl]-5'-O-(dimethoxytrityl)-2'-deoxy-2'-methoxy-uridine 143

Compound 129 will be treated with DMT-C1 in pyridine and Et$_3$N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 141

3'-O-[2[[3-(benzoyloxy)-5-[3,4-dihydro-5-methyl-2,4-dioxo-3-[(phenylmethoxy)methyl]-1(2H)-pyrimidinyl]tetrahydro-2-furanyl]thio]ethyl]-5'-O-(dimethoxytrityl)-2'-O-allylcytosine 144

Compound 130 will be treated with DMT-C1 in pyridine and Et$_3$N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), J. Org. Chem., 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 142

3'-O-[2-[[3-(benzoyloxy)-5-[3,4-dihydro-5-methyl-2, 4-dioxo-3-[(phenylmethoxy)methyl]-1(2H)-pyrimidinyl]tetrahydro-2-furanyl]thio]ethyl]-5'-O-(dimethoxytrityl)-guanosine 145.

Compound 131 will be treated with DMT-Cl in pyridine and Et₂N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 143

3'-O-[2-[[3-(benzoyloxy)-5-[3,4-dihydro-5-methyl-2,4-dioxo-3-[(phenylmethoxy)methyl]-1(2H)-pyrimidinyl]tetrahydro-2-furanyl]thio]ethyl]-5'-O-(dimethoxytrityl)-6-thioguanosine 146

Compound 132 will be treated with DMT-Cl in pyridine and Et₃N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 144

3'-O-[2-[[3-(benzoyloxy)-5-[3,4-dihydro-5-methyl-2,4-dioxo-3-[(phenylmethoxy)methyl]-1(2H)-pyrimidinyl]tetrahydro-2-furanyl]thio]ethyl]-5'-O-(dimethoxytrityl)-2'-deoxy-2'-methyl-guanosine 147

Compound 133 will be treated with DMT-Cl in pyridine and Et₃N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125. will be treated with NaH to extract the hydroxyl proton and further treated with the above 3'-tosyl protected xylo nucleoside intermediate to yield the title compound.

EXAMPLE 145

3'-O-[2-[[(3-(Benzoyloxy)-5-[3,4-dihydro-5-methyl-2,4-dioxo-3-[(phenylmethoxy)methyl]-1(2H)-pyrimidinyl]tetrahydro-2-2-furanyl]thio]ethyl]-5'-O-(dimethoxytrityl)-2-aminoadenosine 148

Compound 134 will be treated with DMT-Cl in pyridine and Et₃N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 146

5'-O-(Dimethoxytrityl)-3'-O- [2-[[3-(benzoyloxy)-5-(3,4-dihydro-5-methyl-2,4-dioxo-3-[(phenylmethoxy)methyl]-1(2H)-pyrim-idinyl]tetrahydro-2-furanyl]thio]ethyl]-carbocyclic-adenosine 149

Compound 135 will be treated with DMT-Cl in pyridine and Et₃N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 147

5-O-(Dimethoxytrityl)-3'-O-[2-[[(3-(benzoyloxy)-5-[3,4-dihydro-5-methyl-2,4-dioxo-3-[(phenylmethoxy)methyl]-1(2H)-pyrim-idinyl]tetrahydro-2-furanyl]thio]ethyl]-carbocyclic-inosine 150

Compound 136 will be treated with DMT-Cl in pyridine and Et₃N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 148

5'-O-(Dimethoxytrityl)-3'-O-[2-[[3-(benzoyloxy)-5-[3,4-dihydro-5-methyl-2,4-dioxo-3-[(phenylmethoxy)methyl]-1(2H)-pyrim-idinyl]tetrahydro-2-furanyl]thio]ethyl]-2'-deoxy-2'-fluoro-uracil 151

Compound 137 will be treated with DMT-Cl in pyridine and Et₃N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 149

5'-O-(Dimethoxytrityl)-3'-O-[2-[[3-(benzoyloxy)-5-[3,4-dihydro-5-methyl-2,4-dioxo-3-[(phenylmethoxy)methyl]-1(2H)-pyrim-idinyl]tetrahydro-2-furanyl]thio]ethyl]-2'-deoxy-2'-fluoro-guanosine 152

Compound 138 will be treated with DMT-Cl in pyridine and Et₃N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 150

5'-O-(Dimethoxytrityl)-3'-O-[2-[[3-(benzoyloxy)-5-[3,4-dihydro-5-methyl-2,4-dioxo-3-[(phenylmethoxy)methyl]-1 (2H)-pyrim-idinyl]tetrahydro-2-furanyl]thio]ethyl]-2'-deoxy-2'-fluoro-cytosine 153

Compound 139 will be treated with DMT-C1 in pyridine and Et$_3$N as per the procedure of Example 14. The 5'-DMT protected intermediate will be treated with p-toluenesulfonylchloride in pyridine as per the procedure of Reist, E. J., Bartuska, V. J., Calkins, D. F., and Goodman, L. (1965), *J. Org. Chem.*, 30:3401 to yield the 3'-tosyl protected xylo nucleoside intermediate. Compound 125 will be treated with NaH to extract the hydroxyl proton and further treated with the above 3'-tosyl protected xylo nucleoside intermediate to yield the title compound.

EXAMPLE 151

3'-Deoxy-3'-(hydroxymethylchlorodiphenylsilyl)-5'-dimethoxytrityl-O-thymidine 154.

Compound 10 is treated with dichlorodiphenylsilane in the manner of Ogilvie, K. K. and Cormier, J. F., *Tetrahedror, Letts.* 1985, 26, 4159, to give the title compound, 154.

EXAMPLE 152

1-[5-hydroxy-4-benzoyloxy-tetrahydro-2-furanyl]-5-methyl-3-[(phenylmethoxy)methyl]-2,4(1H, 3H)-pyrimidindione 155.

Compound 8 is treated with DBU as per the procedure of Baptistella, L. H., dos Santos, J. F., Ballabio, K. C. and Marsaioli, A. J., *Synthesis Comm.*, 1989, 436, to selectively remove the acetyl group in the presence of the benzoyl group to give the title compound, 155.

EXAMPLE 153

5'-O-(Dimethoxytrityl)-3'-deoxy-3'-hydroxymethyl-[O-[[3-(benzoyloxy)-5-[3,4-dihydro-5-methyl-2,4-dioxo-3-[(phenylmethoxy)methyl]-1(2H)-pyrimidinyl]tetrahydro-2-furanyl]oxy]diphenylsilyl]-3-[(phenylmethoxy)methyl]-thymidine 156

Compound 154 is treated with compound 155 as per the procedure of Ogilvie, K. K. and Cormier, J. F., *Tetrahedron Letts.* 1985, 26, 4159, to give the title compound, 156.

EXAMPLE 154

3'-Deoxy-3'-(methylthiomethylthiomethyl)-5'-O-(tert-butyldiphenylsilyl)thymidine 157.

Compound 119 is treated as per the procedure of Step 1 of Example 1 of PCT published application WO 91/06629 (or via the procedure of Mattecuui, M., *Tet. Letts.* 1990 31, 2385) to give the title compound, 157.

EXAMPLE 155

3'-Deoxy-5'-O-(tert-butyldiphenylsilyl)-3'-methylthio-[S-[[5-[3,4-dihydro-5-methyl-2,4-dioxo-1(2H)-pyrimidinyl]tetrahydro-3-hydroxy-2-furanyl]oxy]methyl]-thymidine 158.

Compounds 157 and 98 will be reacted as per the procedure of Steps 2 and 3 of Example 1 of PCT published application WO 91/06629 followed deblocking of the 3'-(1, 1-dimethylethyl)diphenylsilyl) blocking group utilizing the procedure of Example 13 to give the title compound, 158.

EXAMPLE 156

3'-Deoxy-5'-O-(tert-butyldiphenylsilyl)-3'-methylsulfoxide-[S-[]5-[3,4-dihydro-5-methyl-2,4-dioxo-1(2H)-pyrimidinyl]tetrahydro-3-hydroxy-2-furanyl]oxy]methyl]-thymidine 159.

Compound 158 will be oxidized with one equivalent of m-chloroperbenzoic acid as per the procedure of Example 8-D published PCT patent application PCT/US91/05720 to give the title compound, 159.

EXAMPLE 157

3'-Deoxy-5'-O-(tert-butyldiphenylsilyl)-3'-methylsulfone-[S-[(5-[3,4-dihydro-5-methyl-2,4-dioxo-1(2H)-pyrimidinyl]-tetrahydro-3-hydroxy-2-furanylloxy]methyl]-thymidine 160.

Compound 158 will be oxidized with an excess of m-chloroperbenzoic acid as per the procedure of Example 8-E of published PCT patent application PCT/US91/05720 to give the title compound, 160.

EXAMPLE 158

Carbocyclic 4'-desmethyl-ribo- or -2'- deoxy-nucleosides.

A. CPG Bound Carbocyclic Desmethyl-ribo- or-2'-deoxynucleoside.

3-(Aden-9-yl)-5-hydroxy-1,2-cyclopentene, obtained from the coupling of cyclopentene epoxide and adenine according to the method of Trost, et. al., *J. Am. Chem. Soc.* 1988, 110, 621–622, is successively silylated, benzoylated, and tritylated according to standard procedures to provide 3-(N6-benzoyladenyl)-5-triphenylmethoxyl-1,2-cyclopentene. Cis-hydroxylation and selective t-butyldimethylsilylation provides the 2'-O-t-butyldimethylsilyl derivative. The free 3'-hydroxy of this carbocyclic nucleoside is attached to control-glass pore silica gel (CPG) according to the standard procedure of T. Atkinson and M. Smith (Oligonucleotide Synthesis. A Practical Approach. M. J. Gait, Ed., IRL Press, Washington, D.C., 1985, p 49). The CPG-bound carbocyclic, adenine is treated with acid to remove the 4'-O-trityl protection and the resulting hydroxy group is subsequently reacted with t-butoxyethyl bromide and base to afford the 4'-O-t-butoxyethyl derivative. The final product, 4'-desmethyl-4'-O-t-butoxyethyl-2'-t-butyldimethyl-silyl-3'-CPG-N6-benzoyl adenine, is placed in a column and attached to a ABI-380B automated DNA Synthesizer or a 7500 Milligen/Biosearch DNA Synthesizer. The CPG-bound 4'-desmethyl ribonucleosides can be converted to their 2'-deoxy forms by the successive treatment of the polymer with tetrabutyl ammonium fluoride, thiocarbonylimidazole, and tributyl tin hydride. These procedures are appropriate for the preparation of CPG bound carbocyclic 4'-desmethyl derivatives of the other natural occurring bases or nucleic acids base analogs.

B. Carbocyclic Desmethyl-ribo-monomers—First Procedure 3-(Aden-9-yl)-5-hydroxy-1,2-cyclopentene, obtained from the coupling of cyclopentene epoxide and adenine according to Trost, et al. is successively silylated, benzoylated, and tritylated according to standard procedures to provide 3-(N$^6$-benzoyladenyl) -5-triphenylmethoxy-1,2-cyclopentene. Cis-hydroxylation and selective t-butyldimethylsilylation provides the 2'-O-t-butyldimethylsilyl derivative. This material is treated with trichloroacetonitrile and sodium hydride in dry acetonitrile to afford the a trichloroacetimidate which is subsequently SN2 displaced by water. Preparation and reactivity of trichloroacetimidates has been described. The resulting β3'-hydroxyl group is activated for SN-2 reaction by the action of trichloroacetonitrile/sodium hydride. The β-3'-hydroxy group may also be activated for SN2 reactions by the treatment with trifluoromethane-sulfonic acid anhydride and pyridine. This procedure provides the triflate group in the -3'-position of the 4'-desmethyl-4'-O-t-butoxyethyl-2'-t-butyldimethylsilyl-N$^6$-benzoyl adenine. This procedure is of a general nature and can be applied to the synthesis of any carbocyclic 4'-desmethyl- ribonucleoside.

C. Carbocyclic Desmethyl-ribo-monomers—Second Procedure

The carbocyclic nucleoside antibiotic (-)-neplanocin A, obtained from fermentation or total synthesis; Johnson, et. al., *Tet. Lett.* 1987, 28, 4131; base analogs of (-)-neplanocin, Biggadike, A., et al., *J. Chem. Soc.,* Chem. Comm. 1990, 458 as its N$^6$-benzoyl derivative is reduced with a borane reagent and then protected as its isopropylidine. The unprotected 5'-hydroxyl is oxidized with oxygen and platinum oxide, and subsequent, reductive decarboxylation with lead tetraacetate provides 4'-desmethyl carbocyclic adenosine. This oxidation/reduction closely follows a known procedures. The 4'-desmethyl carbocyclic adenosine 2,3-isopropylidine is successively treated with t-butoxyethyl bromide and pyridine, mild acid, and t-butyldimethysilyl chloride in pyridine to afford the 4'-desmethyl carbocyclic derivative with an α-3'-hydroxyl group unprotected. This intermediate was described in paragraph A. Conversion into an activated β-3'-leaving group is described in paragraph B.

D. Carbocyclic Desmethy-2-deoxyribo-monomers.

4-p-Tosylate-1,2-cyclopentene is treated with appropriately protected bases to afford cyclopentenylated bases of the natural nucleoside bases or analogs of the nucleic acids bases. Hindered face (β-face) hydroxylation provides 3,4-dihydroxy cyclopentyl-protected bases which are treated with t-butoxyethyl bromide and the isomers are separated by chromatography. The appropriate isomer is treated with trichloroacetonitrile and sodium hydride in acetonitrile to provide 4'-desmethyl-4'-O-t-butoxyethyl-3'-O-trichloroacetimidyl-2'-deoxy carbocyclic nucleosides.

EXAMPLE 159

Synthesis of 4'-desmethyl-ribo- or -2'-deoxy-nucleosides.

A. CPG Bound Desmethyl-ribo- or -2'- deoxyribo-nucleosides—First Procedure.

Commercially available CPG-bound ribo or 2'-deoxyribo-nucleosides are treated with oxygen saturated acetonitrile and platinum oxide to provide the 4'-desmethyl-4'-carboxylate derivative. The CPG column is treated with lead tetraacetate to reductively decarboxylate the bound nucleoside. The resultant 4'-hydroxyl group is alkylated with t-butoxyethyl bromide in pyridine to provide CPG-bound 4'-desmethyl-4'-O-t-butoxyethyl-2'-deoxy (or2'-t-butyldimethylsilyl) nucleosides.

B. CPG Bound Desmethyl-ribo- or -2'-deoxyribo-nucleosides—Second Procedure.

Commercially available ribo or 2'-deoxy- ribonucleosides protected in the heterocycle and 2',3'-O-positions or the 3'-O-position by standard procedures such as the 2',3'-O-isopropylidinyl or 3'-O-benzoyl were successively oxidized and reductively decarboxylated with oxygen/platinum oxide and LTA to afford a 4'-hydroxyl group. These protected nucleosides are converted to their 4'-desmethyl-4'-O-t-butoxyethyl derivatives by treatment with t-butoxyethyl bromide and pyridine. Removal of the 3'-O-benzoyl or 2',3'-O-isopropylidine groups and subsequent attachment to control glass pore silica gel according to standard procedures provides CPG-bound desmethyl-ribo- or -2'-deoxyribo nucleosides suitable for solid phase, automated nucleic acids synthesis.

C. 4'-Desmethyl-ribo- and -2'-deoxyribo monomers.

Commercially available 2'-deoxyfuranosyl nucleosides and xylofuranosylnuclosides with appropriate base protection are selectively tritylated in the 5'-position then mono or di-benzoylated in the sugar ring. The nucleosides are now treated with acid to remove the trityl protection. The successive action of oxygen/PtO$_2$ and LTA provides the 4'-desmethyl nucleosides which are subsequently alkylated with, t-butoxyethyl bromide. Basic deprotection of the nucleosides affords the 4'-desmethyl-2'-deoxyxylofuranosylnucleosides and the 4'-desmethylxylo nucleosides. The 4'-desmethyl-2'-deoxyxylo nucleoside is treated with trichloroacetonitrile and sodium hydride to activate the 3'-up hydroxyl group to SN2 reactions. The 4'-desmethylxylo nucleoside is selectively t-butyldimethylsilylated at the 2'-position and then is treated with trichloroacetonitrile and sodium hydride to activate the 3'-up hydroxyl group to SN2 reactions. The triflate leaving group in the 3'-up position of there nucleosides can also be readily prepared.

EXAMPLE 160

Synthesis of carbocyclic 4'-desmethyl-ribo- or -2'-deoxy-oligonucleosides and 4'-desmethyl-ribo- or -2'-deoxy-oligonucleosides linked via an ethylene glycol.

The appropriately CPG-bound 4'-desmethylnucleoside (ribo or 2'-deoxyribo or carbocyclic ribo or 2'-deoxyribo) that will become the 3'-terminal base is placed in an Applied Biosystems, Inc. (ABI) column and attached to an ABI 380B automated DNA Synthesizer. The automated (computer controlled) steps of a cycle that is required to couple a desmethyl nucleoside unit to the growing chain is as follows.

| STEP | REAGENT OR SOLVENT MIXTURE | TIME (min/sec) |
|---|---|---|
| 1. | Dichoroethane | 2:30 |
| 2. | 3% DCA in dichloroethane | 3:00 |
| 3. | Dichloroethane | 1:30 |
| 4. | Tetrahydrofuran | 1:30 |
| 5. | 3.0 Molar methylmagnesium chloride in THF | 1:00 |
| 6. | Tetrahydrofuran | 1:00 |
| 7. | 4'-Desmethyl-4'-O-t-butoxyethyl 3'-up trichloroacetimidate nucleoside 10 equivalents to CPG-bound nucleoside | 2:00 |
| 8. | Recycle to step 7 | 2:00 |
| 9. | t-Butyldimethylsilyl chloride/ pyridine | 2:00 |
| 10. | Recycle - go to step one | |

At the completion of the synthesis, the deprotection/purification process is as follows:

| STEP | REAGENT OR SOLVENT MIXTURE | TIME (min/sec) |
|---|---|---|
| 1. | 3% DCA in dichloroethane | 3:00 |
| 2. | Acetonitrile wash | 3:00 |
| 3. | Tetrabutyl ammonium fluoride 1.0 molar solution in THF | 5:00 |
| 4. | Acetonitrile | 2:00 |
| 5. | 15% Ammonium hydroxide/ethanol (1:1), 50° C. | 5:00 |
| 6. | Filter, wash CPG resin with 15% NH4OH/EtOH | |
| 7. | 30% NH4OH, 50° C. | 24 hr |
| 8. | Evaporate solution to dryness | |
| 9. | HPLC purification | |

EXAMPLE 162

Preparation of polyamine and polyethylene glycol derivatives of carbocyclic 4'-desmethyl-ribo- or -2'-deoxy- oligonucleosides and 4'-desmethyl-ribo- or -2'-deoxy- oligonucleosides linked via an ethylene glycol At the completion of the synthesis, polyethylene glycols (PEGS) with terminal alkyl bromides or phthaloyl and trifluoroacetyl protected polyalkyl amines with terminal alkyl bromides are reacted with the CPG-bound oligonucleoside in the presence of base. Deprotection, workup, and purification provides 4'-polyethylene glycol or 4'-polyamines nucleosides and carbocyclic nucleosides linked via ethylene glycol moieties.

EXAMPLE 163

Preparation of Oligonucleotide Containing Dimeric Unit Having 4'-Desmethyl Structure.

Utilizing normal protocol for solid state DNA synthesis, (see *Oligonucleotide synthesis, a practice approach*, Ed. M. J. Gait, IRL Press 1984, Oxford University Press, New York), the dimer 14 was incorporated with the sequence:

5CG T*T T*T CG 3' wherein T*T represents the dimer 14. The DMT protected phosphoramidite activated dimer 16 was use in the normal manner as a standard amidite during the synthesis. Coupling efficiencies were greater than 96% for each step of the synthesis with the overall coupling efficiency greater than 91% for the oligomer. The resulting oligomer was characterized by both gel chromatography and by HPLC using standard protocols.

EXAMPLE 164

1-[5-Azido-4-(tert-butyldiphenylsilyl)-tetrahydrofuran-2-yl]-$N^3$-benzoylmethylthymine 161.

Compound 97 is treated with $(CH_3)_3SiN_3$ in the presence of a Lewis acid utilizing the procedure of Gyorgydeak, Z., Ling, I. and Bognar, R., *Liebigs Ann. Chem.* 1983 279 to give the title compound.

EXAMPLE 165

1-[5-Amino-4-(tert-butyldiphenylsilyl)-tetrahydrofuran-2-yl]-$N^3$-benzoylmethylthymine 162.

Compound 161 will be reduced as per Example 31 to give the title compound 162.

EXAMPLE 166

3'-Deoxy-3'-[3-[[3-(tert-butyldiphenylsilyl)-5-[3,4-dihydro-5-methyl-2,4-dioxo-3-[(phenylmethoxy)methyl]-1 (2H)-pyrimidinyl]-tetrahydro-2-furanyl]amino]propyl]-5-O-[(1,1-dimethylethyl) diphenylsilyl]-3-[(phenylmethoxy) methyl]thymidine51-a Compound 162 is reacted with compound 90 under nucleophilic displacement reaction conditions (see *Advanced Organic Chemistry, Reactions, Mechanisms, and Structure, J.* March Ed., 1992, pg. 412, John Wiley & Sons, N.Y.) to yield the title dimeric compound 51.

EXAMPLE 167

3-Deoxy-5'-O-(tert-butyldiphenylsilyl)]-3'-[2- [[3-(tert-butyl-diphenylsilyl)-5-[3,4-dihydro-5-methyl-2,4-dioxo-1 (2H)-pyrimidinyl]tetrahydro-2-furanyl]amino][(β-cyanoethoxy) (methylthiophosphiryl)]-thymidine 163

Compound 120 will be reacted with compound 162 as per the procedure of Cosstick, R. and Vyle, J. S. Nucleic Acids Research 1990 18, 829 to give the title compound 163.

EXAMPLE 168

3-Deoxy-5'-(tert-butyldiphenylsilyl)-3'-[2[[3-(tert-butyldi phenylsilyl)-5-[3,4-dihydro-5-methyl-2,4-dioxo-1(2H)-pyrim-idinyl]tetrahydro-2-furanyl]amino][(β-cyanoethoxy) (methylthiolphosphate)]]-thymidine 164

The $P^{III}$ compound 163 from Example 167 will be oxidized to the $p^V$ phosphate using tetrabutylammonium periodate as the oxidization agent to give the title compound, 164.

EXAMPLE 169

3'-Deoxy-5'-(tert-butyldiphenylsilyl)-3,'-[[3-(tert-butyldiphenylsilyl)-5-[3,4-dihydro-5-methyl-2,4'dioxo-1 (2H)-pyrimidinyl]tetrahydro-2-furanyl]amino][(B-cyanoethoxy) (methylthiothiophosphate)]]-thymidine 165

The $p^{III}$ compound 163 from Example 167 will be oxidized with sulfur to the $p^V$ thiophosphate as per the procedure of Cosstick, R. and Vyle, J. S. *Nucleic Acids Research* 1990 18, 829 to give the title compound 165.

EXAMPLE 170

1-[5-(2-Hydroxyethoxy)-4-benzoyloxy-tetrahydrofuran-2-yl]-$N^3$-benzoylmethylthymine 166.

A solution of compound 8 (912 mg, 1.85 mmol) and bistrimethylsilyl glycol (762 mg, 2.70 nmol) in $CH_3CN$ was cooled to −23 ° C. and trimethylsilyl triflate (600 mg, 0.9 mmol) was added. The reaction was stirred for 3 hrs and poured in to a mixture of ethylether/water containing $Et_3N$ (5 mL) . The organic phase was separated, washed with $H_2O$, washed with brine and dried over $MgSO_4$. The solvent was evaporated under vacuum and the residue purified by silica gel chromatography to give 558 mg of the title compound as a syrup. $R_f$ (hexanes/AcOEt 1:1) 0.22; $^1H$ NMR $(CDCl_3)$:δ1.97 (s, 3H, 5-$CH_3$), 2.25–2.43 (m, 3'-$H_β$), 2.56–2.71 (m, 3'-$H_δ$), 3.63–3.95 (m, 4H, $OCH_2CH_2O$), 4.69 (s, 2H, O-$CH_2$-Ph), 5.25 (s, 1H, 5'-H), 5.47 (d, J=5.4 Hz, 4'-H), 5.51 (s, 2H, N-$CH_2$-O), 6.80 (dd, 1H, J=8.0, 6.7 Hz, 2'-H), 7.18–7.65 (m, 9H, aromatic-H and 6-H), 8.04–8.07 (m, 2H, aromatic-H).

EXAMPLE 171

1-[5-(2-Allyloxy)-4-benzoyloxy-tetrahydrofuran-2-yl]-$N^3$-benzoylmethylthymine 167.

A solution of compound 8 (4.94 g, 10.0 mmol), allyl alcohol (1.36 mL, 20.0 mmol) and $Et_3N$ (1.01 g, 1.4 ml, 10 mmol) in 4:1 CH$_2$Cl$_2$:CH$_3$CN was cooled to −23 ° C. and reacted with trimethylsilyl triflate (3.33 g, 15.0 mmol) as per the procedure of Example 169 to give 3.88 g of crude product. The crude product was recrystallized from AcOEt/hexanes to give the title compound as a white solid. Recrystallization from AcOEt/diethylether gave white needle-like crystals. mp 112–113° C.; R$_f$ (hexanes/AcOEt 1:1) 0.60; $^1$H NMR (CDCl$_3$):δ1.93 (s, 3H, 5-CH$_3$), 2.33 (ddd, 1H, J=14.5, 6.8, 4.7 Hz, 3'-H$_\beta$), 2.64 (dd, 1H, J=14.5, 8.1 Hz, 3'-H$_\alpha$), 4.17 (dd, 1H, J=12.6, 4.1, 1.0 Hz, O—CHH—CH=CH$_2$), 4.29 (ddd, 1H, J=12.6, 5.8, 1.0 Hz, O—CHH—CH=CH$_2$), 4.72 (s, 2H, O—CH$_2$—Ph), 5.24 (s, 1H, 5'-H), 5.30 (ddd, 1H, J=10.2, 1.3, 1.0 Hz, O—CH$_2$—CH=CHH$_{trans}$), 5.30 (ddd, 1H, J=17.3, 1.5, 1.0 Hz, O—CH$_2$—CH=CHH$_{cis}$), 5.47 (d, J=4.7 Hz, 4'-H), 5.51 (s, 2H, N—CH$_2$—O), 5.97 (dddd, 1H, J=17.3, 10.2, 5.8, 4.1 Hz, O—CH$_2$—CH=CH$_2$) , 6.82 (dd, 1H, J=8.1, 6.8 Hz, 2'-H) , 7.18–7.65 (m, 9H, aromatic-H and 6-H), .8.03–8.06 (m, 2H, aromatic-H). Anal. Calcd for C$_{28}$H$_{28}$N$_2$O$_7$ C, 68.29; H, 5.69; N, 5.69. Found C, 68.36; H, 5.63; N, 5.60.

EXAMPLE 172

1-[5-(2,3-Dihydroxypropoxy)-4-benzoyloxy-tetrahydrofuran-2-yl]-N$^3$-benzoylmethylthymine 168.

A solution of compound 167 (4.5 g, 9.15 mmol) and NMO (1.69 g, 13.66 mmol) was reacted as per the procedure of Example 18 to yield 4.46 g (92%) of the title compound as a white solid. R$_f$(CH$_2$Cl$_2$/MeOH 10:1): 0.40; $^1$H NMR (CDCl$_3$+D$_2$O): δ1.97 (s, 3H, 5-CH$_3$), 2.34 (ddd, 1H, J=14.8, 7.9, 4.8 Hz, 3'-H$_\beta$), 2.64 (dd, 1H, J=14.8, 6.6 Hz, 3'-H$_\alpha$), 3.56–4.02 (m, 5H, OCH$_2$CHOHCH$_2$O) , 4.71 (s, 2H, O—CH$_2$—Ph), 5.23 (s, 1H, 5'-H), 5.46 (d, 1H, J=4.8 Hz, 4'-H), 5.51 (s, 2H, N—CH$_2$—O), 6.78 (dd, 1H, J=7.9, 6.6 Hz, 2'-H), 7.25–7.66 (m, 9H, aromatic-H and 6-H), 8.01–8.06 (m, 2H, aromatic-H); $^{13}$C NMR (CDCl$_3$): δ13.18 (-, 5.-C), 34.92 (+, 3—-C), 63.60 (+, O—C—COH—C—OH), 70.06 (+, O—C—Ph), 70.70 (-, O—C—COH—C—OH), 70.76 (+, O—C—COH—C—OH), 72.33 (N—C—O), 77.63 (-. 4'-C), 86.65 (-, 2'-C), 106.55 (-, 5'-C), 111.53 (+, 5-C), 127.69 (-, aromatic-C), 128.35 (-, 6-C), 5 128.66 (-, aromatic-C), 128.90 (+, aromatic-C), 133.87, 134.42 (-, aromatic-C), 137.91 (+, aromatic-C), 151.38 (+, 2-C), 163.40 (+, 4-C), 165.85 (+, benzoyl C=O).

EXAMPLE 173

1-[5-(C-formylmethoxy)-4-benzoyloxy-tetrahydrofuran-2-yl]-N$^3$-benzoylmethylthymine 169.

A solution of compound 168 (4.5 g, 2.85 mmol) and NaIO$_4$ (0.78 g, 3.66 mmol) in 1:1 THF/H$_2$O (120 mL) was stirred at RT for 2 hrs. The solvent was evaporated under vacuum and the residue was purified by silica gel chromatography (CHCl$_3$/MeOH, 20:1→10:1) to give 1.31 g of the title compound as a white foam.

EXAMPLE 174

1-[5-(2-Bromoethoxy)-4-benzoyloxy-tetrahydrofuran-2-yl]-N$^3$-benzoylmethylthymine 170.

A solution of compound 8 (4.0 g, 8.1 mmol), 2-bromoethanol (3.0 gl 24.3 mmol) and Et$_3$N in 5:1 CH$_2$Cl$_2$/CH$_3$CN (30 mL) was cooled to −23° C. and trimethylsilyl triflate (3.6 g, 16.2 mmol) was added. The reaction was stirred under argon for 1 hrs followed by standing at −15° C. for 15 hrs. The reaction mixture was worked up as per the procedure of Example 169 to give 4.1 g of the title compound as a white foam R$_f$ (hexanes/AcOEt 3:1:) 0.32; $^1$H NMR (CDCl): δ1.99 (s, 3H, 5-CH3), 2.35 (ddd, 1H, J=14.8, 8.4, 4.9 Hz, 3'-H$_\beta$), 2.63 (dd, 1H, J=14.8, 6.4 Hz, 3'-H$_\alpha$) , 3.57 (t, 2H, J=5.5 Hz, BrCH$_2$CH$_2$O), 3.99 (dt, 1H, J=16.4, 5.5 Hz, BrCH$_2$CHHO), 4.10 (dt, 1H, J=16.4, 5.5 Hz, BrCH$_2$CHHO), 4.72 (s, 2H, O—CH$_2$—Ph), 5.25 (s, 1H, 5'-H), 5.49 (d, 1H, J=4.9 Hz, 4'-H), 5.52 (s, 2H, N—CH$_2$—O), 6.82 (dd, 1H, J=8.4, 6.4 Hz, 2'-H) , 7.27–7.66 (m, 9H, aromatic-H and 6-H), 8.02–8.06 (m, 2H, aromatic-H); $^{13}$C NMR (CDCl$_3$): δ13.42 (-, 5-C), 30.26 (+, Br—C—C—O) , 34.73 (+,3'C), 68.87 (+, O—C—Ph), 70.76 (+Br—C—C—O), 72.28 (N—C—O), 77.48 (-. 4'-C), 86.46 (-, 2'-C), 106.40 (-, 5'-C), 111.63 (+, 5-C), 127.68 (-, aromatic-C), 128.34 (-, 6-C), 128.66 (-, aromatic-C), 128.96, (+, aromatic-C), 129.86, 133.83, 134.94 (-, aromatic-C), 138.05 (+, aromatic-C), 151.42 (+, 2-C), 163.24 (+, 4-C), 165.65 (+, benzoyl C=O).

EXAMPLE 175

5'-O-tert-Butyldiphenylsilyl-2-O,3'-anhydrothymidine 171.

The title compound was prepared in a manner as per the published procedure of (Glinski, R. P.; Khan, M. S.; Kalamas, R. L.; Sporn, M. B. J. Org. Chem. 1973, 38, 4299.) from 2 in 3 steps in 47% yield to give a white solid. R$_f$ (CHCl$_3$/MeOH 9:1) 0.04; $^1$H NMR (DMSO-d$_6$) : δ0.97 (s, 9H, (CH$_3$)$_3$-C) , 1.76 (s, 3H, 5-CH$_3$), 2.53 (m, 2H, 2'-H), 3.61 (dd, 1H, J =10.4, 7.4 Hz, 5'- CHH), 3.84 (dd, 1H, J=10.4, 5.5 Hz, 5'-CHH), 4.44 (ddd, 1H, J=7.4, 5.5, 2.4 Hz, 4'-H), 5.32 (m, 1H, 3'-H), 5.87 (d, 1H, J=3.5 Hz, 1-H), 7.33–7.64 (m, 11H, aromatic-H and 6-H).

EXAMPLE 176

3'-Deoxy-3'-azido-5'-O-(tert-butyldiphenylsilyl) thymidinel 172.

A solution of 6.4 g (13.9 mmol) of 171, 0.9 g (20.0 mmol) of LiN$_3$ and 0.5 g (4.1 mmol) of benzoic acid in 90 ml of DMF was heated to reflux for 1 hour. The solvent was removed at reduced pressure and the residue was purified by SiO$_2$ column chromatography (CH$_2$Cl$_2$/AcOEt 3:1) to give 6.2 g (88.6%) of 172 as a yellow syrup. R$_f$ (CH$_2$Cl$_2$/AcOEt 3:1) 0.29; $^1$H NMR (CDCl$_3$): δ1.11 (s, 9H, (CH$_3$)$_3$-C), 1.64 (s, 3H, 5-CH$_3$) , 2.32 (ddd, 1H, J=13.8, 7.6, 7.3 Hz, 2'-H,) , 2.43 (ddd, 1H, J=13.8, 6.3, 4.0 Hz, 2'H$_\beta$), 3.82 (dd, 1H, J=11.4, 2.4 Hz, 5'-CHH), 3.95 (ddd, 1H, J=7.6, 2.7, 2.4 Hz, 4'-H), 4.00 (dd, 1H, J=11.4, 2.7 Hz, 5-CHH), 4.33 (ddd, 1H, J=7.6, 4.3, 4.0 Hz, 3'-H), 6.26 (dd, 1H, J=7.3, 6.3 Hz, 1'-H), 7.27–7.50 (m, 7H, aromatic-H and 6-H), 7.65–7.71 (m, 4H, aromatic-H), 8.98 (br s, 1H, NH) ; $^{13}$C NMR (CDCl$_3$): δ12.13 (-, 5-CH$_3$), 19.41 (+, Me$_3$-C) 26.60 (-, 3'-C), 27.05 (-, Me$_3$-C), 37.89 (+, 2'-C) , 60.50 (+, 5'-C), 63.56 (-, 4'-C), 84.34 (-, 1'-C), 111.42 (+, 5-C), 128.41 (-, aromatic-C), 130.20 (-, 6-C), 134.83 (+, aromatic-C), 135.33, 135.55 (-, aromatic-C), 150.19 (+, 2-C), 163.69 (+, 4-C).

EXAMPLE 177

N3-Benzyloxymethyl-3'-deoxy-3'-azido-5'-O- (tert-butyldiphenyl-silyl)thymidine 173.

A solution of 6.2 g (12.3 mmol) of 172 and 4.3 ml (3.2 g, 24.6 mmol) of Hunig's base in 80 ml of CH$_2$Cl$_2$ was added 2.2 ml (2.5 g, 16.0 mmol) of benzyloxymethyl chloride. The mixture was stirred at 23° C. for 16 hours. The solvent was removed at reduced pressure and the residue was purified by SiO$_2$ column chromatography (hexanes/AcOEt 10:1 then 3:1) to give 5.5 g (71.3%) of 173 as a yellow syrup. R$_f$ (hexanes/AcOEt 4:1) 0.28; $^1$H NMR (CDCl$_3$): δ1.11 (s, 9H, (CH$_3$)$_3$-C), 1.64 (s, 3H, 5-CH3), 2.25 (ddd, 1H, J=13.7, 7.8, 7.3 Hz, 2'-H$_\beta$), 2.45 (ddd, 1H, J=13.7, 6.1, 4.1 Hz, 2'-H$_\alpha$), 3.81 (dd, 1H, J=11.7, 2.6 Hz, 5'-CHH), 3.93 (ddd, 1H, J=5.0, 2.7, 2.6 Hz, 4'-H), 4.00 (dd, 1H, J=11.7, 2.7 Hz, 5'-CHH), 4.30 (ddd, 1H, J=7.8, 5.0, 4.1 Hz, 3'-H), 4.70 (s, 2H, OCH$_2$Ph), 5.48 (s, 2H, NCH$_2$O), 6.25 (dd, 1H, J=7.3, 6.1 Hz, 1'-H), 7.22–7.48 (m, 13H, aromatic-H and 6-H), 7.63–7.68 (m, 4H, aromatic-H); $^{13}$C NMR (CDCl$_3$): δ12.89 (-, 5-CH$_3$), 19.44 (+, Me$_3$-C), 27.08 (-, Me$_3$-C), 37.97 (+, 2'-C), 60.39 (-, 3'-C), 63.53 (+, 5'-C), 70.65 (+, O—C—Ph), 72.32 (+, N—C—O), 84.34 (-, 4'-C), 85.07 (-, 1'-C), 110.65 (+,5-C), 127.68, 128.09, 128.34 (-, aromatic-C), 130.35 (-, 6-C), 132.28, 132.75 (+, aromatic-C), 133.71, 135.36, 135.59 (-, aromatic-C), 138.11 (+, aromatic-C), 150.90 (+, 2-C), 163.39 (+, 4-C).

EXAMPLE 178

N$^3$-Benzyloxymethyl-3'-deoxy-3'-amino-5'-O-(tert-butyldiphenyl-silyl)thymidine 174.

A solution of 4.5 g (7.2 mmol) of 173, 5.0 ml (5.4 g 18.6 mmol) of Bu,SnH and 100 mg (0.6 mmol) of AIBN in 100 ml of THF was heated to reflux for 2 hours. The solvent was removed at reduced pressure and the residue was purified by SiC$_2$ column chromatography (hexanes/AcOEt 1:1) to give 4.0 g (92.7%) of 174 as a yellow syrup. R$_f$ (hexanes/AcOEt 1:1) 0.34; $^1$H NMR (CDCl$_3$): δ1.10 (s, 9H, (CH$_3$)$_3$-C), 1.37 (br s, NH$_2$), 1.67 (s, 3H, 5-CH$_3$), 2.12 (m, 2H, 2'-H), 3.67 (m, 1H, 3'-H), 3.72 (ddd, 1H, J=5.9, 2.8, 2.6 Hz, 4'-H), 3.85 (dd, 1H, J=11.4, 2.8 Hz, 5'-CHH), 4.02 (dd, 1H, J=11.4, 2.6 Hz, 5'-CHH), 4.71 (s, 2H, OCH$_2$Ph), 5.50 (s, 2H, NCH$_2$O), 6.27 (t, 1H, J=4.7 Hz, 1'-H), 7.27–7.50 (m, 13H, aromatic-H and 6-H), 7.65–7.69 (m, 4H, aromatic-H); $^{13}$C NMR (CDCl$_3$): δ12.93 (-, 5-CH$_3$), 19.42 (+, Me$_3$-C), 27.05 (-, Me$_3$-C), 41.58 (+, 2'-C), 51.32 (-, 3'-C), 63.54 (+, 5'-C), 70.58 (+, O—C—Ph), 72.26 (+, N—C—O), 85.01 (-, 4'-C), 87.32 (-, 1'-C), 110.21 (+, 5-C), 127.72, 128.32, 129.62 (-, aromatic-C), 130.09 (-, 6-C), 132.63, 133.04 (+, aromatic-C), 134.86, 135.42, 135.61 (-, aromatic-C), 138.06 (+, aromatic-C), 150.99 (+, 2-C), 163.54 (+, 4-C).

EXAMPLE 179

N3-Benzyloxymethyl-3'-deoxy-3'-N-ethoxycarbomethyl-5'-O-(tert-butyldiphenylsilyl) thymidine 175.

A suspension of 1.8 g (3.0 mmol) of 174 in 20 ml of DMF was treated with 0.2 g (8.3 mmol) of NaH at 23° C. for 0.2 hour. Ethyl bromoacetate (1.0 g, 6.0 mmol) was then added to the resultant suspension. The mixture was stirred at 23° C. for 16 hours then diluted with 150 ml of AcOEt. The organic layer was washed with H$_2$O (2×30 ml), brine (30 ml) and dried (MgSO$_4$). The solvent was removed at reduced pressure and the residue was purified by SiO$_2$ column chromatography (CH$_2$Cl$_2$/AcOEt 4:1) to give 1.9 g (90.8%) of 175 as a syrup. R$_f$ (CH$_2$Cl$_2$/AcOEt 4:1) 0.15; $^1$H NMR (CDCl$_3$): δ1.10 (s, 9H, (CH$_3$)$_3$-C), 1.28 (t, 3H, J=7.3 Hz, OCH$_2$CH$_3$), 1.61 (s, 3H, 5-CH$_3$), 1.76 (br s 1H, NH$_2$), 2.13 (ddd, 1H, J=13.5, 6.9, 6.8 Hz, 2'-H$_\alpha$), 2.30 (ddd, 1H, J=13.5, 6.2, 4.4 Hz, 2-H$_\beta$), 3.39 (s, 2H, NCH$_2$CO$_2$R), 3.52 (ddd, 1H, J=6.8, 5.1, 4.4 Hz, 3$^1$-H), 3.82 (dd, 1H, J=10.8, 2.83 Hz, 5'-CHH), 3.89 (ddd, 1H, J=5.1, 2.9, 2.8 Hz, 4'-H), 4.01 (dd, 1H, J=10.8, 2.9 Hz, 5'-CHH), 4.21 (q, 2H, J=7.3 Hz OCH$_2$CH$_3$), 4.71 (s, 2H, OCH$_2$Ph), 5.50 (s, 2H, NCH$_2$O), 6.30 (dd, 1H, J=6.9, 6.2 Hz, 1'-H), 7.25–7.53 (m, 13H, aromatic-H and 6-H), 7.66–7.69 (m, 4H, aromatic-H); $^{13}$C NMR (CDCl$_3$): δ12.93 (-, 5-CH$_3$), 14.31 (-, OCH$_2$CH$_3$), 19.42 (+, Me$_3$-C), 27.06 (-, Me$_3$-C), 38.99 (+, 2'-C), 49.14 (+, N—C—CO$_2$R), 57.83 (-, 3'-C), 61.02 (+, 5'-C), 64.32 (+, OCH$_2$CH$_3$), 70.57 (+, O—C—Ph), 72.19 (+, N—C—O), 85.54 (-, 1'- and -4'-C), 110.12 (+, 5-C), 127.68, 128.04, 128.30 (-, aromatic-C), 130.16 (-, 6-C), 132.56, 133.06 (+, aromatic-C), 134.18, 135.42, 135.61 (-, aromatic-C), 138.18 (+, aromatic-C), 150.95 (+, 2-C), 163.53 (+, 4-C), 172.05 (+, N—C—CO$_2$R).

EXAMPLE 180

N3-Benzyloxymethyl-3'-deoxy-3'-N- (2-hydroxyethyl) -5'-O-(tert-butyldiphenylsilyl) thymidine 176.

A solution of 1.8 g (2.6 mmol) of 175 in 20 ml of MeOH was treated with 1.0 g (26.4 mmol) of NaBH$_4$ in 4 portions at 23° C. for 2 hours. The solvent was removed at reduced pressure and the residue was redissolved in 100 ml of CHCl3. The insoluble material was filtered off through a B üchner funnel. The filtrate was concentrated at reduced pressure and the residue was purified by SiO$_2$ column chromatography (CHCl$_3$/MeOH 9:1) to give 1.2 g (68.8%) of 176 as a syrup. R$_f$ (CHCl$_3$/MeOH 4:1) 0.45; $^1$H NMR (CDCl$_3$): δ1.09 (s, 9H, (CH$_3$)$_3$-C) , 1.66 (s, 3H, 5-CH$_3$), 1.88 (br s 2H, OH and NH, D$_2$O exchangable), 2.16 (ddd, 1H, J=13.4, 7.1, 6.9 Hz, 2'-H$_\alpha$), 2.28 (ddd, 1H, J=13.4, 6.8, 4.6 Hz, 2-H$_\beta$), 2.73 (ABq then t, 2H, J=17.3, 5.0 Hz, NC H$_2$CH$_2$O), 3.48 (ddd, 1H, J=7.1, 5.2, 4.6 Hz, 3'-H), 3.64 (t, 2H, NCH$_2$CH$_2$O), 3.82 (dd, 1H, J=10.6, 2.9 Hz, 5'-CHH), 3.86 (ddd, 1H, J=5.2, 2.9, 2.3 Hz, 4'-H) , 4.00 (dd, 1H, J=10.6, 2.3 Hz, 5'-CHH), 4.21 (q, 2H, J=7.3 Hz, OCH$_2$CH$_3$), 4.70 (s, 2H, OCH$_2$Ph), 5.49 (s, 2H, NCH$_2$O), 6.27 (dd, 1H, J=6.9, 6.8 Hz, 1'-H), 7.24–7.48 (m, $^{13}$H, aromatic-H and 6-H), 7.65–7.68 (m, 4H, aromatic-H); $^{13}$C NMR (CDCl$_3$): δ12.95 (-, 5-CH$_3$), 19.45 (+, Me$_3$-C) , 27.09 (-, Me$_3$-C), 39.24 (+, 2'-C) , 49.77 (+, N—C—C—O), 58.29 (-, 3'-C), 61.28 (+, 5'-C), 64.46 (+, N—C—C—O), 70.62 (+, O—C—Ph), 72.26 (+, N—C—O), 85.58 (-, 1'- and -4'-C) , 110.2 (+, 5-C), 127.72, 128.04, 128.34 (-, aromatic-C), 130.13 (-, 6-C), 132.58, 133.07 (+, aromatic-C), 134.28, 135.42, 135.62 (-, aromatic-C), 138.06 (+, aromatic-C), 151.17 (+, 2-C), 163.62 (+, 4-C).

EXAMPLE 181

2'-Deoxy-xylo-thymidine 177.

A solution of 38.0 g (82.3 mmol) of 171 and 5.6 g (100.0 mmol) of KOH in 150 ml of MeOH was heated to reflux for 18 hours. The solvent was removed at reduced pressure and the residue was purified by SiO$_2$ column chromatography (CH$_2$Cl$_2$/AcOEt 10:1 then 3:1) to give 19.0 g (95.4%) of 177 as a light brown solid. R$_f$(CHCl$_3$/MeOH 3:1) 0.20; $^1$H NMR (DMSO-d$_6$): δ1.78 (s, 3H, 5-CH$_3$), 1.87 (dd, 1H, J=14.6, 2.5 Hz, 2'-H$_\alpha$), 2.57 (ddd, 1H, J=14.6, 8.3, 5.4 Hz, 2'-H$_\beta$), 3.61–3.84 (m, 3H, 4'- and 5'-H), 4.25 (m, 1H, 3'-H), 4.71 (t, 1H, J=5.4 Hz, 5'-OH), 5.27 (d, 1H, J=3.5 Hz, 3'-OH), 6.07 (dd, 1H, J=8.3, 2.5 Hz, 1'-H), 7.82 (s, 1H, 6-H), 11.30 (br s, 1H, NH).

EXAMPLE 182

2'-Deoxy-5'-O-(tert-butyldiphenylsilyl)-xylo-thymidine 178.

To a solution of 19.0 g (78.5 mmol) of 171 in 150 ml of pyridine was added 24.5 ml (25.9 g, 94.2 mmol) of TBDPS- Cl and 10 mg (8.2×10$^{-2}$ mmol) of DMAP. The reaction mixture was stirred at 23° C. for 18 hours. The solvent was removed at reduced pressure and the residue was purified by SiO$_2$ column chromatography (CH$_2$Cl$_2$/AcOEt 10:1) to give 36.4 g (96.6%) of 178 as a off-white foam. R$_f$ (CH$_2$Cl$_2$/MeOH 20:1) 0.16; $^1$H NMR (CDCl$_3$) δ1.08 (s, 9H, (CH$_3$)$_3$-C), 1.83 (s, 3H, 5-CH$_3$), 2.10 (dd, 1H, J=15.1, 2.8 Hz, 2'-H$_\alpha$), 2.46 (ddd, 1H, J=15.1, 8.3, 5.4 Hz, 2'-H$_\beta$), 3.68 (br s, 1H, OH), 3.85 (dd, 1H, J=7.8, 4.7 Hz, 4'-H), 4.11 (d, 2H, J=4.6 Hz, 5'-H), 4.56 (ddd, 1H, J=7.8, 5.4, 2.8 Hz, 3'-H), 6.24 (dd, 1H, J=8.3, 2.8 Hz, 1'-H), 7.27–7.51 (m, 6H, aromatic-H), 7.65–7.71 (m, 4H, aromatic-H), 7.75 (s, 1H, 6-H), 8.49 (br s, 1H, NH).

EXAMPLE 183

2'-Deoxy-3'-O-mesyl-5'-O-(tert-butyldiphenylsilyl)-xylo-thymidine 179.

A solution of 36.1 g (75.2 mmol) of 178 and 15.7 ml (11.4 g, 112.8 mmol) of Et$_3$N in 200 ml of CH$_2$Cl$_2$ was treated with 7.6 ml (11.2 g, 97.8 mmol) of MsCl at 0° C. for 4 hours. The solvent was removed at reduced pressure and the residue was purified by SiO$_2$ column chromatography (CH$_2$Cl$_2$/AcOEt 10:1) to give 40.7 g (96.7%) of product as a yellow foam. R$_f$ (CH$_2$Cl$_2$/MeOH 20:1) 0.45; $^1$H NMR (CDCl$_3$): δ1.08 (s, 9H, (CH$_3$)$_3$-C), 1.86 (s, 3H, 5-CH$_3$), 2.47 (ddd, 1H, J=15.8, 3.4, 1.5 Hz, 2'-H$_\alpha$), 2.81 (ddd, 1H, J=15.8, 8.1, 5.3 Hz, 2'-H$_\beta$), 2.95 (s, 3H, CH$_3$SO$_2$), 3.97–4.13 (m, 3H, 4'- and -5'-H), 5.30 (ddd, 1H, J=5.3, 4.0, 1.5 Hz, 3'-H), 6.26 (dd, 1H, J=8.1, 3.4 Hz, 1'-H), 7.30–7.51 (m, 7H, aromatic-H and 6-H), 7.65–7.71 (m, 4H, aromatic-H), 8.70 (br s, 1H, NH); $^{13}$C NMR (CDCl$_3$): δ12.61 (-, 5-CH$_3$), 19.23 (+, Me$_3$-$\underline{C}$), 26.88 (-, $\underline{Me}_3$-C), 38.55 (-, CH$_3$SO$_2$), 39.45 (+, 2'-C), 60.96 (+, 5'-C), 78.58 (-, 4'-C), 82.23 (-, 3'-C), 83.57 (-, 1'-C), 111.31 (+, 5-C), 127.97 (-, aromatic-C), 130.16 (-, 6-C), 132.57, 133.05 (+, aromatic-C), 135.25, 135.60 (-, aromatic-C), 150.72 (+, 2-C), 163.92 (+, 4-C).

EXAMPLE 184

3'-S-Methoxycarbomethyl-5'-O-(tert-butyldiphenylsilyl)thymidine 180.

To a solution of 179 33.0 g (59.1 mmol) and methylthioglycolate 6.9 ml (8.2 g, 76.9 mmol) in 100 ml of DMF was added 2.8 g (118.3 mmol) of NaH at 0° C. in one portion. The resultant suspension was stirred at 0° C. for 2 hours. The solvent was removed at reduced pressure and the residue was purified by SiO$_2$ column chromatography (hexanes/AcOEt 1:1) to give 30.8 g (91.7%) of 180 as a white solid. mp 156–158° C.; R$_f$ (hexanes/AcOEt 1:1) 0.23; $^1$H NMR (CDCl$_3$): δ1.10 (s, 9H, (CH$_3$)$_3$-C), 1.60 (s, 3H, 5-CH$_3$), 2.47 (t, 2H, J=6.2 Hz, 2'-H), 3.28 (s, 2H, S—CH$_2$), 3.72 (s, 3H, CO$_2$C$\underline{H}_3$), 3.79 (d, 1H, J=6.6 Hz, 3'-H), 3.86 (dd, 1H, J=11.5, 2.7 Hz, 5'-C$\underline{H}$H), 3.94 (ddd, 1H, J=6.6, 2.7, 2.0 Hz, 4'-H), 4.08 (dd, 1H, J=11.5, 2.0 Hz, 5-CH$\underline{H}$) , 6.27 (t, 1H, J=6.2 Hz, 1'-H) , 7.26–7.50 (m, 7H, aromatic-H and 6-H), 7.65–7.71 (m, 4H, aromatic-H), 9.00 (br s, 1H, NH, D$_2$O exchangable); $^{13}$C NMR (CDCl$_3$): δ12.16 (-, 5-CH$_3$), 19.48 (+, Me$_3$-$\underline{C}$), 27.04 (-, $\underline{Me}_3$-C), 33.15 (+, S—C—CO$_2$R), 39.75 (+, 2'-C), 41.94 (-, CO$_2$$\underline{Me}$), 52.67 (-, 3'-C), 63.34 (+, 5'-C), 84.32 (-, 4'-C), 85.18 (-, 1'-C), 111.28 (+, 5-C), 127.68, 128.03 (-, aromatic-C), 130.13 (-, 6-C), 132.45, 132.96 (+, aromatic-C), 135.37, 135.60 (-, aromatic-C), 150.56 (+, 2-C), 164.12 (+, 4-C), 170.37 (+, $\underline{C}$O$_2$Me); *Anal. Calcd.* for C$_{29}$H$_{36}$N$_2$SSi: C, 61.26; H, 6.34; N, 4.94. Found: C, 60.97; H, 6.43; N, 4.93.

EXAMPLE 185

N3-Benzoxymethyl-3'-S-methoxycarbomethyl-5'-O-(tert-butyldi-phenylsilyl)thymidine 181.

To a solution of 4.7 g (8.3 mmol) of 180 in 100 ml of CH$_2$Cl$_2$ was added 3.6 ml (2.7 g, 20.7 mmol) of Hunig's base and 2.1 ml (2.3 g, 14.9 mmol) of benzyloxymethyl chloride at 23° C. under an atmosphere of argon. The resultant mixture was stirred at 23° C. for 16 hours. The solvent was removed at reduced pressure and the residue was purified by SiO$_2$ column chromatography (hexanes/AcOEt 3:1 then 1:1) to give 2.5 g (43.9%) of 181 as a syrup. R$_f$ (hexanes/AcOEt 1:1) 0.41; $^1$H NMR (CDCl$_3$): δ1.10 (s, 9H, (CH$_3$)$_3$-C), 1.60 (s, 3H, 5-CH$_3$), 2.46 (t, 2H, J=6.8 Hz, 2'-H), 3.28 (s, 2H, S—CH$_2$), 3.72 (s, 3H, CO$_2$C$\underline{H}_3$), 3.76 (d, 1H, J=6.8 Hz, 3'-H), 3.86 (dd, 1H, J=11.5, 2.6 Hz, 5'-C$\underline{H}$H), 3.94 (ddd, 1H, J=6.5, 2.6, 1.8 Hz, 4'-H), 4.08 (dd, 1H, J=11.5, 1.8 Hz, 5-CH$\underline{H}$), 4.71 (s, 2H, OCH$_2$Ph), 5.49 (s, 2H, NCH$_2$O), 6.27 (t, 1H, J=6.6 Hz, 1'-H), 7.26–7.49 (m, 7H, aromatic-H and 6-H), 7.64–7.71 (m, 4H, aromatic-H); $^{13}$C NMR (CDCl$_3$): δ12.86 (-, 5-CH$_3$) , 19.48 (+, Me$_3$-$\underline{C}$) , 27.00 (-, $\underline{Me}_3$-C), 33.03 (+, S—C—CO$_2$R) , 39.85 (+, 2'-C) , 41.80 (-, CO$_2$$\underline{Me}$) 52.56 (-, 3'-C), 63.33 (+, 5'-C), 70.61 (+, O—C—Ph), 72.21 (+, N—C—O), 85.07 (-, 4'-C), 85.24 (-, 1'-C), 110.30 (+, 5-C), 127.64, 128.06, 128.30 (-, aromatic-C), 130.13 (-, 6-C), 132.50, 133.02 (+, aromatic-C), 134.12, 135.38, 135.60 (-, aromatic-C), 138.20 (+, aromatic-C), 150.94 (+, 2-C), 163.39 (+, 4-C) , 170.26 (+, $\underline{C}$O$_2$Me) ; *Anal. Calcd.* for C$_{37}$H$_{44}$N$_2$O$_7$SSi: C, 64.53; H, 6.40; N, 4.07. Found: C, 64.91; H, 6.47; N, 3.71.

EXAMPLE 186

N3-Benzoxymethyl-3'-S-(2-hydroxyethyl) -5'-O-(tert-butyldi-phenylsilyl)thymidine 182.

To a solution of 2.5 g (3.6 mmol) of 181 in 50 ml of MeOH was added 0.4 g (10.6 mmol) of NaBH$_4$ in 4 portions at 0° C. The resultant suspension was stirred at 0° C. for 1 hour. The solvent was removed at reduced pressure and the residue was purified by SiO$_2$ column chromatography (hexanes/AcOEt 3:1 then 1:1) to give 2.2 g (93.3%) of 182 as a white foam. R$_f$ (hexanes/AcOEt 1:1) 0.27; $^1$H NMR (CDCl$_3$): δ1.12 (s, 9H, (CH$_3$)$_3$-C), 1.61 (s, 3H, 5-CH$_3$), 2.12 (br s, 1H, OH), 2.44 (m, 2H, 2'-H), 2.75 (t, 2H, J=6.0 Hz, SC$\underline{H}_2$CH$_2$OH), 3.56 (ddd, 1H, J=7.3, 5.8, 5.6 Hz, 3'-H), 3.73 (m, 2H, SCH$_2$C$\underline{H}_2$OH), 3.87 (dd, 1H, J=11.7, 2.7 Hz, 5'-C$\underline{H}$H), 3.92 (ddd, 1H, J=5.8, 2.7, 2.1 Hz, 4'-H), 4.11 (dd, 1H, J=11.7, 2.1 Hz, 5-CH$\underline{H}$), 4.71 (s, 2H, OCH$_2$Ph), 5.49 (s, 2H, NCH$_2$O), 6.23 (t, 1H, J=6.6 Hz, 1''-H), 7.26–7.49 (m, 7H, aromatic-H and 6-H), 7.64–7.71 (m, 4H, aromatic-H) ; $^{13}$C NMR (CDCl$_3$) d 12.91 (-, 5-CH$_3$), 19.55 (+, Me$_3$-$\underline{C}$), 27.17 (-, $\underline{Me}_3$-C), 34.45 (+, S—C—$\underline{C}$—O), 40.61 (+, 2'-C), 41.17 (-, 3'-C), 61.49 (+, 5'-C), 63.16 (+, S—C—$\underline{C}$—O), 64.96 (+, 4'-C) , 70.65 (+, O—C—Ph), 72.31 (+, N—C—O) , 85.94 (-, 1'-C), 110.28 (+, 5-C), 127.00, 127.47, 127.75, 128.39 (-, aromatic-C), 130.13 (-, 6-C), 132.56, 133.04 (+, aromatic-C), 134.28, 135.42, 135.63 (-, aromatic-C), 138.04 (+, aromatic-C), 150.95 (+, 2-C) , 163.65 (+, 4-C) ; *Anal. Calcd.* for C$_{36}$H$_{44}$N$_2$O$_6$SSi H$_2$O: C, 63.72; H, 6.78; N, 4.13. Found: C, 63.42; H, 6.63; N, 4.05.

EXAMPLE 187

5'-O-(tert-butyldiphenylsilyl)-3'-deoxy-3'-C-(acetoxymethyl)-thymidine 183.

Compound 106 (0.5 g, 1.01 mmol) was dissolved in pyridine (10 ml) and acetic anhydride (0.20 ml, 2.12 mmol) was added under an argon atmosphere at room temperature. After being stirred for 24 hours at 20° C., the pyridine was removed in vacuo to give an oil. The oil was diluted with CH$_2$Cl$_2$ (20 ml) and washed with water (20 ml) and saturated NaHCO$_3$ (20 ml). The organic layer was dried over anhydrous MgSO$_4$ and the solvent was evaporated in vacuo to give a white foam. The foam was then purified by flash chromatography in EtOAc/Hexane (6:4) to give 183 (0.44 g, 81%) as a white foam. Tlc ($R_f$ 0.80; EtOAc); $^1$H NMR (CDCl$_3$): δ8.93 (br, 1 H, NH), 7.69–7.66 (m, 4 H, Ph), 7.48 (d, 1 H, J=1.1 Hz, H-6), 7.46–7.37 (m, 6 H, Ph), 6.17 (dd, 1 H, J=5.7, 6.7 Hz, H-1'), 4.09–4.05 (m, 3 H, H-5' & C$\underline{H}_2$-OAc), 3.93–3.91 (m, 1 H, H-5'), 3.79 (dd 1 H, J=11.5, 3.2 Hz, H-5"), 2.80–2.78 (m, 1 H, H-3'), 2.33–2.21 (m, 1 H, H-2'), 2.19–2.16 (m, 1 H, H-2"), 2.03 (s, 3 H, COCH$_3$), 1.62 (s, 3 H, CH$_3$), 1.10 (s, 9 H, C(CH$_3$)$_3$); $^{13}$C NMR (CDCl$_3$): δ170.7 (C=O), 163.7 (C4), 150.3 (C2), 135.5–135.2 (d), 133.0, 132.5, 130.1 (C6), 127.9–127.8 (d), 110.9 (C5), 84.7 (C1'), 82.9 (C4'), 64.4 (C$\underline{H}_2$-OAc), 64.2 (C5'), 37.3 (C3'), 35.8 (C2'), 26.9, 20.8, 19.4, 12.1; Anal. Calcd for C$_{29}$H$_{36}$N$_2$O$_6$Si (536.699): C, 64.90; H, 6.76; N, 5.22. Found: C, 64.57; H 6.79; N, 5.12.

EXAMPLE 188

3'-Deoxy-3'-C-(acetoxymethyl)thymidine 184.

Compound 183 (2.00 g, 3.73 mmol) was dissolved in dry THF (36 ml) and tetrabutylammonium fluoride (8.8 ml, 1.0 M solution in THF, 2.4 equiv.) was added via syringe at room temperature under an atmosphere of argon. After completion of the reaction (1.5 hours), as was monitored by tlc in EtOAc ($R_f$ 0.42), the solvent was removed in vacuo. The residue was purified by silica gel flash column chromatography in EtOAc/Hexane (4:6–9:1, v/v) to afford 184 (0.63 g, 57%) $^1$H NMR (CDCl$_3$): δ8.89 (br, 1 H, NH), 7.55 (d, 1 H, J=1.1 Hz, H6), 6.13 (dd, 1 H, J=4.9, 6.6 Hz, H-1'), 4.17 & 4.09 (m, 2 H, C$\underline{H}_2$-OAc), 4.07 (d, 1 H, J=11.7 Hz, H-5' & H-5'), 3.94–3.90 (m, 1 H, H-4'), 3.76 (d, 1H, J=11.7 Hz, H-5), 2.80–2.76 (m, 1 H, H-3'), 2.60 (br, 1 H, OH), 2.29–2.25 (m, 2 H, H2' & H-2"), 2.09 (s, 3 H, COCH$_3$), 1.91 (s, 9 H, C(CH$_3$)$_3$); $^{13}$C NMR (CDCl$_3$): 170.8 (C=O), 163.8 (C4), 150.3 (C2), 136.3 (C6), 110.8 (C5), 85.4 (C1'), 83.5 (C4'), 64.2 (C5'), 36.8 (C3'), 35 35.6 (C2'), 20.8, 12.5;

EXAMPLE 189

5'-O-(Dimethoxytriphenylmethyl)-3'-deoxy-3'-C-(acetoxymethyl)-thymidine 185.

Compound 184 (0.50 g, 1.68 mmol) was coevaporated twice with dry pyridine and redissolved in pyridine (10 ml) under an atmosphere of argon. 4, 4'-Dimethoxytrityl chloride (1.14 g, 3.36 mmol) was added slowly, and the mixture was stirred for 24 hours at room temperature. The reaction was quenched with 5 ml of MeOH and the solvent was removed in vacuo. The mixture was dissolved in 30 ml of CH$_2$Cl$_2$ and washed with NaHCO$_3$ (30 ml), and brine. The organic layer was dried over Na$_2$SO$_{4}$, filtered and concentrated in vacuo. The residue was purified by column chromatography on silica gel (CH$_2$Cl$_2$/EtOAc/Et$_3$N 95:5:0.3% –80:20:0.3%, v/v/v) to give 185 (0.91 g, 90%). $^1$H NMR (CDCl$_3$): δ8.63 (br, 1 H, NH), 7.71 (m, 1 H, Tr), 7.41 (d, 1 H, J=1.1 Hz, H6), 7.32–7.25 (m, 9 H, Tr), 6.85–6.81 (m, 4 H, Tr), 6.15 (dd, 1 H, J=4.7, 6.7 Hz, H-1'), 4.06 & 4.01 (m, 2 H, CH$_2$-OAc), 3.99–3.96 (m, 1 H, H-4'), 3.79 (s, 6 H, OCH$_3$), 3.61 (dd, 2 H, 3.6, 10.7 Hz, H-5'), 3.30 (dd, 1H, J=3.6, 10.7 Hz, 5"), 2.85–2.79 (m, 1 H, H-3'), 2.30–2.25 (m, 2 H, H-2' & H-2"), 1.93.(s, 3 H, COCH$_3$), 1.44 (s, 3 H, CH$_3$); $^{13}$C NMR (CDCl$_3$): 170.7, 163 6 (C4), 158.7, 150.1 (C2), 144.4, 135.5 (C6), 130.1, 128.2 & 127.9 (d), 127.1, 123.8, 113.2, 110.7 (C5), 86.7, 85.0 (C1'), 82.7 (C4'), 64.3 (C5'), 55.2, 37.3, 36.3, 20.7, 11.8; Anal. Calcd for C$_{34}$H$_{36}$N$_2$O$_8$Si (628.753): C, 67.99; H, 6.04; N, 4.66. Found: C, 67.85; H 6.11; N, 4.80.

EXAMPLE 190

5'-O-(Dimethoxytriphenylmethyl)-3'-deoxy-3'-methyl-thymidine 186.

Compound 185 (0.70 g, 1.17 mmol) was dissolved in dry methanol. The reaction was cooled to 0° C. and NH3 in MeOH (1.5 ml, Ca. 9 M) was added dropwise via syringe. The reaction mixture was allowed to warm gradually to room temperature. After stirring for 24 hours the solution was concentrated to dryness, and the residue was chromatographed on a silica gel column with EtOAc/Hexane (6:4–8:2) as eluent to give 186 (0.40 g, 61%). $^1$H NMR (CDCl$_3$): δ8.68 (br, 1 H, NH), 7.61 (m, 1 H, Tr), 7.43 (d, 1 H, J=1.1 Hz, H-6), 7.33–7.28 (m, 9 H, Tr), 6.85–6.82 (m, 4 H, Tr), 6.14 (dd, 1 H, J=4.7, 6.7 Hz, H-1'), 3.99–3.97 (m, 1 H, H-4'), 3.79 (s, 6 H, OCH$_3$), 3.64–3.61 (m, 2 H, CH$_2$OH), 3.51 (dd, 2 H, J=3,6, 10.5 Hz, H-5') 3.36 (dd, 1H, J=3.6, 10.5 Hz, H-5"), 2.62–2.60 (m, 1 H, H-3'), 2.35–2.31 (m, 1 H, H-2'), 2.24–2.20 (m, 1 H, H-2"), 2.12 (m, 1 H, OH), 2.05 (s, 3 H, COCH$_3$), 1.52 (s, 3 H, CH$_3$); $^{13}$C NMR (CDCl$_3$): 163.7 (C4), 158.6, 150.3 (C2), 144.3, 135.7 (C6), 135.4, 130.1, 128.0 & 127.9 (d), 127.1, 113.2, 110.7 (C5), 86.9, 85.1 (C1'), 82.3 (C4'), 64.1 (C5'), 63.1, 55.2, 41.5 (C3'), 32.8 (C2'), 12.0.

EXAMPLE 191

3"-O-(β-Cyanoethyldiisopropylaminophosphiryl)-3'-deoxy-5'-O-(dimethoxytriphenylmethyl)-3'-C-(hydroxymethyl)thymidine 187.

Compound 186 (0.51 g, 0.91 mmol) was coevaporated twice with dry pyridine, once with dry acetonitrile, and then dissolved in dry THF (14 ml). N, N-diisopropylethylamine (0.50 ml, 2.87 mmol) were added at room temperature under an atmosphere of argon. The reaction mixture was cooled to 0° C. and 2-cyanoethyl N,N-diisopropylchlorophosphoramidite (0.50 ml, 2.11 mmole) was added slowly by syringe. The reaction was allowed to warm to room temperature. After stirring for 2 hours the tlc indicated that all the starting material had been converted into a new product ($R_f$ 0.72; 7:3 EtOAc/Hexane). The mixture was poured into cold saturated NaHCO$_3$ (30 ml) and extracted with EtOAc (2×30 ml). The organic layer was dried over Na$_2$SO$_4$, filtered and concentrated in vacuo. The residue was purified by medium-pressure chromatography on silica gel using a gradient of 3% triethylamine in CH$_2$Cl$_2$ and going to 1% MeOH and 3% triethylamine in CH$_2$Cl$_2$ as eluant to give 187 (0.39 g, 56%) as a white foam. $^1$H NMR (CDCl$_3$): δ8.90 (br, 1 H, NH), 7.49–7.42 (m, 2 H, H-6 & Tr), 7.43–7.28 (m, 9 H, Tr), 6.10 35 (dd, 1 H, J=5.1, 6.7 Hz, H1'), 4.00 (m, 1 H, H-4'), 3.75 (s, 6 H, OCH$_3$), 3.71–3.60 (m, 3 H, C$\underline{H}_2$O$\underline{H}$), 3.57–3.50 (m, 2 H, CNCH$_2$C$\underline{H}_2$O), 3.39–3.35 (m, 1 H, H-5'), 3.37–3.33 (m, 1 H, H-5"), 2.64–2.53 (m, 3 H, H-3' & CNC$\underline{H}_2$CH$_2$O), 2.30–2.14 (m, 2 H, H-2' & H-2"), 1.91 (s, 3 H, CH$_3$), 1.16–1.08 (dd, 12 H, N(C(CH$_3$)$_3$); $^{31}$P NMR (CDCl$_3$) δ+148.1 & +147.9 (d).

EXAMPLE 192

Oligonucleotide Containing 5-atom, e.g. [—CH$_2$—O—P(=O)(OH)—O—CH$_2$—], Phosphate Linkage.

Compound 187 was further used to prepare a 5 atom phosphate linkage between adjacent nucleosides that corresponds to a normal phosphate linkage with the exception that an additional methylene group is positioned immediately adjacent the 3' carbon atom of the sugar. ring of the 5'-terminus nucleoside and repositions the oxygen atom that would normally occupy that position one atom further away from that sugar 3' carbon atom. Oligonucleotides incorporating this linkage were prepared utilizing standard solid state phosphoramidite synthesis procedures on a standard DNA synthesizer. Compound 187 was used in the normal manner as the phosphoramidite being added during the appropriate cycle of the synthesizer. Several oligonucleotides containing this linkage were prepared, including the oligonucleotides of the sequence:

5' CTCGTACCT*TCCGGTCC 3' (SEQ ID NO:1)
5' CTCGTACT*T*TCCGGTCC 3' (SEQ ID NO:2)
5' GCCT*TT*TT*TT*TT*TGCG 3' (SEQ ID NO:3)
5' GCCT*T*T*T*T*T*T*T*T*TGCG 3' (SEQ ID NO:3)

wherein the T*T pair were connected via this 5 atom phosphate linkage.

EVALUATION

Procedure 1 - Nuclease Resistance

A. Evaluation of the resistance of oligonucleotide-mimicking macromolecules to serum and cytoplasmic nucleases.

Oligonucleotide-mimicking macromolecules of the invention can be assessed for their resistance to serum nucleases by incubation of the oligonucleotide-mimicking macromolecules in media containing various concentrations of fetal calf serum or adult human serum. Labeled oligonucleotide-mimicking macromolecules are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide-mimicking macromolecules it is possible to determine the effect on nuclease degradation by the particular modification. For the cytoplasmic nucleases, an HL 60 cell line can be used. A post-mitochondrial supernatant is prepared by differential centrifugation and the labelled macromolecules are incubated in this supernatant for various times. Following the incubation, macromolecules are assessed for degradation as outlined above for serum nucleolytic degradation. Autoradiography results are quantitated for evaluation of the macromolecules of the invention. It is expected that the macromolecules will be completely resistant to serum and cytoplasmic nucleases.

B. Evaluation of the resistance of oligonucleotide-mimicking macromolecules to specific endo- and exo-nucleases.

Evaluation of the resistance of natural oligonucleotides and oligonucleotide-mimicking macromolecules of the invention to specific nucleases (i.e., endonucleases, 3',5'-exo-, and 5', 3'-exonucleases) can be done to determine the exact effect of the macromolecule linkage on degradation. The oligonucleotide-mimicking macromolecules are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the macromolecules linkage are determined for specific nucleases and compared with the results obtained from the serum and cytoplasmic systems. As with the serum and cytoplasmic nucleases, it is expected that the oligonucleotide-mimicking macromolecules of the invention will be completely resistant to endo- and exo-nucleases.

Procedure 2–5-Lipoxygenase Analysis and Assays

A. Therapeutics

For therapeutic use, an animal suspected of having a disease characterized by excessive or abnormal supply of 5-lipoxygenase is treated by administering the macromolecule of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotide-mimicking macromolecules of this invention will also be useful as research reagents when used to cleave or otherwise modulate 5-lipoxygenase MRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 300 to about 500° C. The cleaved 5-lipoxygenase RNA can be analyzed by agarose gel electrophoresis and hybridization with radiolabeled DNA probes or by other standard methods.

C. Diagnostics

The oligonucleotide-mimicking macromolecules of the invention will also be useful in diagnostic applications, particularly for the determination of the expression of specific MRNA species in various tissues or the expression of abnormal or mutant RNA species. In this example, while the macromolecules target a abnormal MRNA by being designed complementary to the abnormal sequence, they would not hybridize to normal MRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the MRNA would bind to the solid support. The 3' region of the abnormal RNA, which is cleaved, would not be bound to the support and therefore would be separated from the normal MRNA.

Targeted MRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase) Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotide-mimicking macromolecules which interfere with 5-lipoxygenase synthesis in these cells.

A second test system for oligonucleotide-mimicking macromolecules makes use of the fact that 5-lipoxygenase is a "suicide" enzyme in that it inactivates itself upon reacting with substrate. Treatment of differentiated HL-60 or other cells expressing 5 lipoxygenase, with 10 µM A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotide-mimicking macromolecules can exert on intact cells and which can be easily be quantitated is specific inhibition of 5-lipoxygenase protein synthesis. To perform this technique, cells can be labelled with $^{35}$S-methionine (50 µCi/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 µM, 10 µM, and 30 µM of the macromolecules of the invention for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 µM $^{14}$C-arachidonic acid, 2 mM ATP, 50 µM free calcium, 100 µg/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 µM, 10 µM, and 30 µM would be as follows. Control cells oxidize 200 pmol arachidonic acid/5 min/$10^6$ cells. Cells treated with 1 µM, 10 µM, and 30 µM of an effective oligonucleotide-mimicking macromolecule would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in E. coli and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris●HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 µL in the microtiter wells for 90 min. The antibodies are prepared by immunizing rabbits with purified human recombinant 5-lipoxygenase. The wells are washed with TBS containing 0.05% tween 20 (TBST), then incubated with 100 µL of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer oligonucleotide-mimicking macromolecule at 1 µM, 10 µM, and 30 µM would be 30 ng, 18 ng and 5 ng of 5-lipoxygenase per $10_6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.) Leukotriene B4 production can be detected in HL-60 cells 48 hours following addition of DMSO to differentiate the cells into a neutrophil-like cell. Cells (2×$10^5$ cells/mL) will be treated with increasing concentrations of the macromolecule for 48–72 hours in the presence of 1.3% DMSO. The cells are washed and resuspended at a concentration of 2×$10^6$ cell/mL in Dulbecco's phosphate buffered saline containing 1% delipidated bovine serum albumin. Cells are stimulated with 10 µM calcium ionophore A23187 for 15 min and the quantity of LTB4 produced from 5×$10^5$ cell determined by radioimmunoassay as described by the manufacturer.

Using this assay the following results would likely be obtained with an oligonucleotide-mimicking macromolecule directed to the 5-LO MRNA. Cells will be treated for 72 hours with either 1 µM, 10 µM or 30 µM of the macromolecule in the presence of 1.3% DMSO. The quantity of $LTB_4$ produced from 5×$10^5$ cells would be expected to be about 75 pg, 50 pg, and 35 pg, respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$, leukotriene C4 and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oligonucleotide-mimicking macromolecules will be applied topically to both ears 12 to 24 hours prior to administration of arachidonic acid to allow optimal activity of the compounds. Both ears are pretreated for 24 hours with either 0 1 µmol, 0.3 µmol, or 1.0 µmol of the macromolecule prior to challenge with arachidonic acid. Values are expressed as the mean for three animals per concentration. Inhibition of polymorphonuclear cell infiltration for 0.1 µmol, 0.3 µmol, and 1 µmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. A compound having structure:

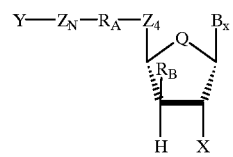

wherein:

$R_A$ is $CR_{3a}R_{3b}$, $CR_{2a}R_{2b}$-$CR_{3a}R_{3b}$, $CR_{2a}R_{2b}$-$Z_3$, $Z_2$-$CR_{3a}R_{3b}$ or $Z_2$-$Z_3$;

$Z_2$, $Z_3$ and $Z_4$ are, independently, O, S, $NR_4$, Se, $P(=J_1)J_2$ or $Si(R_6)_2$;

$Z_N$ is $CR_{1a}R_{1b}$, $NR_4$, S, Se, $P(=J_1)J_2$, Si $(R_6)_2$, or O;

$R_{1a}$, $R_{1b}$, $R_{2a}$, $R_{2b}$, $R_{3a}$ and $R_{3b}$ are, independently, H, $R_5$, O-$R_5$, S-$R_5$, NR$_4$R$_5$; or, independently, together $R_{1a}$ and $R_{1b}$, or $R_{2a}$ and $R_{2b}$, or $R_{3a}$ and $R_{3b}$ are=O;

$J_1$ is O, S, Se or NR$_4$;

$J_2$ is OH, OR$_5$, SH, SR$_5$, SeH, R$_5$, BH$_3$ or NR$_4$R$_5$;

$R_4$, $R_5$ and $R_6$ are, independently, H; $C_1$ to $C_{10}$ straight or branched chain lower alkyl or substituted lower alkyl; $C_2$ to $C_{10}$ straight or branched chain lower alkenyl or substituted lower alkenyl; $C_2$ to $C_{10}$ straight or branched chain lower alkynyl or substituted lower alkynyl; a $^{14}$C containing lower alkyl, lower alkenyl or lower alkynyl; $C_7$ to $C_{14}$ substituted or unsubstituted alkaryl or aralkyl; a $^{14}$C containing $C_7$ to $C_{14}$ alkaryl or aralkyl; $C_6$ to $C_{14}$ aryl; alicyclic; heterocyclic; or a reporter molecule;

$R_B$ is trifluoromethylsulfonyl, methylsulfonyl, halogen O-trichloroacetimidate, acyloxy, dialkyl phosphite, 2,4,6-trichlorophenyl, p-toluenesulfonyl, 4-dimethylaminoazobenzene-sulfonyl or 5-dimethylaminonaphthalenesulfonyl;

Y is H, halogen, a labile functional group or a blocking group;

X is H, OH, $C_1$ to $C_{10}$ lower alkyl, substituted lower alkyl, alkaryl or aralkyl, F, Cl, Br, CN, CF$_3$, OCF$_3$, OCN, O-alkyl, S-alkyl, N-alkyl, O-alkenyl, S-alkenyl, N-alkenyl, SOCH$_3$, SO$_2$CH$_3$, ONO$_2$, NO$_2$, N$_3$, NH$_2$, heterocycloalkaryl, aminoalkylamino, polyalkylamino or substituted silyl;

Q is O, CH$_2$, CHF, CF$_2$; and

B$_X$ is a heterocyclic base.

2. The compound of claim 1 wherein Y is an acid labile functional group.

3. The compound of claim 1 wherein Y is halogen.

4. A compound having structure:

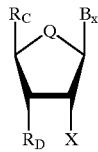

wherein:

$R_c$ is OH, SH, NH$_2$, trifluoromethylsulfonyl, methylsulfonyl, halogens, O-trichloroacetimidate, acyloxy, dialkyl phosphite, 2,4,6-trichlorophenyl, p-toluenesulfonyl, 4-dimethylaminoazobenzenesulfonyl or 5-dimethylaminonaphthalenesulfonyl;

$R_D$ is hydroxyl, $Z_T$, $L_1$-$Z_T$, $L_1$-$L_2$-$Z_T$, $L_1$-$L_2$-$L_3$-$Z_T$, a nucleoside, a nucleotide, an oligonucleotide or an oligonucleoside;

$L_1$ is $Z_1$ or CR$_{1a}$R$_{1b}$;

$L_2$ is $Z_2$ or CR$_{2a}$R$_{2b}$;

$L_3$ is $Z_3$ or CR$_{3a}$R$_{3b}$;

$Z_1$, $Z_2$, $Z_3$ and $Z_4$ are, independently, O, NR$_4$, S, SO, SO$_2$, Se, P(=J$_1$) J$_2$ or Si(R$_5$)$_2$;

$Z_T$ is $_{NR4}$H, SH, SeH, P(=J$_1$)J$_2$OH, Si(R$_6$)$_2$OH, or OH;

$R_{1a}$, $R_{1b}$, $R_{2a}$, $R_{2b}$, $R_{3a}$ and $R_{3b}$ are, independently, H, R$_5$, O—R$_5$, S—R$_5$, NR$_4$R$_5$; or, independently, together $R_{1a}$ and $R_{1b}$, or $R_{2a}$ and $R_{2b}$, or $R_{3a}$ and $R_{3b}$ are=O;

$J_1$ is O, S, Se or NR$_4$;

$J_2$ is OH, OR$_5$, SH, SR$_5$, SeH, R$_5$, BH$_3$ or NR$_4$R$_5$;

$R_4$, $R_5$ and $R_6$ are, independently, H; $C_1$ to $C_{10}$ straight or branched chain lower alkyl or substituted lower alkyl; $C_2$ to $C_{10}$ straight or branched chain lower alkenyl or substituted lower alkenyl; $C_2$ to $C_{10}$ straight or branched chain lower alkynyl or substituted lower alkynyl; a $^{14}$C containing lower alkyl, lower alkenyl or lower alkynyl; $C_7$ to $C_{14}$ substituted or unsubstituted alkaryl or aralkyl; a $^{14}$C containing C7 to $C_{14}$ alkaryl or aralkyl; $C_6$ to C14 aryl; alicyclic; heterocyclic; or a reporter molecule;

X is H, OH, $C_1$ to $C_{10}$ lower alkyl, substituted lower alkyl, alkaryl or aralkyl, F, Cl, Br, CN, CF$_3$, OCF$_3$, OCN, O-alkyl, S-alkyl, N-alkyl, O-alkenyl, S-alkenyl, N-alkenyl, SOCH$_3$, SO$_2$CH$_3$, ONO$_2$, NO$_2$, N$_3$, NH$_2$, heterocycloalkaryl, aminoalkylamino, polyalkylamino or substituted silyl;

Q is O, CH$_2$, CHF or CF$_2$; and

B$_x$ is a heterocyclic base.

5. The compound of claim 4 wherein said RC has formula OC(O)—R$_5$; and where R$_5$ is $C_1$–$C_{10}$ straight chain or branch chain alkyl.

6. The compound of claim 4 wherein said RC is OC(O) CH$_3$.

7. A method for forming a covalent linkage having structure:

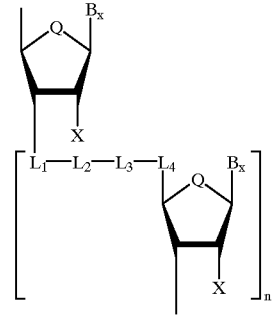

comprising the steps of:

a) providing a first compound having structure;

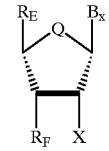

wherein:

$L_1$-$L_2$-$L_3$-$L_4$ is CR$_{1a}$R$_{1b}$-CR$_{2a}$-R$_{2b}$-CR$_{3a}$-R$_{3b}$-Z$_4$, CR$_{1a}$R$_{1b}$-CR$_{2a}$-R$_{2b}$-Z$_3$-Z$_4$, CR$_{1a}$R$_{1b}$-Z$_2$-CR$_{2a}$R$_{2b}$-4, Z$_1$-CR$_{1a}$R$_{1b}$-CR$_{2a}$R$_{2b}$Z$_4$, CR$_{1a}$R$_{1b}$-Z$_2$-Z$_3$-Z$_4$, Z$_1$-CR$_{2a}$R$_{2b}$-Z$_3$-Z$_4$ or Z$_1$-Z$_2$-CR$_{3a}$R$_{3b}$-Z$_4$;

$R_E$ is Y-Z$_N$-R$_A$-Z$_4$;

$Z_2$, $Z_3$ and $Z_4$ are, independently, O, S, NR$_4$, Se, P(=j$_1$)J$_2$ or Si(R$_6$)$_2$;

$R_A$ is CR$_{3a}$R$_{3b}$, CR$_{2a}$R$_{2b}$-CR$_{3a}$R$_{3b}$, CR$_{2a}$R$_{2b}$-Z$_3$, Z$_2$-CR$_{3a}$R$_{3b}$ or Z$_2$-Z$_3$;

$Z_N$ is $_{CR1a}$R$_{1b}$, NR$_4$, S, Se, P(=J$_1$)J$_2$, Si(R$_6$)$_2$, or O;

Y is a labile functional group;

$R_{1a}$, $R_{1b}$, $R_{2a}$, $R_{2b}$, $R_{3a}$ and $R_{3b}$ are, independently, H, R$_5$, O-R$_5$, S-R$_5$, NR$_4$R$_5$; or, independently, together $R_{1a}$ and $R_{1b}$, or $R_{2a}$ and $R_{2b}$, or $R_{3a}$ and $R_{3b}$ are=O;

$J_1$ is O, S, Se or $NR_4$;

$J_2$ is OH, $OR_5$, SH, $SR_5$, SeH, $R_5$, $BH_3$ or $NR_4R_5$;

$R_4$, $R_5$ and $R_6$ are, independently, H; $C_1$ to $C_{10}$ straight or branched chain lower alkyl or substituted lower alkyl; $C_2$ to $C_{10}$ straight or branched chain lower alkenyl or substituted lower alkenyl; $C_2$ to $C_{10}$ straight or branched chain lower alkynyl or substituted lower alkynyl; a $^{14}C$ containing lower alkyl, lower alkenyl or lower alkynyl; $C_7$ to $C_{14}$ substituted or unsubstituted alkaryl or aralkyl; a $^{14}C$ containing $C_7$ to $C_{14}$ alkaryl or aralkyl; $C_6$ to $C_{14}$ aryl; alicyclic; heterocyclic; or a reporter molecule;

X is H, OH, $C_1$ to $C_{10}$ lower alkyl, substituted lower alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, SO2CH3, ONO2, NO2, N3, NH2, heterocycloalkyl, heterocycloalkaryl, aminoalkylamino, polyalkylamino or substituted silyl;

Q is O or $CH_2$;

Bx is a heterocyclic base;

b) removing said Y group in a manner generating an anion at $Z_N$; and c) reacting said first compound having said anion thereon with a second compound of the structure:

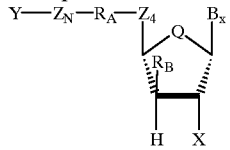

wherein:

$R_B$ is trifluoromethylsulfonyl, methylsulfonyl, halogen, O-trichloroacetimidate, acyloxy, dialkyl phosphite, 2,4, 6-trichlorophenyl, p-toluenesulfonyl, 4-dimethylaminoazobenzene-sulfonyl or 5-dimethylaminonaphthalenesulfonyl.

8. A method for forming a covalent linkage having structure:

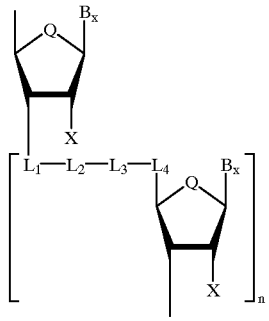

comprising the steps of:

providing a first compound having structure:

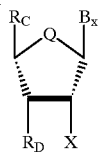

contacting said first compound with a second compound having structure:

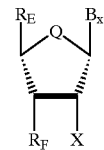

said contacting being for a time and under reaction conditions effective to form said linkage;

wherein:

(3')-$L_1$-$L_2$-$L_3$-$L_4$-(5') is $CR_{1a}R_{1b}$-$CR_{2a}R_{2b}$-$CR_{3a}R_{3b}$-$Z_4$, $CR_{1a}R_{1b}$-$CR_{2a}R_{2b}$-$Z_3$-$Z_4$, $CR_{1a}R_{1b}$-$Z_2$-$CR_{2a}R_{2b}$-$Z_4$, $Z_1$-$CR_{1a}R_{1b}$-$CR_{2a}R_{2b}$-$Z_4$, $CR_{1a}R_{1b}$-$Z_2$-$Z_3$-$Z_4$, $Z_1$-$CR_{2a}R_{2b}$-$Z_3$-$Z_4$ or $Z_1$-$Z_2$-$CR_{3a}R_{3b}$-$Z_4$;

$R_c$ is trifluoromethylsulfonyl, methylsulfonyl, halogen, O-trichloroacetimidate, acyloxy, dialkyl phosphite, 2,4, 6-trichlorophenyl, p-toluenesulfonyl, 4-dimethylaminoazobenzene-sulfonyl or 5-dimethylaminonaphthalenesulfonyl;

$R_F$ is $CR_{1a}R_{1b}$-$CR_{2a}R_{2b}$-$CR_{3a}R_{3b}$-$Z_4$, $CR_{1a}R_{1b}$-$CR_{2a}R_{2b}$-$Z_3$-$Z_4$, $CR_{1a}R_{1b}$-$Z_2$-$CR_{2a}R_{2b}$-$Z_4$, $Z_1$-$CR_{1a}R_{1b}$-$CR_{2a}R_{2b}$-$Z_4$, $CR_{1a}R_{1b}$-$Z_2$-$Z_3$-$Z_4$, $Z_{-1}$-$CR_{2a}R_{2b}$-$Z_3$-$Z_4$ or $Z_1$-$Z_2$-$CR_{3a}R_{3b}Z_4$;

$R_E$ is $R_C$, a nucleoside, a nucleotide, an oligonucleotide, an oligonucleoside or hydroxymethyl;

$R_D$ is $R_F$, hydroxyl, a nucleoside, a nucleotide, an oligonucleotide or an oligonucleoside;

$Z_1$, $Z_2$, $Z_3$ and Z4 are, independently, O, S, $NR_4$, Se, $P(=J_1)J_2$ or $Si(R_6)_2$;

$R_{1a}$, $R_{1b}$, $R_{2a}$, $R_{2b}$, $R_{3a}$ and $R_{3b}$ are, independently, H, $R_5$, O-$R_5$, S-$R_5$, $NR_4R_5$; or, independently, together $R_{1a}$ and $R_{1b}$, or $R_{2a}$ and $R_{2b}$, or $R_{3a}$ and $R_{3b}$ are=O;

$J_1$ is O, S, Se or $NR_4$;

$J_2$ is OH, $OR_5$, SH, $SR_5$, SeH, $R_5$, $BH_3$ or $NR_4R_5$;

$R_4$, $R_5$ and $R_6$ are, independently, H; $C_1$ to $C_{10}$ straight or branched chain lower alkyl or substituted lower alkyl; $C_2$ to $C_{10}$ straight or branched chain lower alkenyl or substituted lower alkenyl; $C_2$ to $C_{10}$ straight or branched chain lower alkynyl or substituted lower alkynyl; a $^{14}C$ containing lower alkyl, lower alkenyl or lower alkynyl; $C_7$ to $C_{14}$ substituted or unsubstituted alkaryl or aralkyl; a $^{14}C$ containing $C_7$ to $C_{14}$ alkaryl or aralkyl; $C_6$ to $C_{14}$ aryl; alicyclic; heterocyclic; a reporter molecule;

X is H, OH, $C_1$ to $C_{10}$ lower alkyl, substituted lower alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH3$, ONO2, NO2, N3, NH2, heterocycloalkyl, heterocycloalkaryl, aminoalkylamino, polyalkylamino or substituted silyl;

Q is O or $CH_2$; and

Bx is a heterocyclic base.

9. The method of claim 7 including repeating said steps b) and c) multiple times.

* * * * *

```
                          SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 17 bases
        (B) TYPE: nucleic acid
        (C) STRANDEDNESS: single
        (D) TOPOLOGY: linear (xi) SEQUENCE DESCRIPTION: SEQ ID NO:1:

CTCGTACCTT CCGGTCC                                                         17

(2) INFORMATION FOR SEQ ID NO:2:

(i) SEQUENCE CHARACTERISTICS:
        (A) LENGTH: 17 bases
        (B) TYPE: nucleic acid
        (C) STRANDEDNESS: single
        (D) TOPOLOGY: linear (xi) SEQUENCE DESCRIPTION: SEQ ID NO:2:

CTCGTACTTT CCGGTCC                                                         17

(2) INFORMATION FOR SEQ ID NO:3:

(i) SEQUENCE CHARACTERISTICS:
        (A) LENGTH: 16 bases
        (B) TYPE: nucleic acid
        (C) STRANDEDNESS: single
        (D) TOPOLOGY: linear (xi) SEQUENCE DESCRIPTION: SEQ ID NO:3:

GCCTTTTTTT TTTGCG                                                          16
```